(12) United States Patent
Humes et al.

(10) Patent No.: US 11,439,739 B2
(45) Date of Patent: *Sep. 13, 2022

(54) CARTRIDGE AND METHOD FOR INCREASING MYOCARDIAL FUNCTION

(71) Applicant: SeaStar Medical, Inc., Denver, CO (US)

(72) Inventors: H. David Humes, Ann Arbor, MI (US); Deborah A. Buffington, Ann Arbor, MI (US)

(73) Assignee: SeaStar Medical, Inc., Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/935,992

(22) Filed: Jul. 22, 2020

(65) Prior Publication Data

US 2021/0138142 A1 May 13, 2021

Related U.S. Application Data

(63) Continuation of application No. 15/492,518, filed on Apr. 20, 2017, now Pat. No. 10,722,637, which is a
(Continued)

(51) Int. Cl.
*B01D 61/20* (2006.01)
*A61M 1/34* (2006.01)
(Continued)

(52) U.S. Cl.
CPC ......... *A61M 1/3486* (2014.02); *A61K 31/00* (2013.01); *A61K 31/194* (2013.01); *A61M 1/16* (2013.01);
(Continued)

(58) Field of Classification Search
CPC ...... G02C 5/008; G02C 5/14; G02C 2200/14; A61M 1/3486; A61M 1/16; A61M 1/3687;
(Continued)

(56) References Cited

U.S. PATENT DOCUMENTS 3,275,657 A * 9/1966 Werner ................ C07D 319/06
549/333
3,489,145 A 1/1970 Judson et al.
(Continued)

FOREIGN PATENT DOCUMENTS

EP 0341413 A2 11/1989
EP 0461791 A1 12/1991
(Continued)

OTHER PUBLICATIONS

Abraham E et al., 'Efficacy and Safety of Tifacogin (Recombinant Tissue Factor Pathway Inhibitor) in Severe Sepsis: A Randomized Controlled Trial,' JAMA, Jul. 9, 2003 (Jul. 9, 2003), 290(2):238-47.
(Continued)

*Primary Examiner* — Joseph W Drodge
(74) *Attorney, Agent, or Firm* — Goodwin Procter LLP

(57) ABSTRACT

The present invention relates to a cytopheretic cartridge for use in treating and/or preventing inflammatory conditions that affect myocardial function and to related methods. The cartridge can be used in treating a subject with myocardial dysfunction, such as a subject with chronic heart failure and/or acute decompensated heart failure.

50 Claims, 34 Drawing Sheets

Related U.S. Application Data continuation of application No. 14/327,145, filed on Jul. 9, 2014, now abandoned, which is a continuation of application No. PCT/US2012/059615, filed on Oct. 10, 2012.

(60) Provisional application No. 61/584,337, filed on Jan. 9, 2012.

(51) Int. Cl.
| | |
|---|---|
| *A61M 1/16* | (2006.01) |
| *A61M 1/36* | (2006.01) |
| *A61K 31/00* | (2006.01) |
| *A61K 31/194* | (2006.01) |

(52) U.S. Cl.
CPC ............ *A61M 1/1625* (2014.02); *A61M 1/34* (2013.01); *A61M 1/3472* (2013.01); *A61M 1/3666* (2013.01); *A61M 1/3679* (2013.01); *A61M 1/3687* (2013.01); *B01D 61/20* (2013.01); *A61M 2202/0427* (2013.01); *A61M 2202/0439* (2013.01); *A61M 2205/126* (2013.01); *A61M 2210/125* (2013.01)

(58) Field of Classification Search
CPC .... A61M 1/34; A61M 1/3666; A61M 1/1625; A61M 1/3472; A61M 1/3679; A61M 2205/126; A61M 2210/125; A61M 2202/0439; A61M 2202/0427; A61M 1/1621; A61M 1/3403; A61M 1/36; A61M 2202/0339; A61K 31/194; A61K 31/00; A61F 2/01; B01D 61/14; B01D 61/18; B01D 61/20; B01D 61/24; B01D 61/28; B01D 61/30; B01D 2311/2626; C12M 1/12; C12M 1/126; C12M 25/02; C12M 25/10; C12M 25/12; C12M 29/04; C12M 29/16
USPC ........ 210/638, 639, 645, 650, 651; 435/375; 604/6.01, 6.03, 6.09
See application file for complete search history.

(56) References Cited

U.S. PATENT DOCUMENTS

| | | | |
|---|---|---|---|
| 4,323,455 A * | 4/1982 | Tanaka ................. | B01D 63/082 210/321.75 |
| 4,330,410 A | 5/1982 | Takenaka et al. | |
| 4,334,993 A | 6/1982 | Norton | |
| 4,500,309 A | 2/1985 | Diederich et al. | |
| 4,689,191 A | 8/1987 | Beck et al. | |
| 4,980,068 A | 12/1990 | Lavender | |
| 5,032,615 A | 7/1991 | Ward et al. | |
| 5,053,130 A | 10/1991 | Raff et al. | |
| 5,100,564 A | 3/1992 | Pall et al. | |
| 5,104,373 A | 4/1992 | Davidner et al. | |
| 5,147,290 A | 9/1992 | Jonsson | |
| 5,187,102 A | 2/1993 | Stocker et al. | |
| 5,217,627 A | 6/1993 | Pall et al. | |
| 5,229,012 A | 7/1993 | Pall et al. | |
| 5,236,586 A | 8/1993 | Antoni et al. | |
| 5,266,219 A | 11/1993 | Pall et al. | |
| 5,344,561 A | 9/1994 | Pall et al. | |
| 5,383,847 A | 1/1995 | Edelson | |
| 5,486,286 A | 1/1996 | Peterson et al. | |
| 5,496,819 A | 3/1996 | Okuyama et al. | |
| 5,501,795 A | 3/1996 | Pall et al. | |
| 5,545,339 A | 8/1996 | Bormann et al. | |
| 5,567,443 A | 10/1996 | Kashiwagi et al. | |
| 5,571,418 A | 11/1996 | Lee et al. | |
| 5,587,070 A | 12/1996 | Pall et al. | |
| 5,591,772 A * | 1/1997 | Lane ....................... | A61P 43/00 514/458 |
| 5,601,727 A | 2/1997 | Bormann et al. | |
| 5,616,254 A | 4/1997 | Pall et al. | |
| 5,652,050 A | 7/1997 | Pall et al. | |
| 5,679,264 A | 10/1997 | Gsell | |
| 5,707,526 A | 1/1998 | Kraus et al. | |
| 5,744,047 A | 4/1998 | Gsell et al. | |
| 5,804,079 A | 9/1998 | Brown | |
| 5,830,365 A | 11/1998 | Schneditz | |
| 5,846,419 A | 12/1998 | Nederlof | |
| 5,866,015 A | 2/1999 | Kramer | |
| 5,997,496 A * | 12/1999 | Sekiguchi ........... | A61M 1/3496 604/6.07 |
| 6,053,885 A | 4/2000 | Beshel | |
| 6,074,869 A | 6/2000 | Pall et al. | |
| 6,123,859 A | 9/2000 | Lee et al. | |
| 6,231,770 B1 | 5/2001 | Bormann et al. | |
| 6,242,600 B1 * | 6/2001 | Tamura ................. | C07D 401/12 544/295 |
| 6,251,276 B1 | 6/2001 | Motomura | |
| 6,488,860 B2 | 12/2002 | Mari et al. | |
| 6,498,007 B1 | 12/2002 | Adachi et al. | |
| 6,561,997 B1 | 5/2003 | Weitzel et al. | |
| 6,565,748 B1 | 5/2003 | Wang et al. | |
| 6,566,402 B2 | 5/2003 | Warnock | |
| 6,582,386 B2 | 6/2003 | Min et al. | |
| 6,595,943 B1 | 7/2003 | Burbank | |
| 6,653,131 B2 | 11/2003 | Humes | |
| 6,706,008 B2 | 3/2004 | Vishnoi et al. | |
| 6,730,266 B2 * | 5/2004 | Matson ............... | A61M 1/3472 210/195.2 |
| 6,736,972 B1 | 5/2004 | Matson | |
| 6,830,553 B1 | 12/2004 | Burbank et al. | |
| 6,911,007 B2 | 6/2005 | Nier et al. | |
| 6,939,468 B2 | 9/2005 | Wang et al. | |
| 7,125,493 B2 | 10/2006 | Wang et al. | |
| 7,201,730 B2 | 4/2007 | Davidner et al. | |
| 7,297,270 B2 | 11/2007 | Bernard et al. | |
| 7,351,218 B2 | 4/2008 | Bene | |
| 7,410,582 B2 | 8/2008 | Bernard et al. | |
| 7,442,546 B2 | 10/2008 | Humes | |
| 7,459,169 B2 | 12/2008 | Nilsson et al. | |
| 7,524,425 B2 | 4/2009 | Mari et al. | |
| 7,527,737 B2 | 5/2009 | Wang | |
| 7,531,133 B2 | 5/2009 | Hole et al. | |
| 7,591,954 B2 | 9/2009 | Kimura et al. | |
| 7,614,997 B2 * | 11/2009 | Bolling ............... | A61M 1/3659 600/16 |
| 7,674,235 B2 | 3/2010 | Nier et al. | |
| 7,699,806 B2 | 4/2010 | Ware et al. | |
| 7,799,335 B2 | 9/2010 | Herrmann et al. | |
| 7,829,553 B2 | 11/2010 | Arnold et al. | |
| 7,985,337 B2 | 7/2011 | Heuser et al. | |
| 8,048,419 B2 | 11/2011 | Humes | |
| 8,251,941 B2 * | 8/2012 | Humes ................... | A61P 43/00 514/458 |
| 8,361,459 B2 | 1/2013 | Messina et al. | |
| 8,409,126 B2 | 4/2013 | Humes et al. | |
| 8,425,445 B2 | 4/2013 | Humes et al. | |
| 8,425,446 B2 | 4/2013 | Humes et al. | |
| 8,425,447 B2 | 4/2013 | Humes et al. | |
| 8,430,832 B2 | 4/2013 | Humes et al. | |
| 8,501,008 B2 | 8/2013 | Lemke et al. | |
| 8,748,560 B2 | 6/2014 | Nakao et al. | |
| 9,029,144 B2 | 5/2015 | Szczypka et al. | |
| 9,128,093 B2 | 9/2015 | Humes et al. | |
| 9,181,082 B2 | 11/2015 | Borenstein et al. | |
| 9,341,626 B2 | 5/2016 | Humes et al. | |
| 9,475,566 B2 * | 10/2016 | Tange .................. | C07D 401/12 544/295 |
| 9,498,566 B2 | 11/2016 | Humes et al. | |
| 10,058,806 B2 * | 8/2018 | Tange ................. | A61M 1/3659 600/16 |
| 10,695,482 B2 | 6/2020 | Humes et al. | |
| 10,722,637 B2 * | 7/2020 | Humes ................ | A61M 1/3472 |
| 11,118,162 B2 | 9/2021 | Humes et al. | |
| 2002/0107469 A1 | 8/2002 | Bolan et al. | |
| 2002/0128259 A1 | 9/2002 | Ghazzi et al. | |

(56) References Cited

U.S. PATENT DOCUMENTS

| | | |
|---|---|---|
| 2003/0092668 A1* | 5/2003 | Liang .................... A61K 47/55 514/46 |
| 2003/0119184 A1* | 6/2003 | Humes ................ A61M 1/3687 435/369 |
| 2004/0124147 A1 | 7/2004 | Fissell et al. |
| 2004/0133145 A1 | 7/2004 | Bene |
| 2004/0142463 A1 | 7/2004 | Walker et al. |
| 2004/0171589 A1 | 9/2004 | Herrmann et al. |
| 2005/0143684 A1 | 6/2005 | Bolan et al. |
| 2005/0182125 A1* | 8/2005 | Lockhart ................ A61K 31/00 514/423 |
| 2005/0215937 A1 | 9/2005 | Spinale et al. |
| 2005/0236330 A1 | 10/2005 | Nier et al. |
| 2005/0281809 A1 | 12/2005 | Roberts et al. |
| 2006/0184085 A1 | 8/2006 | Kimura et al. |
| 2006/0292213 A1 | 12/2006 | Gerber et al. |
| 2007/0014688 A1 | 1/2007 | Hole et al. |
| 2007/0202536 A1 | 8/2007 | Yamanishi et al. |
| 2007/0269489 A1 | 11/2007 | Humes |
| 2008/0004712 A1 | 1/2008 | Humes et al. |
| 2008/0011691 A1 | 1/2008 | Yamada et al. |
| 2008/0110829 A1 | 5/2008 | Kobayashi |
| 2008/0145333 A1 | 6/2008 | Lentz |
| 2008/0203024 A1 | 8/2008 | Lemke et al. |
| 2008/0206757 A1 | 8/2008 | Lin et al. |
| 2008/0230475 A1 | 9/2008 | Mari et al. |
| 2008/0260710 A1 | 10/2008 | Kusunoki et al. |
| 2008/0319369 A1* | 12/2008 | Trutza ................. A61M 1/3472 604/6.01 |
| 2009/0022729 A1* | 1/2009 | Mackman .......... A61K 31/4184 514/369 |
| 2009/0060890 A1* | 3/2009 | Humes ................... A61K 31/34 424/93.71 |
| 2009/0081296 A1 | 3/2009 | Humes et al. |
| 2009/0176307 A1* | 7/2009 | Morgan .................... A61P 9/00 435/377 |
| 2009/0275874 A1 | 11/2009 | Shimagaki et al. |
| 2009/0318951 A1 | 12/2009 | Kashkarov et al. |
| 2009/0324567 A1 | 12/2009 | Spiers |
| 2010/0025335 A1 | 2/2010 | Shimaki |
| 2010/0062412 A1 | 3/2010 | Nirasawa et al. |
| 2010/0084331 A1 | 4/2010 | Heuser et al. |
| 2010/0087500 A1 | 4/2010 | Stover |
| 2010/0136687 A1 | 6/2010 | Westover et al. |
| 2010/0266562 A1 | 10/2010 | Humes et al. |
| 2010/0266563 A1 | 10/2010 | Humes et al. |
| 2010/0268146 A1 | 10/2010 | Humes et al. |
| 2010/0268147 A1 | 10/2010 | Humes et al. |
| 2011/0077616 A1* | 3/2011 | Bennett ................. A61B 5/0215 600/301 |
| 2011/0174733 A1* | 7/2011 | Heinrich ............. A61M 1/3679 210/645 |
| 2011/0190679 A1 | 8/2011 | Humes et al. |
| 2011/0196280 A1 | 8/2011 | Humes et al. |
| 2011/0197628 A1* | 8/2011 | Nose ................... A61M 1/3472 62/532 |
| 2011/0224645 A1* | 9/2011 | Winqvist ............ A61M 1/3472 |
| 2011/0250578 A1 | 10/2011 | Pappin |
| 2012/0189711 A1 | 7/2012 | Greenberg et al. |
| 2012/0201799 A1 | 8/2012 | Federspiel et al. |
| 2012/0258011 A1 | 10/2012 | Humes et al. |
| 2012/0277720 A1 | 11/2012 | Humes et al. |
| 2012/0322138 A1 | 12/2012 | Humes et al. |
| 2012/0323224 A1 | 12/2012 | Humes et al. |
| 2013/0046225 A1 | 2/2013 | Nose et al. |
| 2013/0288370 A1 | 10/2013 | Humes et al. |
| 2015/0246169 A1 | 9/2015 | Humes et al. |
| 2018/0093028 A1 | 4/2018 | Humes et al. |
| 2018/0126059 A1 | 5/2018 | Humes et al. |
| 2018/0171293 A1 | 6/2018 | Humes et al. |

FOREIGN PATENT DOCUMENTS

| | | |
|---|---|---|
| EP | 0732142 A2 | 9/1996 |
| JP | H08-509720 A | 10/1996 |
| JP | 2001-149471 A | 6/2001 |
| JP | 2001-276217 A | 10/2001 |
| JP | 2004-243048 A | 9/2004 |
| JP | 2006-510396 A | 3/2006 |
| JP | 2008-136757 A | 6/2008 |
| JP | 2008-206753 A | 9/2008 |
| JP | H10-017493 A | 1/2010 |
| WO | WO-1987/001593 A1 | 3/1987 |
| WO | WO-1987/006471 A1 | 11/1987 |
| WO | WO-1989/001967 A1 | 3/1989 |
| WO | WO-1993/024157 A1 | 12/1993 |
| WO | WO-1994/025047 A1 | 11/1994 |
| WO | WO-2004/037310 A2 | 5/2004 |
| WO | WO-2006/083322 A2 | 8/2006 |
| WO | WO-2007/025735 A1 | 3/2007 |
| WO | WO-2007/025738 A2 | 3/2007 |
| WO | WO-2007/057065 A1 | 5/2007 |
| WO | WO-2008/007465 A1 | 1/2008 |
| WO | WO-2008/038785 A1 | 4/2008 |
| WO | WO-2009/029801 A2 | 3/2009 |
| WO | WO-2009/128564 A1 | 10/2009 |
| WO | WO-2010/126967 A1 | 11/2010 |
| WO | WO-2012/051595 A1 | 4/2012 |
| WO | WO-2012/126967 A2 | 9/2012 |
| WO | WO-2013/106108 A2 | 7/2013 |
| WO | WO-2015/095553 A1 | 6/2015 |
| WO | WO-2015/110277 A1 | 7/2015 |

OTHER PUBLICATIONS

Alaoja H et al., 'Leukocyte Filtration to Decrease the Number of Adherent Leukocytes in the Cerebral Microcirculation After a Period of Deep Hypothermic Circulatory Arrest,' J Thorac Cardiovasc Surg, Dec. 2006 (Dec. 2006), 132(6):1339-47.

Aldea GS et al., 'Limitation of Thrombin Generation, Platelet Activation, and Inflammation by Elimination of Cardiotomy Suction in Patients Undergoing Coronary Artery Bypass Grafting Treated With Heparin-Bonded Circuits,' J Thorac Cardiovasc Surg, Apr. 2002 (Apr. 2002), 123(4):742-55.

Andonegui G et al., 'Mice That Exclusively Express TLR4 on Endothelial Cells Can Efficiently Clear a Lethal Systemic Gram-negative Bacterial Infection,' J Clin Invest, Jul. 2009 (Jul. 2009), 119(7):1921-30.

Andrew D. Michaels et al., "Microvascular Dysfunction in Acute Myocardial Infarction: Focus on the Roles of Platelet and Inflammatory Mediators in the No-Reflow Phenomenon", American Journal of Cardiology, Published 2000, vol. 85, pp. 50b-56b.

André P et al., 'Platelets Adhere to and Translocate on von Willebrand Factor Presented by Endothelium in Stimulated Veins,' Blood, Nov. 2000 (Nov. 2000), 96(10):3322-8.

Ann-Yeong Chong et al., "Viewpoint: The prothrombotic state in heart failure: A maladaptive inflammatory response?", European Journal of Heart Failure, 2007, Volumn 9, pp. 124-128. (Year: 2007).

Anonymous, 'CobeSpectra™ Apheresis System Essentials Guide,' Mar. 2005 (Mar. 2005), Gambro BCT, Inc., Lakewood CO (Pub), pp. 1-8 (Brochure).

Anonymous, 'CS-3000 Blood Cell Separator,' Unknown Publication Date, Cen-Med Enterprises, New Brunswick, NJ (Pub), pp. 1 (Internet Brochure).

Anonymous, 'Fenwal Amicus® Separator,' Oct. 2009 (Oct. 2009), Fenwal, Inc. Lake Zurich, NY (Pub), pp. 1-5 https:www.fenwalinc.com/Pages/Amicus.aspx (Brochure).

Anonymous, 'Fresenius COM.TEC Blood Cell Separator 510(k) Premarket Notification,' Sep. 5, 2006 (Sep. 5, 2006), Fresenius Medical Care North America, Lexington, MA (Pub), pp. 1-6.

Anonymous, 'Leukotrap® Filtration Systems for Whole Blood Derived Platelets,' 2006 (2006), Pall Corporation, East Hills, NY (Pub), pp. 1-8 (Brochure).

(56) References Cited

OTHER PUBLICATIONS

Anonymous, 'Therapeutic Apheresis: Basic Principles, Techniques and Practical Considerations,' Unknown Publication Date, Columbia University, New York, NY (Pub), pp. 1-4 www.pathology.columbia.edu/education/residency/aphersis_1.pdf <http://www.pathology.columbia.edu/education/residency/aphersis_1.pdf> (Powerpoint Presentation).
Anonymous, 'USRDS 2001 Annual Data Report: Atlas of End-Stage Renal Disease in the United States,' 1001 (2001), U.S. Renal Data System (Ed), NIH, National Institute of Diabetes and Digestive and Kidney Diseases, Bethesda, MD (Pub), p. 561.
Anonymous, 'V50 Apheresis System Service Manual,' Feb. 1987 (Feb. 1987), Haemonetics Corp, Braintree, MA (Pub), pp. 1-12.
Apsner R et al., 'Regional Anticoagulation with Acid Citrate Dextrose-A for Extracorporeal Photoimmunochemotherapy.' Vox Sang, Oct. 2002 (Oct. 2002), 83(3):222-6.
Asimakopoulos G et al., 'Lung Injury and Acute Respiratory Distress Syndrome After Cardiopulmonary Bypass,'Ann Thorac Surg, Sep. 1999 (Sep. 1999), 68(3):1107-15.
Aster RH and Jandl JH, 'Platelet Sequestration in Man. I. Methods,' J Clin Invest, May 1964 (May 1964), 43:843-55.
Aster RH and Jandl JH, 'Platelet Sequestration in Man. II. Immunological and Clinical Studies,' J Clin Invest, May 1964 (May 1964), 43:856-69.
Bagshaw SM et al., 'Is Regional Citrate Superior to Systemic Heparin Anticoagulation for Continuous Renal Replacement Therapy? A Prospective Observational Study in an Adult Regional Critical Care System,' J Crit Care, Jun. 2005 (Jun. 2005), 20(2):155-61.
Balke N et al., 'Inhibition of Degranulation of Human Polymorphonuclear Leukocytes by Complement Factor D,' FEBS Lett, Sep. 11, 1995 (Sep. 11, 1995), 371(3):300-2.
Basu S et al., 'Effects of Melagatran, a Novel Direct Thrombin Inhibitor, During Experimental Septic Shock,' Expert Opin Investig Drugs, May 2000 (May 2000), 9(5):1129-37.
Bernard GR et al., 'Efficacy and Safety of Recombinant Human Activated Protein C for Severe Sepsis,' N Engl J Med, Mar. 8, 2001 (Mar. 8, 2001), 344(10):699-709.
Bolling KS et al., 'Prevention of the Hypoxic Reoxygenation Injury with the Use of a Leukocyte-depleting Filter,' J Thorac Cardiovasc Surg, Jun. 1997 (Jun. 1997), 113(6):1081-9.
Bologa RM et al., 'Interleukin-6 Predicts Hypoalbuminemia, Hypocholesterolemia, and Mortality in Hemodialysis Patients,' Am J Kidney Dis, Jul. 1998 (Jul. 1998), 32(1):107-14.
Bombeli T et al., 'Adhesion of Activated Platelets to Endothelial Cells: Evidence for a GPIIbIIIa-Dependent Bridging Mechanism and Novel Roles for Endothelial Intercellular Adhesion Molecule 1 (ICAM-1), alphavbeta3 Integrin, and GPIbalpha,' J Exp Med, Feb. 2, 1998 (Feb. 2, 1998).
Bone RC, 'Sepsis, the Sepsis Syndrome, Multi-Organ Failure: A Plea for Comparable Definitions,' Ann Intern Med, Feb. 15, 1991 (Feb. 15, 1991), 114(4):332-3.
Bos JC et al,. 'Low Polymorphonuclear Cell Degranulation During Citrate Anticoagulation: A Comparison Between Citrate and Heparin Analysis,' Nephrol Dial Transplant, Jul. 1997 (Jul. 1997), 12(7):1387-93.
Bosman PJ et al., 'Access Flow Measurements in Hemodialysis Patients: in vivo Validation of and Ultrasound Dilution Technique,' J Am Soc Nephrol, Jun. 1996 (Jun. 1996), 7(6):966-9.
Buffington DH, Abstract of Grant No. 1R43DK074289-01, 'Cell Therapy for Septic Shock,' CRISP, May 2, 2006 (May 2, 2006), U.S. National Library of Medicine, NIH, Bathesda, MD (Pub), pp. 1-2 http://ewh.ieee.org/r6/ocs/en/PresentationMaterial/CRISP/2006/1R43DK074289-01.htm.
Buffington DH, Abstract of Grant No. 1R43DK080529-01, 'Selective Cytopheresis Therapy in Systemic Inflammatory Response Syndrome,' CRISP, Mar. 1, 2008 (Mar. 1, 2008), U.S. National Library of Medicine, NIH, Bathesda, MD (Pub), pp. 1-2 http://ewh.ieee.org/r6/ocs/en/PresentationMaterial/CRISP/2009/1R43DK080529-01.htm.
Buffington DH, Abstract of Grant No. 2R44DK074289-03, 'Cell Therapy for Septic Shock,' CRISP, May 2, 2006 (May 2, 2006), U.S. National Library of Medicine, NIH, Bathesda, MD (Pub), pp. 1-2 http://ewh.ieee.org/r6/ocs/en/PresentationMaterial/CRISP/2009/2R44DK074289-03.htm.
Buffington DH, Abstract of Grant No. 5R43DK074289-02, 'Cell Therapy for Septic Shock,' CRISP, Aug. 29, 2008 (Aug. 29, 2008), U.S. National Library of Medicine, NIH, Bathesda, MD (Pub), (2 pages) downloaded from <http://crisp.cit.nih.gov/crisp/CRISP_LIB.getdoc?textkey-7228623&p_grant_num=5R43DK074289-02&p>.
Böhler J et al., 'Mediators of Complement-Independent Granulocyte Activation During Haemodialysis: Role of Calcium, Prostaglandins and Leukotrienes,' Nephrol Dial Transplant, 1993 (1993), 8(12):1359-65.
Böhler J et al., 'Reduction of Granulocyte Activation During Hemodialysis with Regional Citrate Anticoagulation: Dissociation of Complement Activation and Neutropenia From Neutrophil Degranulation,' J Am Soc Nephrol, Feb. 1996 (Feb. 1996), 7(2):234-41.
Carney DE et al., 'Matrix Metalloproteinase Inhibitor Prevents Acute Lung Injury After Cardiopulmonary Bypass,' Circulation, Jul. 27, 1999 (Jul. 27, 1999), 100(4):400-6.
Chai PJ et al., 'Effects of Ischemia on Pulmonary Dysfunction After Cardiopulmonary Bypass,' Ann Thorac Surg, Mar. 1999 (Mar. 1999), 67(3):731-5.
Chertow GM et al., 'Mortality After Acute Renal Failure: Models for Prognostic Stratification and Risk Adjustment,' Kidney Int, Jul. 19, 2006 (Jul. 19, 2006)(ePub), 70(6):1120-6.
Clark SC, 'Lung Injury After Cardiopulmonary Bypass,' Perfusion, Jul. 2006 (Jul. 2006), 21(4):225-8.
Cohn JN et al., 'A Dose-Dependent Increase in Mortality with Vesnarione Among Patients with Severe Heart Failure,' N Engl J Med, Dec. 17, 1998 (Dec. 17, 1998), 339(25):1810-6.
Coleman SM and Demastrice L, 'Leukocyte Depletion Reduces Postoperative Oxygen Requirements,' Ann Thorac Surg, Nov. 1994 (Nov. 1994), 58(5):1567-8.
Conraads VM et al., 'Intracellular Monocyte Cytokine Production and CD14 Expression are Up-regulated in Severe vs Mild Chronic Heart Failure,' J Heart Transplant, Jul. 2005 (Jul. 2005), 24(7):854-9.
Cruz D et al., 'The Future of Extracorporeal Support,' Crit Care Med, Apr. 2008 (Apr. 2008), 36(4 Suppl):S243-52.
Cubattoli L et al., 'Citrate Anticoagulation During CVVH in High Risk Bleeding Patients,' Int J Artif Organs, Mar. 2007 (Mar. 2007), 30(3):244-52.
Damsgaard CT et al., 'Whole-Blood Culture is a Valid Low-cost Method to Measure Monocytic Cytokines—A Comparison of Cytokine Production in Cultures of Human Whole-Blood, Mononuclear Cells and Monocytes,' J Immunol Methods, Nov. 8, 2008 (Nov. 8, 2008)(ePub), 340(2):95-101.
Deng JC et al., 'Sepsis-induced Suppression of Lung Innate Immunity is Mediated by IRAK-M,' J Clin Invest, Aug. 17, 2006 (Aug. 17, 2006)(ePub), 116(9):2532-42.
Depner TA, 'Techniques for Prospective Detection of Venous Stenosis,' Adv Ren Replace Ther, Jul. 1994 (Jul. 1994), 1(2):119-30.
Dickneite G and Czech J, 'Combination of Antibiotic Treatment with the Thrombin Inhibitor Recombinant Hirudin for the Therapy of Experimental *Klebsiella pneumoniae* Sepsis,' Thromb Haemost, Jun. 1994 (Jun. 1994), 71(6):768-72.
Ding F et al., 'A Biomimetic Membrane Device That Modulates the Excessive Inflammatory Response to Sepsis,' PLoS, Apr. 14, 2011 (Apr. 14, 2011), 6(4):e18584.
Ding F et al., 'A Selective Cytopheretic Inhibitory Device (SCD) Accelerates Renal Recovery and Improves Mortality in ICU Patients with AKI and MOF in an Exploratory Clinical Study,' ASAIO Renal Abstracts, Mar./Apr. 2010 (Mar.-Apr. 2010), 56(2):140.
Ding F et al., 'The Effects of a Novel Therapeutic Device on Acute Kidney Injury Outcomes in the Intensive Care Unit: A Pilot Study,' ASAIO J, Sep.-Oct. 2011 (Sep.-Oct. 2011), 57(5):426-32.
Ding F et al., (2008), 'A Novel Selective Cytopheretic Injury Device (SCD) Inhibits Circulating Leukocyte Activation and Ameliorates Multiorgan Dysfunction in a Procine Model of Septic Shock,' Poster F-PO1565, J Am Soc Nephrol, 19:458A (Poster).

(56) References Cited

OTHER PUBLICATIONS

Ding F et al., (2009), 'Central Role of Leukocyte Activation in Acute Kidney Injury and Multiorgan Dysfunction in a Procine Model of Septic Shock,' Poster F-PO1809, J Am Soc Nephrol, 20:527A (Poster).
Dodd-o JM et al., 'Effect of NADPH Oxidase Inhibition on Cardiopulmonary Bypass-induced Lung Injury,' Am J Physiol Heart Circ Physiol, Aug. 2004 (Aug. 2004), 287(2):H927-36.
Eichler W et al., 'A Rise of MMP-2 and MMP-9 in Bronchoalveolar Lavage Fluid is Associated with Acute Lung Injury After Cardiopulmonary Bypass in Swine Model,' Perfusion, Apr. 2003 (Apr. 2003), 18(2):107-13.
Eichler W et al., 'Na/H+ Exchange Inhibitor Cariporide: Effects on Respiratory Dysfunction After Cardiopulmonary Bypass,' Perfusion, Jan. 2004 (Jan. 2004), 19(1):33-40.
El Kebir D et al., 'Effects of Inhaled Nitric Oxide on Inflammation and Apoptosis After Cardiopulmonary Bypass,' Chest, Oct. 2005 (Oct. 2005), 128(4):2910-7.
El Kebir D et al., 'The Anti-inflammatory Effect of Inhaled Nitric Oxide on Pulmonary Inflammation in a Swine Model,' Can J Physiol Pharmacol, Mar. 2005 (Mar. 2005), 83(3):252-8.
Elihu N et al., 'Chelation Therapy in Cardiovascular Disease: Ethylenediaminetetraacetic Acid, Deferoxamine, and Dexrazoxane,' J Clin Pharmacol, Feb. 1998 (Feb. 1998), 38(2):101-5.
Emmrich J et al., 'Leukocytapheresis (LCAP) in the Management of Chronic Active Ulcerative Colitis—Results of a Randomized Pilot Trial,' Dig Dis Sci, Apr. 5, 2007 (Apr. 5, 2007) (ePub), 52(9):2044-53.
Extended European Search Report (EPO Form 1507S) for European Application No. 12865238.5-1651 dated May 17, 2016 (10 pages).
Fan ST and Edgington TS, 'Integrin Regulation of Leukocyte Inflammatory Functions,' J Immunol, Apr. 1, 1993 (Apr. 1, 1993), 150(7):2972-80.
Ferreira FL et al., 'Serial Evaluation of SOFA Score to Predict Outcome in Critically Ill Patients,' JAMA, Oct. 10, 2001 (Oct. 10, 2001), 286(14):1754-8.
Filkins JP and Di Luzio NR, 'Heparin Protection in Endotoxin Shock,' Am J Physiol, May 1968 (May 1968), 214(5):1074-7.
Fissell WH et al., 'Bioartificial Kidney Alters Cytokine Response and Hemodynamics in Endotoxin-Challenged Uremic Animals,' Blood Purif, 2002 (2002), 20(1):55-60.
Fissell WH et al., 'Bioartificial Kidney Ameliorates Gram-Negative Bacteria-Induced Septic Shock in Uremic Animals,' J Am Soc Nephrol, 2003 (2003), 14(2):454-61.
Flanigan MJ et al., 'Reducing the Hemorrhagic Complications of Hemodialysis: A Controlled Comparison of Low-dose Heparin and Citrate Anticoagulation,' Am J Kidney Dis, Feb. 1987 (Feb. 1987), 9(2):147-53.
Fonarow GC, 'The Acute Decompensated Heart Failure National Registry (ADHERE™): Opportunities to Improve Care of Patients Hospitalized with Acute Decompensated Heart Failure,' Rev Cardiovasc Med, 2003 (2003), 4(Suppl 7):S21-30.
Frenette PS et al., 'Platelet-Endothelial Interactions in Inflamed Mesenteric Venules,' Blood, Feb. 15, 1998 (Feb. 15, 1998), 91(4):1318-24.
Fuhlbrigge RC et al., 'Sialylated Fucosylated Ligands for L-Selectin Expressed on Leukocytes Mediate Tethering and Rolling Adhesions in Physiologic Flow Conditions,' J Cell Biol, Nov. 1996 (Nov. 1996), 135(3):837-48.
Garrood T et al., 'Molecular Mechanisms of Cell Recruitment to Inflammatory Sites: General and Tissue-Specific Pathways.' Rheumatology (Oxford), Nov. 30, 2005 (Nov. 30, 2005)(ePub), 45(3):250-60.
Gritters M et al., 'Citrate Anticoagulation Abolishes Degranulation of Polymorphonuclear Cells and Platelets and Reduces Oxidative Stress During Haemodialysis,' Nephrol Dial Transplant, Sep. 6, 2005 (Sep. 6, 2005)(ePub), 21(1):153-9.
Grooteman MP et al., 'Hemodialysis-Induced Degranulation of Polymorphonuclear Cells: No Correlation Between Membrane Markers and Degranulation Products,' Nephron, Jul. 2000 (Jul. 2000), 85(3):267-74.
Gu YJ et al., 'Leukocyte Depletion Results in Improved Lung Function and Reduced Inflammatory Response After Cardiac Surgery,' J Thorac Cardiovasc Surg, Aug. 1996 (Aug. 1996), 112(2):494-500.
Harris MB et al., 'Polymorphonuclear Leukocytes Prepared by Continuous-Flow Filtration Leukapheresis: Viability and Function,' Blood, Nov. 1974 (Nov. 1974), 44(5):707-13.
Herzig GP et al., 'Granulocyte Collection by Continuous-Flow Filtration Leukapheresis,' Blood, Apr. 1972 (Apr. 1972), 39(4):554-67.
Hester RL et al., 'Non-Invasive Determination of Recirculation in the Patient on Dialysis,' ASAIO J, Jul.-Sep. 1992 (Jul.-Sep. 1992), 38(3):M190-3.
Hetzel GR et al., 'Regional Citrate Versus Systemic Heparin for Anticoagulation in Critically Ill Patients on Continuous Venovenous Haemofiltration: A Prospective Randomized Multicentre Trial,' Nephrol Dial Transplant, Sep. 27, 2010 (Sep. 27, 2010)(ePub), 26(1):232-9.
Himmelfarb J et al., 'Impaired Monocyte Cytokine Production in Critically Ill Patients with Acute Renal Failure,' Kidney Int, Dec. 2004 (Dec. 2004), 66(6):2354-60.
Himmelfarb J et al., 'Plasma Aminothiol Oxidation in Chronic Hemodialysis Patients,' Kidney Int, Feb. 2002 (Feb. 2002), 61(2):705-16.
Himmelfarb J et al., 'Plasma Protein Thiol Oxidation and Carbonyl Formation in Chronic Renal Failure,' Kidney Int, Dec. 2000 (Dec. 2000), 58(6):2571-8.
Humes et al., (2012), 'Immunomodulation with a Selective Cytopheretic Device (SCD) Improves Myocardial Contractility and Renal Sodium Excretion in a Canine Model of Congestive Heart Failure,' Abstract TH-OR015, J Am Soc Nephrol, 23:3A (Abstract).
Humes H et al., (2008), 'A Novel Selective Cytopheretic Inhibitory Device (SCD) Improves Mortality in ICU Patients with Acute Kidney Injury (AKI) and Multiorgan Failure (MOF) in a Phase II Clinical Study,' Poster F-PO1564, J Am Soc Nephrol, 19:458A (Poster).
Humes HD et al., 'A Selective Cytopheretic Inhibitory Device to Treat the Immunological Dysregulation of Acute and Chronic Renal Failure,' Blood Purif, Jan. 8, 2010 (Jan. 8, 2010)(ePub), 29(2):183-90.
Humes HD et al., 'Cell Therapy with a Tissue-Engineered Kidney Reduces the Multiple-Organ Consequences of Septic Shock,' Crit Care Med, Oct. 2003 (Oct. 2003), 31(10):2421-8.
Humes HD et al., 'Initial Clinical Results of the Bioartificial Kidney Containing Human Cells in ICU Patients with Acute Renal Failure,' Kidney Int, Oct. 2004 (Oct. 2004), 66(4):1578-88.
Humes HD et al., 'Metabolic Replacement of Kidney Function in Uremic Animals with a Bioartificial Kidney Containing Human Cells,' Am J Kidney Dis, May 2002 (May 2002), 39(5):1078-87.
Humes HD et al., 'Renal Cell Therapy is Associated with Dynamic and Individualized Responses in Patients with Acute Renal Failure,' Blood Purif, 2003 (2003), 21(1):64-71.
Humes HD et al., 'Replacement of Renal Function in Uremic Animals with Tissue-Engineered Kidney,' Nat Biotechnol, May 1999 (May 1999), 17(5):451-5.
Humes HD et al., 'The Bioartificial Kidney in the Treatment of Acute Renal Failure,' Kidney Int Suppl, May 2002 (May 2002), 61(Suppl 80):S121-S125.
Humes HD et al., 'Tissue Engineering of a Bioartificial Renal Tubule Assist Device: in vitro Transport and Metabolic Characteristics.' Kidney Int, Jun. 1999 (Jun. 1999), 55(6):2502-14.
Humes HD, 'Bioartificial Kidney for Full Renal Replacement Therapy,' Semin Nephrol, Jan. 2000 (Jan. 2000), 20(1):71-82.
Höri WH et al., 'Physiochemical Characterization of Polypeptide Present in Uremic Serum That Inhibits the Biological Activity of Polymorphonuclear Cells,' Proc Natl Acad Sci USA, Aug. 1990 (Aug. 1990), 87(16):6353-7.
Imai M et al., 'Therapy with Cardiac Contractility Modulation Electrical Signals Improves Left Ventricular Function and Remodeling in Dogs with Chronic Heart Failure,' J Am Coll Cardiol, May 17, 2007 (May 17, 2007)(ePub), 49(21):2120-8.

(56) References Cited

OTHER PUBLICATIONS

Imai Y et al., 'Identification of a Carbohydrate-Based Endothelial Ligand for a Lymphocyte Homing Receptor,' J Cell Biol, Jun. 1991 (Jun. 1991), 113(5):1213-21.
International Search Report (Form ISA/210) for International Application PCT/US2012/059615 dated Jun. 17, 2013 (3 pages).
Itoh S et al., 'Platelet Activation Through Interaction with Hemodialysis Membranes Induces Neutrophils to Produce Reactive Oxygen Species,' J Biomed Mater Res A, May 2006 (May 2006), 77(2):294-303.
Janatova J, 'Activation and Control of Complement, Inflammation, and Infection Associated with the use of Biomedical Polymers,' ASAIO J, Nov.-Dec. 2000 (Nov.-Dec. 2000), 46(6):S53-62.
Jansen NJ et al., 'Endotoxin Release and Tumor Necrosis Factor Formation During Cardiopulmonary Bypass,' Ann Thorac Surg, Oct. 1992 (Oct. 1992), 54(4):744-7.
Johnston L et al., (2010), 'Integration of a Selective Cytopheretic Inhibitory Device (SCD) into a Protable Sorbent Dialysis System,' Poster F-PO1101, J Am Soc Nephrol, 21:363A (Poster).
Jung J-Y et al., 'Mechanism of Action of Selective Cytopheretic Device to Ameliorate Multiorgan Dysfunction in Septic Shock,' ASAIO Renal Abstracts, Mar./Apr. 2010 (Mar.-Apr. 2010), 56(2):140.
Kaneider NC et al., 'Therapeutic Targeting of Molecules Involved in Leukocyte-endothelial Cell Interactions,' FEBS J, Sep. 5, 2006 (Sep. 5, 2006)(ePub), 273(19):4416-24.
Kaplow LS and Goffinet JA, 'Profound Neutropenia During the Early Phase of Hemodialysis,' JAMA, Mar. 25, 1968 (Mar. 25, 1968), 203(13):1135-7.
Kelly KJ, 'Acute Renal Failure: Much More than a Kidney Disease,' Semin Nephrol, Mar. 2006 (Mar. 2006), 26(2):105-13.
Kidane AG et al., 'Anticoagulant and Antiplatelet Agents: Their Clinical and Device Application(s) Together with Usages to Engineer Surfaces,' Biomacromolecules, May-Jun. 2004 (May-Jun. 2004), 5(3):798-813.
Kim WR et al., 'The Relative Role of the Child-Pugh Classification and the Mayo Natural History Model in the Assessment of Survival in Patients with Primary Sclerosing Cholangitis,' Hepatology, Jun. 1999 (Jun. 1999), 29(6):1643-8.
Kimmel PL et al., 'Immunologic Function and Survival in Hemodialysis Patients,' Kidney Int, Jul. 1998 (Jul. 1998), 54(1):236-44.
Knaus WA et al., 'APACHE II: A Severity of Disease Classification Systems,' Crit Care Med, Oct. 1985(Oct. 1985), 13(10):818-29.
Kono T et al., 'Left Atrial Contribution to Ventricular Filling During the Course of Evolving Heart Failure,' Circulation, Oct. 1992 (Oct. 1992), 86(4):1317-22.
Koster A et al., 'The More Closed the Bypass System the Better: A Pilot Study on the Effects of Reduction of Cardiotomy Suction and Passive Venting on Hemostatic Activation During On-pump Coronary Artery Bypass Grafting,' Perfusion, Sep. 2005 (Sep. 2005), 20(5):285-8.
Kozek-Langenecker SA et al., 'Effect of Prostacyclin on Platelets, Polymorphonuclear Cells, and Heterotypic Cell Aggregation During Hemofiltration,' Crit Care Med, Mar. 2003 (Mar. 2003), 31(3):864-8.
Kutsogiannis DJ et al., 'Regional Citrate Anticoagulation in Continuous Venovenous Hemodiafilration,' Am J Kidney Dis, May 2000 (May 2000), 35(5):802-11.
Kutsogiannis DJ et al., 'Regional Citrate Versus Systemic Heparin Anticoagulation for Continuous Renal Replacement in Critically Ill Patients,' Kidney Int, Jun. 2005 (Jun. 2005), 67(6):2361-7.
Lake EW and Humes HD, 'Acute Renal Failure: Directed Therapy to Enhance Renal Tubular Regeneration,' Semin Nephrol, Jan. 1994 (Jan. 1994), 14(1):83-97.
Lassen NA et al., 'Indicator Methods for Measurement of Organ and Tissue Blood Flow,' Comp Physiol, Jan. 1, 2011 (Jan. 1, 2011)(ePub), pp. 21-63 DOI: 10.1002/cphy.cp020302.
Leypoldt JK et al., 'Vascular Access Blood Flow Rates (Qa) Measured from Increases (Delta) in Hematocrit (H) when Applying Ultrafiltration (UF),' J Am Soc Nephrol, Sep. 1996 (Sep. 1996), 6(3):1412 Abstract A0828.
Lindsay RM, 'A Comparison of Methods for the Measurement of Access Recirculation [AR] and Access Flow [Qa],' J Am Soc Nephrol, Sep. 1996 (Sep. 1996), 6(3):1412 Abstract A0831.
Lindsay RM, 'The Measurement of Hemodialysis Access Blood Flow Rates by the Hemodynamic Monitor,' J Am Soc Nephrol, Sep. 1996 (Sep. 1996), 6(3):1412 Abstract A0830.
Lohr JW et al., 'Safety of Regional Citrate Hemodialysis in Acute Renal Failure,' Am J Kidney Dis, Feb. 1998 (Feb. 1998), 13(2):104-7.
Madeline R. Vann, Aug. 26, 2009, Retrieved from the Internet: <URL:https://www.everydayhealth.com/alternative-health/chelation-therapy-and-heart-disease.aspx>.
Maroszynska I and Fiedor P, 'Leukocytes and Endothelium Interaction as Rate Limiting Step in the Inflammatory Response and a Key Factor in the Ischemia-Reperfusion Injury,' Ann Transplant, 2000 (2000), 5(4):5-11.
Massie BM et al., 'Rolofylline, an Adenosine A1-Receptor Antagonist, in Acute Heart Failure,' N Engl J Med, Oct. 2010 (Oct. 2010), 363(15):1419-28.
Mebazaa A et al., 'Levosimendan vs Dobutamine for Patients with Acute Decompensated Heart Failure: The SURVIVE Randomized Trial,' JAMA, May 2007 (May 2007), 297(17):1883-91.
Mehta R et al., (2011), 'A Comparison of Clinical Outcomes Between the Selective Cytopheric Device and Case-Matched Historical Controls from the Picard Database,' Poster TH-PO072, J Am Soc Nephrol, 22:127A (Poster).
Mehta RL et al., 'Spectrum of Acute Renal Failure in the Intensive Care Unit: The PICARD Experience,' Kidney Int, Oct. 2004 (Oct. 2004), 66(4):1613-21.
Messent M et al., 'Adult Respiratory Distress Syndrome Following Cardiopulmonary Bypass: Incidence and Prediction,' Anaesthesia, Mar. 1992 (Mar. 1992), 47(3):267-8.
Meyer J et al., 'Heparin in Experimental Hyperdynamic Sepsis,' Crit Care Med, Jan. 1993 (Jan. 1993), 21(1):84-9.
Mishra J et al., 'Neutrophil Gelatinase-Associated Lipocalin (NGAL) as a Biomarker for Acute Renal Injury After Cardiac Surgery,' Lancet, Apr. 2-8, 2005 (Apr. 2-8, 2005), 365(9466):1231-8.
Monchi M et al., 'Citrate vs Heparin for Anticoagulation in Continuous Venovenous Hemofiltration: A Prospective Randomized Study,' Intensive Care Med, Nov. 5, 2003 (Nov. 5, 2003)(ePub), 30(2):260-5.
Morioka K et al., 'Leukocyte and Platelet Depletion with a Blood Cell Separator: Effects on Lung Injury After Cardiac Surgery with Cardiopulmonary Bypass,' J Thorac Cardiovasc Surg, Jan. 1996 (Jan. 1996), 111(1):45-54.
Morita H et al., 'Effects of Long-term Monotherapy with Metoprolol CR/XL on the Progression of Left Ventricular Dysfunction and Remodeling in Dogs with Chronic Heart Failure,' Cardiovasc Drugs Ther, Sep. 2002 (Sep. 2002), 16(5):443-9.
Morita H et al., 'Selective Matrix Metalloproteinase Inhibition Attenuates Progression of Left Ventricular Dysfunction and Remodeling in Dogs with Chronic Heart Failure,' Am J Physiol Heart Circ Physiol, Jan. 20, 2006 (Jan. 20, 2006)(ePub), 290(6):H2522-7.
Nakamura T et al., 'Ceramide Regulates Oxidant Release in Adherent Human Neutrophils,' J Biol Chem, Jul. 15, 1994 (Jul. 15, 1994), 269(28):18384-9.
National Kidney Foundation, 'NKF-K/DOQI Clinical Practice Guidelines for Vascular Access: Update 2000,' Am J Kidney Dis, Jan. 2001 (Jan. 2001), 37(1 Suppl 1):S137-40, S150-56.
National Kidney Foundation, 'Quality Initiative Clinical Practice Monitoring and Maintenance, Guideline 10, Monitoring Dialysis AV Grafts for Stenosis, Guideline 11 Monitoring Primary AV Fistulae for Stenosis and Guideline 12 Recirculation Methodology, Limits, Evaluation, and Follow-up,' Am J Kidney Dis, Oct. 1997 (Oct. 1997), 30(4 Suppl 3):S162-6.
Nurmohamed SA et al., 'Continuous Venovenous Hemofiltration With or Without Predilution Regional Citrate Anticoagulation: A Prospective Study,' Blood Purif, Aug. 14, 2007 (Aug. 14, 2007)(ePub), 25(4):316-23.
O'Connor CM et al., 'Effect of Nesiritide In Patients with Acute Decompensated Heart Failure,' N Engl J Med, Jul. 7, 2011 (Jul. 7, 2011), 365(1):32-43.

(56) References Cited

OTHER PUBLICATIONS

Oudemans-van Straaten HM et al., 'Citrate Anticoagulation for Continuous Venovenous Hemofiltration,' Crit Care Med, Feb. 2009 (Feb. 2009), 37(2):545-52.
Oudemans-van Straaten HM, 'Citrate Anticoagulation for Continuous Renal Replacement Therapy in the Critically Ill,' Blood Purif, Jan. 8, 2010 (Jan. 8, 2010)(ePub), 29(2):191-6.
Palanzo DA et al., 'Clinical Evaluation of the LeukoGuard (LG-6) Arterial Line Filter for Routine Open-Heart Surgery,' Perfusion, Nov. 1993 (Nov. 1993), 8(6):489-96.
Parikh CR et al., 'Urinary IL-18 is an Early Predictive Biomarker of Acute Kidney Injury After Cardiac Surgery,' Kidney Int, May 17, 2006 (May 17, 2006)(ePub), 70(1):199-203.
Pennathur S and Heinecke JW, 'Mechanisms of Oxidative Stress in Diabetes: Implications for the Pathogenesis of Vascular Disease and Antioxidant Therapy,' Front Biosc, Jan. 1, 2004 (Jan. 1, 2004), 9:565-74.
Pennathur S et al., 'A Hydroxyl Radical-like Species Oxidizes Cynomolgus Monkey Artery Wall Proteins in Early Diabetic Vascular Disease,' J Clin Invest, Apr. 2001 (Apr. 2001), 107(7):853-60.
Picone AL et al., 'Multiple Sequential Insults Cause Post-Pump Syndrome,' Ann Thorac Surg, Apr. 1999 (Apr. 1999), 67(4):978-85.
Pinnick RV et al., 'Regional Citrate Anticoagulation for Hemodialysis in the Patient at High Risk for Bleeding,' N Engl J Med, Feb. 3, 1983 (Feb. 3, 1983), 308(5):258-61.
Pino CJ et al., 'A Selective Cytopheretic Inhibitory Device for Use During Cardiopulmonary Bypass Surgery,' Perfusion, Apr. 16, 2010 (Apr. 16, 2010)(ePub), 27(4):311-9.
Pino CJ et al., 'Cardiopulmonary Bypass Surgery Aided by a Selective Cytopheretic Inhibitory Device,' ASAIO Bioengin Abstracts, Mar./Apr. 2011 (Mar.-Apr. 2011), 57(2):112.
Polaschegg HD, 'Access Physics,' Semin Dial, Jan. 16, 2002 (Jan. 16, 2002)(ePub), 12(1):S33-S40.
Rabb H et al., 'Acute Renal Failure Leads to Dysregulation of Lung Salt and Water Channels,' Kidney Int, Feb. 2003 (Feb. 2003), 63(2):600-6.
RD Miller, 'Anticoagulation for CPB,' *Miller's Anesthesia*, (6th Ed, 2005), Ronald D Miller (Ed), Elsevier Health Services, Philadelphia PA (Pub), (4 pages) downloaded on Aug. 23, 2007 from http://www.mdconsult.com/das/book/body/76819015-2/0/1255/1438.html?tocnode=53063.
RD Miller, 'Cardiopulmonary Bypass,' *Miller's Anesthesia*, (6th Ed, 2005), Ronald D Miller (Ed), Elsevier Health Services, Philadelphia PA (Pub), (2 pages) downloaded on Aug. 23, 2007 from http://www.mdconsult.com/das/book/body/76818435-2/0/1255/1437.html?tocnode=53063.
RD Miller, 'Common Problems After Cardiopulmonary Bypass,' *Miller's Anesthesia*, (6th Ed, 2005), Ronald D Miller (Ed), Elsevier Health Services, Philadelphia PA (Pub), (5 pages) downloaded on Aug. 23, 2007 from http://www.mdconsult.com/das/book/body/76819015-2/0/1255/1445.html?tocnode=53063.
RD Miller, 'Heparin Reversal,' *Miller's Anesthesia*, (6th Ed, 2005), Ronald D Miller (Ed), Elsevier Health Services, Philadelphia PA (Pub), (2 pages) downloaded on Aug. 23, 2007 from http://www.mdconsult.com/das/book/body/76819015-2/0/1255/1444.html?tocnode=53063.
RD Miller, 'Management of CPB,' *Miller's Anesthesia*, (6th Ed, 2005), Ronald D Miller (Ed), Elsevier Health Services, Philadelphia PA (Pub), (6 pages) downloaded on Aug. 23, 2007 from http://www.mdconsult.com/das/book/body/76819015-2/0/1255/1442.html?tocnode=53063.
RD Miller, 'Pathobiology of CPB,' *Miller's Anesthesia*, (6th Ed, 2005), Ronald D Miller (Ed), Elsevier Health Services, Philadelphia PA (Pub), (4 pages) downloaded on Aug. 23, 2007 from http://www.mdconsult.com/das/book/body/76819015-2/0/1255/1440.html?tocnode=53063.
RD Miller, 'Separation from CPB,' *Miller's Anesthesia*, (6th Ed, 2005), Ronald D Miller (Ed), Elsevier Health Services, Philadelphia PA (Pub), (2 pages) downloaded on Aug. 23, 2007 from http://www.mdconsult.com/das/book/body/76819015-2/0/1255/1443.html?tocnode=53063.
Rinder HM et al., 'Activated and Unactivated Platelet Adhesion to Monocytes and Neutrophils,' Blood, Oct. 1, 1991 (Oct. 1, 1991), 78(7):1760-9.
Romo GM et al., 'The Glycoprotein Ib-IX-V complex is a Platelet Counterreceptor for P-Selectin,' J Exp Med, Sep. 20, 1999 (Sep. 20, 1999), 190(6):803-14.
Rosen SD et al., 'L-Selectin: A Lectin-like Leukocyte Adhesion Protein,' Trends Glycosci Glycotechnol, Jan. 1992 (Jan. 1992), 4(15):1-13.
Rumberger JA et al., 'Use of Ultrafast Computed Tomography to Quantitate Regional Myocardial Perfusion: A Preliminary Report,' J Am Coll Cardiol, Jan. 1987 (Jan. 1987), 9(1):59-69.
Salem and Mujais, 'Chapter 5,' Dialysis Therapy, 2nd Ed, 1993 (1993), Allen R Nissenson and Richard N Fine (eds), Elsevier Health Services, Philadelphia PA (Pub), pp. 65-77 ISBN-13:1560534269.
Sawa Y et al., 'Evaluation of Leukocyte-Depleted Terminal Blood Cardioplegic Solution in Patients Undergoing Elective and Emergency Coronary Bypass Grafting,' J Thorac Cardiovasc Surg, Dec. 1994 (Dec. 1994), 108(6):1125-31.
Schaff UY, Yamayoshi I, Tse T, Griffin D, Kibathi L, Simon SI. Calcium flux in neutrophils synchronizes beta2 integrin adhesive and signaling events that guide inflammatory recruitment. Ann Biomed Eng. Apr. 2008;36(4):632-46.
Schendeditz D, 'Measurement of Access Flow by Thermodilution: in vitro Experiments,' J Am Soc Nephrol, Sep. 1995 (Sep. 1995), 6(3):502.
Schiffer ER et al., 'Evaluation of Unfractionated Heparin and Recombinant Hirudin on Survival in a Sustained Ovine Endotoxin Shock Model,' Crit Care Med, Dec. 2002 (Dec. 2002), 30(12):2689-99.
Scholz M and Cinatl J, 'Fasa/FasL Interaction: A Novel Immune Therapy Approach with Immobilized Biologicals,' Med Res Rev, May 2005 (May 2005), 25(3):331-42.
Sela S et al., 'Primed Peripheral Polymorphonuclear Leukocyte: A Culprit Underlying Chronic Low-Grade Inflammation and Systemic Oxidative Stress in Chronic Kidney Disease,' J Am Soc Nephrol, Jun. 29, 2005 (Jun. 29, 2005)(ePub), 16(8):2431-8.
Simmons EM et al., 'Plasma Cytokine Levels Predict Mortality in Patients with Acute Renal Failure,' Kidney Int, Apr. 2004 (Apr. 2004), 65(4):1357-65.
Simms MG and Walley KR, 'Activated Macrophages Decreases Rat Cardiac Myocyte Contractility: Importance of ICAM-1-Dependent Adhesion,' Am J Physiol, Jul. 1999 (Jul. 1999), 277(1 Pt 2):H253-60.
Sollevi A, 'Cardiovascular Effects of Adenosine in Man: Possible Clinical Implications,' Prog Neurobiol, 1986 (1986), 27(4):319-49.
Sugi K, 'Filtration Leukocytapheresis Expected to Ulcerative Colitis Treatment,' BIO Clinica 1997 (1997), 12(5):339-42 [Article in Japanese Language].
Sutton SW et al., 'Clinical Benefits of Continuous Leukocyte Filtration During Cardiopulmonary Bypass in Patients Undergoing Valvular Repair or Replacement,' Perfusion, Jan. 2005 (Jan. 2005), 20(1):21-9.
Sutton TA et al., 'Microvascular Endothelial Injury and Dysfunction During Ischemic Acute Renal Failure,' Kidney Int, Nov. 2002 (Nov. 2002), 62(5):1539-49.
Suzuki G et al., 'Effects of Long-Term Monotherapy with Eplerenone, a Novel Aldosterone Blocker, on Progression of Left Ventricular Dysfunction and Remodeling in Dogs with Heart Failure,' Circulation, Dec. 3, 2002 (Dec. 3, 2002), 106(23):2967-72.
Suzuki G et al., 'Effects of the AT1-Receptor Antagonist Eprosartan on the Progression of Left Ventricular Dysfunction in Dogs with Heart Failure,' Br J Pharmacol, Jan. 2003 (Jan. 2003), 138(2):301-9.
Takashi S et al., 'A Peptide Against the N-terminus of Myristoylated Alanine-Rich C Kinase Substrate Inhibits Degranulation of Human Leukocytes in vitro,' Am J Respir Cell Mol Biol, Mar. 16, 2006 (Mar. 16, 2006), 34(6):647-52.

(56) References Cited

OTHER PUBLICATIONS

Tang AT et al., Leukodepletion Reduces Renal Injury in Coronary Revascularization: A Prospective Randomized Study, Ann Thorac Surg, Aug. 2002 (Aug. 2002), 74(2):372-7.

Taylor FB Jr et al., 'Antithrombin-III Prevents the Lethal Effects of *Escherichia coli* Infusion in Baboons,' Circ Shock, Nov. 1988 (Nov. 1988), 26(3):227-35.

Teasdale G and Jennett B, 'Assessment of Coma and Impaired Consciousness. A Practical Scale,' Lancet, Jul. 13, 1974 (Jul. 13, 1974), 2(7872):81-4.

Tevaearai HT et al., 'In situ Control of Cardiotomy Suction Reduces Blood Trauma,' ASAIO J, Sep.-Oct. 1998 (Sep.-Oct. 1998), 44(5):M380-3.

Thakar CV et al., 'Renal Dysfunction and Serious Infection After Open-Heart Surgery,' Kidney Int, Jul. 2003 (Jul. 2003), 64(1):239-46.

Tielemans CL et al., 'Adhesion Molecules and Leukocyte Common Antigen on Monocytes and Granulocytes During Hemodialysis,' Clin Nephrol, Mar. 1993 (Mar. 1993), 39(3):158-65.

Tiranathanagul K et al., 'Bioartificial Kidney in the Treatment of Acute Renal Failure Associated with Sepsis,' Nephrology (Carlton), Aug. 2006 (Aug. 2006), 11(4):285-91.

Tobe SW et al., 'A Novel Regional Citrate Anticoagulation Protocol for CRRT Using Only Commercially Available Solutions,' J Crit Care, Jun. 2003 (Jun. 2003), 18(2):121-9.

Tolwani AJ et al., 'A Practical Citrate Anticoagulation Continuous Venovenous Hemodiafiltration Protocol for Metabolic Control and High Solulte Clearance,' Clin J Am Soc Nephrol, Nov. 23, 2005 (Nov. 23, 2005)(ePub), 1(1):79-87.

Tschesche H et al., 'Inhibition of Degranulation of Polymorphonuclear Leukocytes by Angiogenin and its Tryptic Fragment,' J Biol Chem, Dec. 2, 1994 (Dec. 2, 1994), 269(48):30274-80.

Tumlin J et al., 'Efficacy and Safety of Renal Tubule Cell Therapy for Acute Renal Failure,' J Am Soc Nephrol, Feb. 13, 2008 (Feb. 13, 2008)(ePub), 19(5):1034-40.

Tumlin JA et al., 'A Multi-Center, Randomized, Controlled, Pivotal Study to Assess the Safety and Efficacy of a Selective Cytopheretic Device in Patients with Acute Kidney Injury,' PLoS One, Aug. 5, 2015 (Aug. 5, 2015), 10(8):e0132482.

Tumlin JA et al., 'Effect of the Renal Assist Device (RAD) on Mortality of Dialysis-Dependent Acute Renal Failure: A Randomized, Open-Labeled, Multicenter. Phase II Trial,' J Am Soc Nephrol, 2005 (2005), 16:46A.

Tumlin JA et al., (2011), 'A Multi-Center Pilot Study to Assess the Safety and Efficacy of Selective Cytopheretic Device (SCD) Therapy in Patients with Acute Kidney Injury (AKI),' J Am Soc Nephrol, Abstract TH-OR097, 22:24A (Abstract).

Uchiba M et al., 'Effects of Various Doses of Antithrombin III on Endotoxin-Induced Endothelial Cell Injury and Coagulation Abnormalities in Rats,' Thromb Res, Mar. 1998 (Mar. 1998), 89(5):233-41.

Vincent JL et al., 'The SOFA (Sepsis-Related Organ Failure Assessment) Score to Describe Organ Dysfunction/Failure. On Behalf of the Working Group on Sepsis-Related Problems of the European Society of Intensive Care Medicine,' Intensive Care Med, Jul. 1996 (Jul. 1996), 22(7):707-10.

Vincent JL et al., 'Use of the SOFA Score to Assess the Incidence of Organ Dysfunction/Failure in Intensive Care Units: Results of a Multicenter, Prospective Study. Working Group on "Sepsis-Related Problems" of the European Society on Intensive Care Medicine,' Crit Care Med, Nov. 1998 (Nov. 1998), 26(11):1793-800.

Wan S et al., 'Cytokine Responses to Cardiopulmonary Bypass: Lessons Learned from Cardiac Transplantation,' Ann Thorac Surg, Jan. 1997 (Jan. 1997), 63(1):269-76.

Wan S et al., 'Inflammatory Response to Cardiopulmonary Bypass: Mechanisms Involved and Possible Therapeutic Strategies,' Chest, Sep. 1997 (Sep. 1997), 112(3):676-92.

Warren BL et al., 'Caring for the Critically Ill Patient. High-Dose Antithrombin III in Severe Sepsis: A Randomized Controlled Trial,' JAMA, Oct. 17, 2001 (Oct. 17, 2001), 286(15):1869-78.

Welbourn CR and Young Y, 'Endotoxin, Septic Shock and Acute Lung Injury, Neutrophils, Macrophages and Inflammatory Mediators,' Br J Surg, Oct. 1992 (Oct. 1992), 79(10):998-1003.

Wiegmann TB et al., 'Dialysis Leukopenia, Hypoxemia, and Anaphylatoxin Formation: Effect of Membrane, Bath, and Citrate Anticoagulation,' Am J Kidney Dis, May 1988 (May 1988), 11(5):418-24.

Wiegmann TB et al., 'Long-Term Comparisons of Citrate and Heparin as Anticoagulants for Hemodialysis,' Am J Kidney Dis, May 1987 (May 1987), 9(5):430-5.

Williams et al., 'RAD-002 Study Investigators. Renal Bioreplacement Therapy (RBT) Reduces Mortality in ICU Patients with Acute Renal Failure (ARF),' J Am Soc Nephrol, 2006 (2006), 17:49A.

Wong K and Li X, 'Nitirc Oxide Infusion Alleviates Cellular Activation During Preparation, Leukofiltration and Storage of Platelets,' Transfus Apher Sci, Feb. 2004 (Feb. 2004), 30(1):29-39.

Written Opinion of the International Search Authority (Form ISA/237) for International Application PCT/US2012/059615 dated Jun. 17, 2013 (8 pages).

Xue JL et al., 'Forecast of the Number of Patients with End-Stage Renal Disease in the United States to the Year 2010,' J Am Soc Nephrol, Dec. 2001 (Dec. 2001), 12(12):2753-8.

Yamaji K et al., 'Current Topics on Cytapheresis Technologies,' Ther Apher, Aug. 2001 (Aug. 2001), 5(4):287-92.

Yevzlin AS and Humes HD, 'Cell Therapy, Advanced Materials, and New Approaches to Acute Kidney Injury,' Hosp Pract (1995), Dec. 2009 (Dec. 2009), 37(1):137-43.

Ympa YP et al., 'Has Mortality from Acute Renal Failure Decreased? A Systematic Review of the Literature,' Am J Med, Aug. 2005 (Aug. 2005), 118(8):827-32.

Yoon JW et al., 'Spontaneous Leukocyte Activation and Oxygen-Free Radical Generation in End-Stage Renal Disease,' Kidney Int, Nov. 15, 2006 (Nov. 15, 2006)(ePub), 71(2):167-72.

Zarbock A et al., 'Complete Reversal of Acid-Induced Acute Lung Injury by Blocking of Platelet-Neutrophil Aggregation,' J Clin Invest, Dec. 2006 (Dec. 2006), 116(12):3211-9.

Zehr KJ et al., 'Platelet Activating Factor Inhibition Reduces Lung Injury After Cardiopulmonary Bypass,' Ann Thorac Surg, Feb. 1995 (Feb. 1995), 59(2):328-35.

Zelen M, 'The Randomization and Stratification of Patients to Clinical Trials,' J Chronic Dis, Sep. 1974 (Sep. 1974), 27(7-8):365-75.

Zimmermann J et al., 'Inflammation Enhances Cardiovascular Risk and Mortality in Hemodialysis Patients,' Kidney Int, Feb. 1999 (Feb. 1999), 55(2):648-58.

The English translation of Sugi "Sugi K, 'Filtration Leukocytapheresis Expected to Ulcerative Colitis Treatment,' BIO Clinica 1997 (1997), 12(5):339-42 [English Language Translation]".

U.S. Appl. No. 12/201,576, filed Aug. 29, 2008; now U.S. Pat. No. 8,251,941 on Aug. 28, 2012.

U.S. Appl. No. 12/827,594, filed Jun. 30, 2010; now U.S. Pat. No. 8,425,445 on Apr. 23, 2013.

U.S. Appl. No. 12/827,601, filed Jun. 30, 2010; now U.S. Pat. No. 8,430,832 on Apr. 30, 2013.

U.S. Appl. No. 12/827,606, filed Jun. 30, 2010; now U.S. Pat. No. 8,409,126 on Apr. 2, 2013.

U.S. Appl. No. 12/827,609, filed Jun. 30, 2010; now U.S. Pat. No. 8,425,446 on Apr. 23, 2013.

U.S. Appl. No. 13/087,995, filed Apr. 15, 2011; now U.S. Pat. No. 9,341,626 on May 17, 2016.

U.S. Appl. No. 13/531,870, filed Jun. 25, 2012; now U.S. Pat. No. 9,128,093 on Sep. 8, 2015.

U.S. Appl. No. 15/294,229, filed Oct. 14, 2016, now abandoned.

U.S. Appl. No. 16/359,300, filed Mar. 20, 2019.

U.S. Appl. No. 13/531,872, filed Jun. 25, 2012; now U.S. Pat. No. 9,498,566 on Nov. 22, 2016.

U.S. Appl. No. 13/593,127, filed Jun. 23, 2012, now abandoned.

U.S. Appl. No. 13/593,169, filed Aug. 23, 2012; now U.S. Pat. No. 8,425,447 on Apr. 23, 2013.

U.S. Appl. No. 13/878,954, filed Jul. 17, 2013, now abandoned.

U.S. Appl. No. 14/252,305, filed Apr. 14, 2014, now abandoned.

U.S. Appl. No. 15/628,071, filed Jun. 20, 2017, now abandoned.

(56) References Cited

OTHER PUBLICATIONS

U.S. Appl. No. 15/664,884, filed Jul. 31, 2017, now U.S. Pat. No. 11,118,162 on Jul. 31, 2017.
U.S. Appl. No. 17/628,071, filed Sep. 13, 2021.
U.S. Appl. No. 14/327,145, filed Jul. 9, 2014, now abandoned.
U.S. Appl. No. 115/492,518, filed Apr. 20, 2017, now U.S. Pat. No. 10,722,637.

* cited by examiner

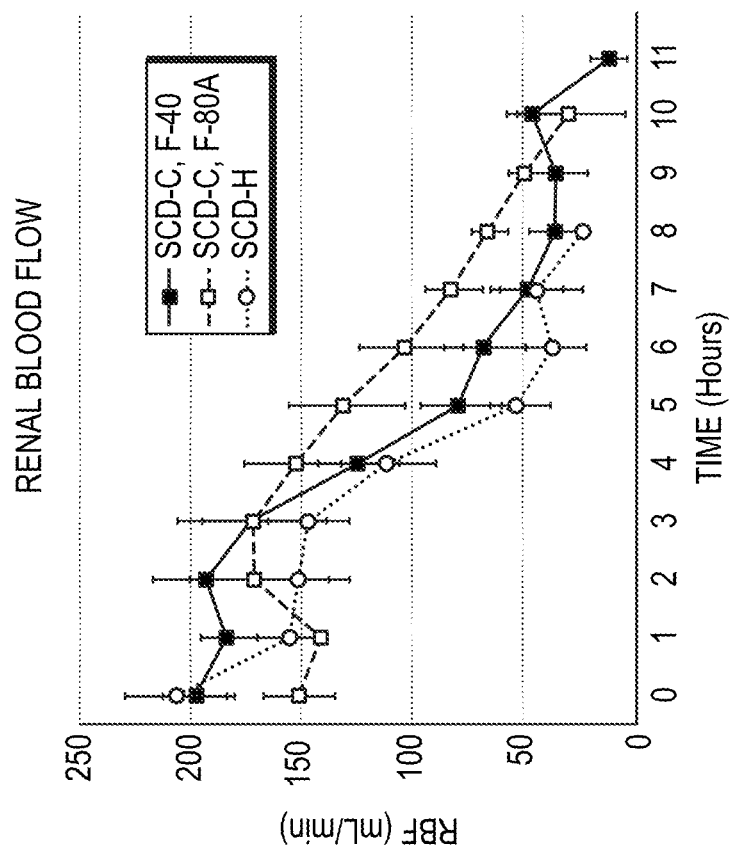
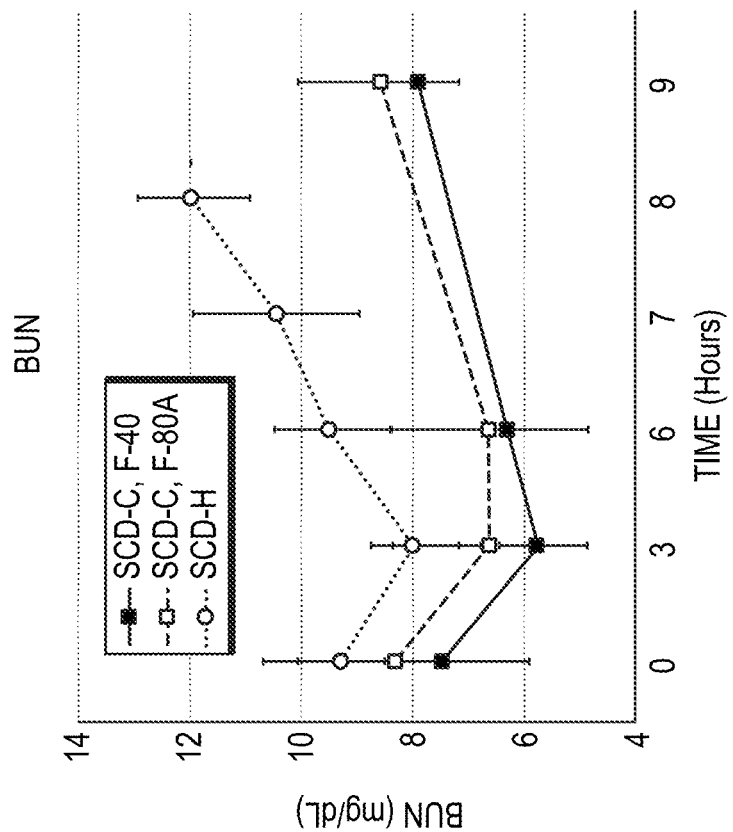
FIG. 6A
FIG. 6B

IMPACT OF SCD-C vs. SCD-H ON SURVIVAL TIME IN THE SEPTIC PIG, $p<0.005$ (F-40) AND $<0.0004$ (F-80A)

FIG. 9A
FIG. 9B
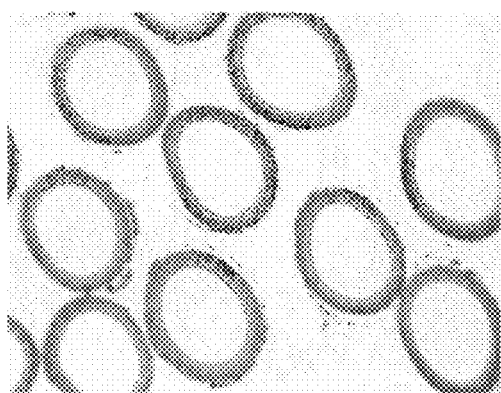
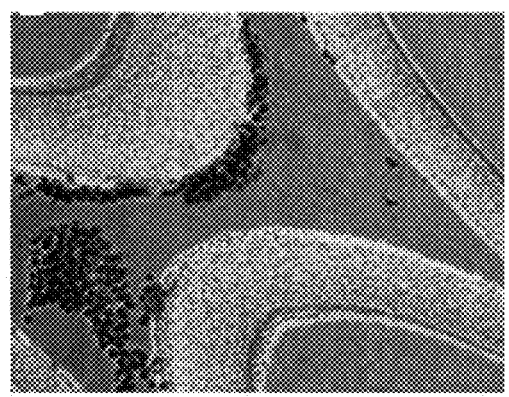
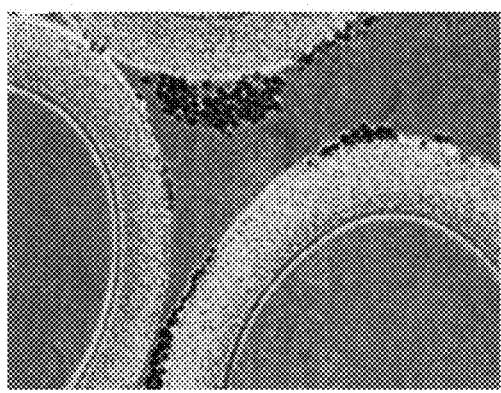
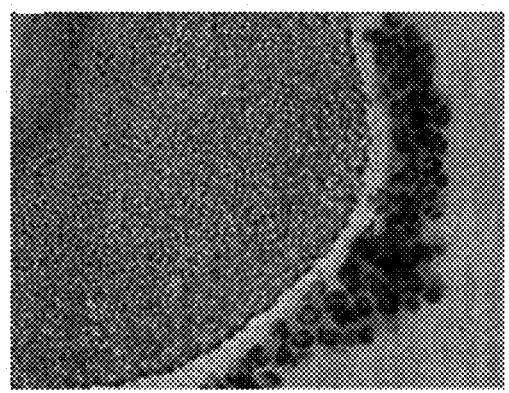
FIG. 9C
FIG. 9D

ADHERENT CELLS ELUTED FROM SCD-C AND SCD-H CARTRIDGES AFTER SEPTIC PIG STUDY END POINT.

STIMULATED MNC IL-8 SECRETION.

STIMULATED MNC TNF-a SECRETION.

LUNG TISSUE LEUKOCYTE AGGREGATION EXPRESSED AS # OF CD11b POSITIVE CELLS/# OF DAPI STAINED NUCLEI AFTER IHC STAINING, $P < 0.01$ FOR ALL SCD-C GROUPS COMPARED TO THE SCD-H GROUP.

CARTRIDGE AND METHOD FOR INCREASING MYOCARDIAL FUNCTION

CROSS-REFERENCE TO RELATED APPLICATIONS

This application is a continuation of U.S. patent application Ser. No. 15/492,518, filed Apr. 20, 2017, now U.S. Pat. No. 10,722,637, which is a continuation of U.S. patent application Ser. No. 14/327,145, filed Jul. 9, 2014, which is a continuation of International Patent Application No. PCT/US2012/059615, filed Oct. 10, 2012, which claims priority to and the benefit of U.S. Provisional Patent Application No. 61/584,337, filed Jan. 9, 2012, the contents of each of which are incorporated by reference herein.

STATEMENT REGARDING FEDERALLY SPONSORED RESEARCH

This invention was made with government support under grant number W81XWH-10-2-0137, awarded by the US Army Medical Research and Material Command. The government has certain rights in the invention.

FIELD OF THE INVENTION

The present invention relates to cartridges, systems, and methods for treating and/or preventing inflammatory myocardial conditions in a subject. More particularly, the present invention relates to cartridges and systems for sequestering and reducing the inflammatory activity of cells associated with myocardial inflammation, such as leukocytes and platelets, and to related methods for sequestering and reducing the inflammatory activity of such cells.

BACKGROUND

Various medical conditions are caused, exacerbated, and/or characterized by unwanted inflammation. For example, chronic inflammation is central to the development of a variety of acute organ failures, including those involving the heart, kidney, lung, and brain. Chronic inflammation is also a major contributing factor to chronic organ dysfunction, including those involving the heart and kidney as well as diabetes type 2. Several of these conditions, such as, for example, chronic heart failure (CHF) and acute decompensated heart failure (ADHF), through abnormal or excessive chronic activation of the immune system, may result in life threatening myocardial dysfunction.

Certain cell types are critical to the dysfunction of the cardiovascular and immune systems. For example, leukocytes such as neutrophils contribute to the pathogenesis and progression of various inflammatory conditions, including systemic inflammatory response syndrome (SIRS), sepsis, ischemia/reperfusion injury, acute respiratory distress syndrome (ARDS), CHF, and ADHF (see, e.g., Kaneider et al. (2006) FEBS J 273:4416-4424; Maroszynska et al. (2000) ANN. TRANSPLANT. 5(4):5-11). Other types of leukocytes, such as monocytes and tissue macrophages, have been identified as critical sources of systemic inflammation in CHF and cause a decrease in cardiac myocyte contractility (see, e.g., Conraads et al. (2005) J. HEART LUNG TRANSPLANT. 24(7): 854-59; Simms et al. (1999) AM. J. PHYSIOL. 277: H253-60; Conraads et al. (2005) J. HEART LUNG TRANSPLANT. 24(7): 854-9; Simms et al. (1999) AM. J. PHYSIOL. 277: H253-60). In addition, activated platelets enhance leukocyte adhesion and promote leukocyte activation. While inflammation and a systemic immune response can be beneficial in certain circumstances, they can also be fatal.

Inflammatory injury in organs can result in microvascular damage induced by leukocyte activation and aggregation, as well as platelet activation and aggregation. These activated cells can contribute to microvascular stasis and reperfusion injury by releasing toxic compounds into a patient's tissue. Activated leukocytes additionally cause damage by extravasating across the endothelium into the tissue, where they release toxic agents normally intended to destroy invading microbes or clear out necrotic debris. Further, the interaction of activate leukocytes and the endothelium can lead to increased vascular permeability with fluid leakage from the intravascular space to the tissue interstitium with resulting hypovolemia, hypotension, and cardiovascular instability. Activated platelets additionally cause damage by enhancing the activation and endothelial transmigration of leukocytes. When these processes are not controlled, they can lead to tissue injury and death.

Cardiovascular disease is the leading cause of mortality in the United States, accounting for 45% of all deaths. Furthermore, in the United States, CHF affects 5 million people, with over 0.5 million new cases identified annually with direct hospital costs exceeding $30 billion (see, e.g., Association (2006) HEART DISEASE AND STROKE FACTS; Association (2002) 2003 HEART AND STROKE STATISTICAL UPDATE; Fonarow et al. (2003) 4: p. S21-30). In severe CHF, annual mortality rates can be as high as 50%. Currently, treatment of CHF generally involves a ventricular assist device or orthotropic heart transplant. Over the past decade, a number of therapeutic agents for treating CHF have been clinically tested in large prospective trials. Endothelin receptor antagonists, adenosine A1-receptor antagonist, and vasopressin V2 receptor blocker have all failed to prove clinical efficacy (see, e.g., McMurray et al. (2007) JAMA 298(17): 2009-19; Massie et al. (2010) N. ENGL. J. MED. 363(15): 1419-28; Konstam et al. (2007) JAMA 297(12): 1319-31). The myocardial calcium sensitizing agent (levosimendan) and the vasodilatory recombinant B-type natriuretic peptide (niseritide) have also failed to meet clinical efficacy end points with an increase in risks of arrhythmias or hypotension ((see, e.g., Cohn et al. (1998) N. ENGL. J. MED. 339(25): 1810-6; Mebazza et al. (2007) JAMA 297(17): 1883-91; O'Connor et al. (2011) N. ENGL. J. MED. 365(1): 32-43).

Acute decompensated heart failure (ADHF) accounts for almost one million hospitalizations per year, and rehospitalization within six months is as high as 50%. The annual mortality rate in patients frequently hospitalized with ADHF approaches 50%. Current therapeutic approaches for treating patients with ADHF focus on relieving these patients of the congestive symptoms of heart failure, usually with diuretics. However, such an approach results in, and is limited by further declines in renal functions.

Accordingly, there remains a need for improved treatments of inflammatory conditions that affect myocardial functions, such as chronic heart failure and acute decompensated heart failure.

SUMMARY OF THE INVENTION

Inflammatory conditions often arise from the activation of cells associated with inflammation, such as leukocytes and platelets. The present invention relates to methods and cytopheretic cartridges for use in treating and/or preventing inflammatory conditions that affect various myocardial functions. The methods and/or cartridges of the invention extracorporeally sequester leukocytes and/or platelets and inhibit or deactivate their inflammatory action. For example, these cells can be deactivated and/or their release of pro-inflammatory substances can be inhibited.

In a first aspect, the invention provides a method of increasing myocardial function in a subject with chronic heart failure. The method comprises the step of (a) extracorporeally sequestering activated leukocytes and/or activated platelets present in a body fluid (for example, blood) of the subject in a cartridge comprising (i) a rigid housing defining an inner volume (IV), a fluid inlet port and a fluid outlet port, wherein the inner volume is in fluid flow communication with the fluid inlet port and the fluid outlet port, and (ii) a solid support disposed within the housing and defining a fluid contacting surface with a surface area (SA) capable of sequestering activated leukocytes and/or activated platelets, if present in a body fluid entering the housing via the fluid inlet port. The body fluid (for example, blood) is introduced into the housing via the fluid inlet port under conditions that permit sequestration of the activated leukocytes and/or activated platelets on the fluid contacting surface of the solid support. The method also comprises the step of (b) treating the sequestered leukocytes and/or platelets to inhibit release of a pro-inflammatory substance or to deactivate the leukocytes and/or platelets thereby to increase myocardial function of the subject when compared to the myocardial function of the subject prior to treatment. The increase in myocardial function can be one or more functions selected from the group consisting of left ventricular ejection fraction, cardiac output, systemic vascular resistance, left ventricular stroke volume, aortic pressure, left ventricular pressure, peak rate of change of left ventricular pressure during isovolumic contraction and relaxation, left ventricular end-diastolic pressure, myocardial oxygen consumption, and coronary flow reserve.

The first aspect of the invention can have any one or more of the following features or embodiments described herein.

In certain embodiments, the SA/IV ratio of the cartridge provided in step (a) is greater than 25 cm$^{-1}$, or is in the range of 25 cm$^{-1}$ to 2,000 cm$^{-1}$, or is no greater than 80 cm$^{-1}$. The solid support can be disposed within the housing at a packing density in the range from 20% to 65%.

In certain embodiments the solid support can be defined by one or more fibers (for example, fluid permeable fibers (for example, permeable hollow fibers) or fluid impermeable fibers (for example, solid fibers)), one or more planar support members, or any combination thereof. The solid support can comprise one or more membranes. The solid support can be substantially parallel to the direction of fluid flow within the cartridge.

In certain embodiments, the SA of the cartridge provided in step (a) is in the range of from 0.1 m$^2$ to 10.0 m$^2$, or in the range of from 0.1 m$^2$ to 5.0 m$^2$. In certain embodiments, the IV is less than 300 cm$^3$, less than 150 cm$^3$, is in the range of from 10 cm$^3$ to 150 cm$^3$, is in the range of from 75 cm$^3$ to 150 cm$^3$ or is in the range of from 15 cm$^3$ to 120 cm$^3$.

In certain embodiments, the method optionally further comprises permitting the body fluid to exit the cartridge via the fluid outlet port at a flow rate in the range of 10 cm$^3$/minute to 8,000 cm$^3$/minute.

In step (b), the leukocytes and/or platelets can be treated with an immunosuppressant agent, a serine leukocyte inhibitor, nitric oxide, a polymorphonuclear leukocyte inhibitor factor, a secretory leukocyte inhibitor, or a calcium chelating agent, wherein the calcium chelating agent is one or more of the group consisting of citrate, sodium hexametaphosphate, ethylene diamine tetra-acetic acid (EDTA), triethylene tetramine, diethylene triamine, o-phenanthroline, and oxalic acid. In a preferred embodiment, in step (b), the leukocytes and/or platelets are treated with a calcium chelating agent, for example, citrate. Each of the foregoing agents, including the calcium chelating agent, can be introduced into the body fluid of the subject prior to, during, or after step (a).

In certain embodiments, the leukocytes and/or platelets are treated over a period of at least 2 hours, at least 4 hours, at least 6 hours, at least 8 hours, or at least 12 hours, or over a period of 2 to 48 hours, 2 to 24 hours, 2 to 12 hours, 4 to 48 hours, 4 to 24 hours, or 4 to 12 hours.

The subject may have myocardial dysfunction secondary to inflammatory cell penetration of heart tissue, and/or may have received a heart transplant. In certain embodiments, the increased myocardial function is maintained for at least 6 hours or at least 24 hours after termination of the treatment in step (b).

In a second aspect, the invention provides a method of increasing myocardial function in a subject with chronic heart failure. The method comprises: (a) extracorporeally sequestering activated leukocytes and/or activated platelets present in a body fluid (for example, blood) of the subject; and (b) treating the sequestered leukocytes and/or platelets to inhibit release of a pro-inflammatory substance or to deactivate the leukocytes and/or platelets thereby to increase myocardial function of the subject when compared to the myocardial function of the subject prior to treatment. The myocardial function can be selected from the group consisting of left ventricular ejection fraction, cardiac output, systemic vascular resistance, left ventricular stroke volume, aortic pressure, left ventricular pressure, peak rate of change of left ventricular pressure during isovolumic contraction and relaxation, left ventricular end-diastolic pressure, myocardial oxygen consumption, and coronary flow reserve.

In a third aspect, the invention provides a method of increasing myocardial function in a subject with acute decompensated heart failure (ADHF). The method comprises: (a) extracorporeally sequestering activated leukocytes and/or activated platelets present in a body fluid (for example, blood) of the subject; and (b) treating the sequestered leukocytes and/or platelets to inhibit release of a pro-inflammatory substance or to deactivate the leukocytes and/or platelets thereby to increase myocardial function of the subject when compared to the myocardial function of the subject prior to treatment.

The second and third aspects of the invention can have any one or more of the following features or embodiments described herein.

For example, in each aspect the subject can have myocardial dysfunction secondary to inflammatory cell penetration of heart tissue, and/or may have received a heart transplant. In step (b), the leukocytes and/or platelets are treated with an immunosuppressant agent, a serine leukocyte inhibitor, nitric oxide, a polymorphonuclear leukocyte inhibitor factor, a secretory leukocyte inhibitor, or a calcium chelating agent, wherein the calcium chelating agent is one or more of the group consisting of citrate, sodium hexametaphosphate, ethylene diamine tetra-acetic acid (EDTA), triethylene tetramine, diethylene triamine, o-phenanthroline, and oxalic acid. In a preferred embodiment, in step (b), the leukocytes and/or platelets are treated with a calcium chelating agent, for example, citrate. Each of the foregoing agents, including the calcium chelating agent, can be introduced into the body fluid of the subject prior to or after step (a).

In each aspect, the leukocytes and/or platelets from the subject are treated over a period of at least 2 hours, at least 4 hours, at least 6 hours, at least 8 hours, or at least 12 hours, or are treated over a period of 2 to 48 hours, 2 to 24 hours, 2 to 12 hours, 4 to 48 hours, 4 to 24 hours, or 4 to 12 hours.

The myocardial function improved by the treatment can be one or more of the myocardial functions selected from the group consisting of left ventricular ejection fraction, cardiac output, systemic vascular resistance, left ventricular stroke volume, aortic pressure, left ventricular pressure, peak rate of change of left ventricular pressure during isovolumic contraction and relaxation, left ventricular end-diastolic pressure, myocardial oxygen consumption, and coronary flow reserve. The increase in myocardial function is maintained for at least 6 hours, or at least 24 hours after termination of the treatment in step (b).

In step (b), the activated leukocytes are sequestered (for example, bound) by introducing the body fluid into a cartridge comprising (i) a rigid housing defining an inner volume (IV), a fluid inlet port and a fluid outlet port, wherein the inner volume is in fluid flow communication with the fluid inlet port and the fluid outlet port, and (ii) a solid support disposed within the housing and defining a fluid contacting surface with a surface area (SA) capable of sequestering activated leukocytes and/or platelets, if present in a body fluid entering the housing via the fluid inlet port. The body fluid is introduced into the housing via the fluid inlet port under conditions that permit sequestration (for example, binding) of the activated leukocytes and/or platelets on the fluid contacting surface of the solid support. It is understood that, under certain circumstances, the activated leukocytes and platelets bind preferentially to the fluid contacting surface of the solid support relative to unactivated or deactivated leukocytes or platelets.

In certain embodiments, the SA/IV ratio of the cartridge provided in step (a) is greater than 25 $cm^{-1}$, greater than 80 $cm^{-1}$, or greater than 150 $cm^{-1}$, or is in the range of from 25 $cm^{-1}$ to 1,500 $cm^{-1}$, or is in the range of from 80 $cm^{-1}$ to 1,500 $cm^{-1}$. In other embodiments, the SA/IV ratio is no greater than 80 $cm^{-1}$. The solid support can be disposed within the housing at a packing density in the range from 20% to 65%.

In certain embodiments the solid support can be defined by one or more fibers (for example, fluid permeable fibers (for example, permeable hollow fibers) or fluid impermeable fibers (for example, solid fibers)), one or more planar support members, or any combination thereof. The solid support can comprise one or more membranes. The solid support can be substantially parallel to the direction of fluid flow within the cartridge.

The SA of the cartridge provided in step (a) can be in the range of from 0.1 $m^2$ to 10.0 $m^2$, in the range of from 0.1 $m^2$ to 5.0 $m^2$. Furthermore, the inner volume of the cartridge provided in step (a) is less than 300 $cm^3$, less than 150 $cm^3$, or is in the range of from 10 $cm^3$ to 150 $cm^3$, in the range of from 75 $cm^3$ to 150 $cm^3$, or in the range of 15 $cm^3$ to 120 $cm^3$. In certain embodiments, the method further comprises permitting the body fluid to exit the cartridge via the fluid outlet port at a flow rate in the range of 10 $cm^3$/minute to 8,000 $cm^3$/minute.

In a fourth aspect, the invention provides a method of treating a subject having or at risk of developing an inflammatory condition associated with acute decompensated heart failure (ADHF). The method comprises: (a) providing a cartridge comprising (i) a rigid housing defining an inner volume (IV), a fluid inlet port and a fluid outlet port, wherein the inner volume is in fluid flow communication with the fluid inlet port and the fluid outlet port; and (ii) a solid support disposed within the housing and defining a fluid contacting surface with a surface area (SA) capable of sequestering an activated leukocyte, if present in a body fluid entering the housing via the fluid inlet port; and (b) introducing a body fluid from a subject into the housing via the fluid inlet port under conditions that permit sequestration of an activated leukocyte and/or an activated platelet on the fluid contacting surface of the solid support. The method optionally further comprises the step of (c) treating the leukocyte and/or platelet sequestered in step (b) to reduce the risk of developing inflammation associated with the ADHF or to alleviate inflammation associated with the ADHF.

In a fifth aspect, the invention provides a method of treating a subject having or at risk of developing an inflammatory condition, wherein the inflammatory condition is chronic heart failure (CHF). The method comprises: (a) providing a cartridge comprising (i) a rigid housing defining an inner volume (IV), a fluid inlet port and a fluid outlet port, wherein the inner volume is in fluid flow communication with the fluid inlet port and the fluid outlet port; and (ii) a fluid permeable solid support disposed within the housing and defining a fluid contacting surface with a surface area (SA) capable of sequestering an activated leukocyte, if present in a body fluid entering the housing via the fluid inlet port, wherein the SA/IV ratio is no greater than 80 $cm^{-1}$; and (b) introducing a body fluid from a subject into the housing via the fluid inlet port under conditions that permit sequestration of an activated leukocyte and/or an activated platelet on the fluid contacting surface of the solid support. The method optionally further includes the step of (c) treating the leukocyte and/or platelet sequestered in step (b) (for example, with a calcium chelator) to reduce the risk of developing inflammation associated with the inflammatory condition or to alleviate inflammation associated with the inflammatory condition.

The fourth and fifth aspects of the invention can have one or more of the following features or embodiments described herein.

For example, in certain embodiments, the leukocyte and/or platelet is sequestered for a time sufficient to deactivate the leukocyte and/or the platelet, for example, at least one minute. Furthermore, the method optionally further includes the step of returning the leukocyte and/or the platelet produced in step (c) back to the subject.

In certain embodiments, the SA/IV ratio of the cartridge provided in step (a) is greater than 80 $cm^{-1}$, or is greater than 150 $cm^{-1}$ or can be in the range of from 80 $cm^{-1}$ to 1,500 $cm^{-1}$, or in the range of from 150 $cm^{-1}$ to 1,500 $cm^{-1}$. In certain embodiments the solid support can be defined by one or more fibers (for example, fluid permeable fibers (for example, permeable hollow fibers) or fluid impermeable fibers (for example, solid fibers)), one or more planar support members, or any combination thereof. The solid support can comprise one or more membranes. The solid support can be substantially parallel to the direction of fluid flow within the cartridge.

In certain embodiments, the SA of the cartridge provided in step (a) is in the range of from 0.1 $m^2$ to 10.0 $m^2$, or in the range of from 0.1 $m^2$ to 5.0 $m^2$, or is in the range of from 0.1 $m^2$ to 0.4 $m^2$, from 0.4 $m^2$ to 0.8 $m^2$, from 0.8 $m^2$ to 1.2 $m^2$, from 1.2 $m^2$ to 1.6 $m^2$, from 1.6 $m^2$ to 2.0 $m^2$, from 2.0 $m^2$ to 2.4 $m^2$, from 2.4 $m^2$ to 2.8 $m^2$, from 2.8 $m^2$ to 3.2 $m^2$, from 3.2 $m^2$ to 3.6 $m^2$, from 3.6 $m^2$ to 4.0 $m^2$, from 4.0 $m^2$ to 4.4 $m^2$, from 4.4 $m^2$ to 4.8 $m^2$, from 4.8 $m^2$ to 5.2 $m^2$, from 5.2 $m^2$ to 5.6 $m^2$, from 5.6 $m^2$ to 6.0 $m^2$, from 6.0 $m^2$ to 6.4 $m^2$, from 6.4 $m^2$ to 6.8 $m^2$, from 6.8 $m^2$ to 7.2 $m^2$, from 7.2 $m^2$ to 7.6 $m^2$, from 7.6 $m^2$ to 8.0 $m^2$, from 8.0 $m^2$ to 8.4 $m^2$, from 8.4 m² to 8.8 m², from 8.8 m² to 9.2 m², from 9.2 m² to 9.6 m², or from 9.6 m² to 10.0 m².

In certain embodiments, the inner volume of the cartridge provided in step (a) is less than 150 cm³, or is in the range of from 10 cm³ to 150 cm³, or is in the range of from 75 cm³ to 150 cm³, or is in the range of from 15 cm³ to 120 cm³, or is in the range of from 20 cm³ to 80 cm³.

In certain embodiments, the method further comprises the step of permitting the body fluid to exit the cartridge via the fluid outlet port at a flow rate in the range of 10 cm³/minute to 8,000 cm³/minute, or in the range of 50 cm³/minute to 8,000 cm³/minute. Furthermore, the method optionally further comprises the step of measuring the myocardial function of the subject prior to step (a) and/or after step (b).

In each of the foregoing aspects (including all five aspects of the invention) and embodiments, the leukocyte and/or platelet can be sequestered (for example, bound) for a time (e.g., at least one second, at least one minute, at least five minutes, at least fifteen minutes, or at least an hour) sufficient to inhibit the release of the pro-inflammatory substance or to deactivate the leukocyte and/or the platelet. The activated leukocytes and/or activated platelets bind to a fluid contacting surface of the solid support. Under certain circumstances, the activated leukocytes and/or activated platelets bind preferentially to the fluid contacting surface of the solid support relative to unactivated or deactivated leukocytes and/or platelets.

In another aspect, the invention provides a cartridge for use in a method of improving myocardial function in a subject with chronic heart failure (CHF) or acute decompensated heart failure (ADHF). The cartridge comprises (i) a rigid housing defining an inner volume (IV), a fluid inlet port and a fluid outlet port, wherein the inner volume is in fluid flow communication with the fluid inlet port and the fluid outlet port, and (ii) a solid support disposed within the housing in fluid flow communication with the inner volume and defining a fluid contacting surface with a surface area (SA) configured for sequestering activated leukocytes and/or platelets, if present in a body fluid entering the housing via the fluid inlet port.

In certain embodiments, the cartridge has a SA to IV ratio in the range of 25 cm⁻¹ to 2,000 cm⁻¹, or a SA/IV ratio of greater than 80 cm⁻¹, or a SA/IV ratio of no greater than 80 cm⁻¹. The cartridge can be disposed within sterile packaging, for example, where the sterile packaging comprises plastic packaging. The cartridge optionally further comprises a label disposed on an outer surface of the rigid housing. The cartridge optionally further comprises a cap sealing the fluid inlet port and/or the fluid outlet port. The surface area configured for sequestering activated leukocytes and/or platelets binds the activated leukocytes and/or platelets, optionally preferentially binds the activated leukocytes and/or platelets relative to unactivated or deactivated leukocytes or platelets. It is understood that the cartridge can be used in any of the methods described herein.

In another aspect, the invention provides a calcium chelating agent for use in a method of treating chronic heart failure or acute decompensated heart failure in a subject in need thereof, wherein the method of treating comprises administering the calcium chelating agent to extracorporeally sequestered activated leukocytes and/or activated platelets wherein the activated leukocytes and/or activated platelets are sequestered in any of the cartridges and methods using cartridges described herein.

BRIEF DESCRIPTION OF THE DRAWINGS

The foregoing aspects and embodiments of the invention may be more fully understood by reference to the following detailed description and claims.

In FIG. 3A the circuit comprises a recirculation loop and in FIG. 3B, the fluid circuit lacks a recirculation loop.

FIGS. 6A-D are graphical depictions of changes in renal parameters of subjects with sepsis treated with an F-40 SCD device in the presence of heparin (SCD-H); an F-40 SCD device in the presence of citrate (SCD-C; F-40); or an F-80A SCD device in the presence of citrate (SCD-C; F-80A). Results are shown for blood urea nitrogen (BUN) (FIG. 6A); renal blood flow (FIG. 6B); creatinine (FIG. 6C); and cumulated urine output (FIG. 6D).

FIGS. 9A-D re a series of light microscopy photographs showing leukocyte attachment and aggregation along the outer surface of SCD membranes.

DETAILED DESCRIPTION

Figure 1A:
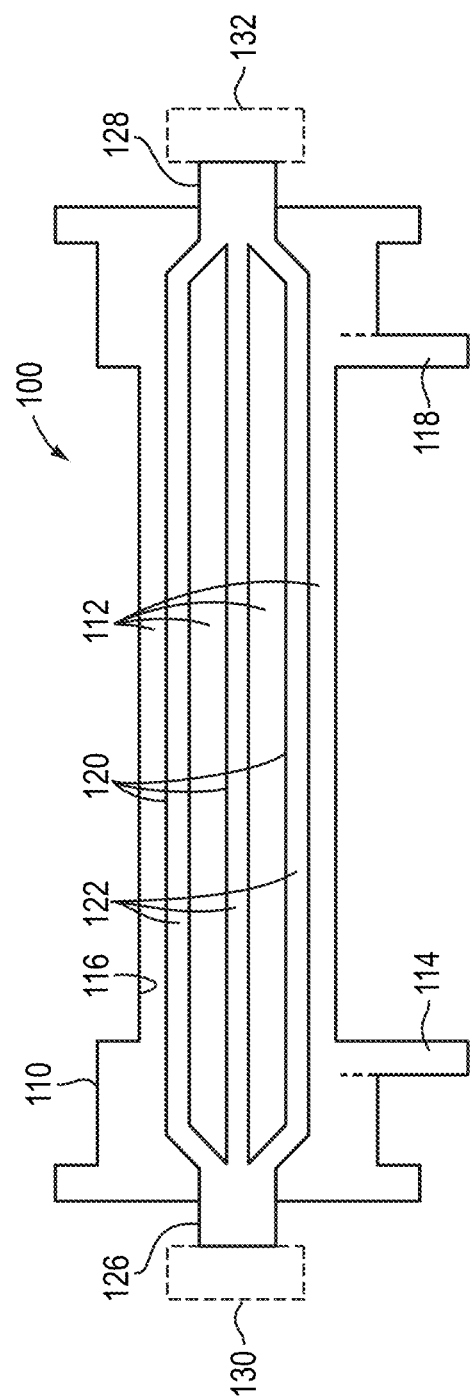
FIG. 1A is a schematic, cross-sectional representation of an exemplary SCD cartridge containing a plurality of hollow fibers.

Cells associated with inflammation, such as leukocytes (or white blood cells) and platelets, normally defend the body against infection and injury. However, during many disease states and medical procedures, these cells can become activated, which in turn can produce undesirable immune and inflammatory responses that can be fatal. It is understood that devices, referred to as selective cytopheretic devices, that extracorporeally sequester leukocytes and/or platelets and then inhibit their inflammatory actions can be useful in the prevention or treatment of a variety of inflammatory conditions, in particular inflammatory conditions mediated or facilitated by activated leukocytes and/or platelets. U.S. Pat. No. 8,251,941 describes exemplary selective cytopheretic devices and their use in the prevention and/or treatment of certain inflammatory conditions.

It has now been discovered that cytopheretic devices can also be useful in increasing cardiac function, for example, left ventricular ejection fraction, cardiac output, systemic vascular resistance, etc., in subjects having or at risk of having chronic heart failure (CHF) and acute decompensated heart failure (ADHF). The use of cytopheretic devices, such as those, described herein may be useful in the treatment of such disorders, especially in situations where drug based therapies (for example, nesiritide and levosimendan, which have been developed for the treatment of chronic heart failure) have heretofore been unsuccessful.

As used herein, the term "cytopheresis" or "selective cytopheresis" refers to the sequestration of certain cells, for example, leukocytes (e.g., activated leukocytes) or platelets (e.g., activated platelets) from a body fluid, for example, blood. The sequestered cells can be deactivated and/or the release of the pro-inflammatory substance from such cells can be inhibited. It should be understood that such deactivation and/or inhibition can occur before, during, and/or after sequestration (e.g., the binding to a fluid contacting surface of a solid support). In a specific embodiment, selective cytopheresis refers to the sequestration of leukocytes (e.g., activated leukocytes) and/or platelets (e.g., activated platelets) from blood. The term "blood" refers to any aspect of blood, for example, whole blood, treated blood, filtered blood, or any liquid derived from blood, for example, serum or plasma.

The terms, "selective cytopheresis device," "selective cytopheretic device," "selective cytopheresis inhibitory device," and "SCD" each refer to a device that facilitates or is capable of facilitating cytopheresis. Such a device can also facilitate deactivation and/or inhibit the release of pro-inflammatory substances from such cells before, during, and/or after sequestration. The SCD includes one or more SCD cartridges that facilitate selective cytopheresis. While the discussion in the sections that follow generally describe sequestration and inhibition and/or deactivation of a particular cell type (e.g., leukocytes), it is understood that the same principles apply to the sequestration and inhibition and/or deactivation of other cell types associated with inflammation (e.g., platelets, such as activated platelets).

An "activated leukocyte" is understood to mean a leukocyte that, in response to a challenge, for example, when exposed to an endotoxin (e.g., lipopolysaccharide), has an enhanced ability to elicit an immune response relative to a leukocyte that has not been challenged. For example, an activated neutrophil (PMN), is a neutrophil that, in response to a challenge, for example, when exposed to an endotoxin (e.g., lipopolysaccharide), has an enhanced ability to migrate, phagocytose, and produce an oxidative burst response relative to a neutrophil that has not been challenged. Activation can also be determined via an up-regulation of cell surface CD11b. An activated monocyte is a monocyte that, in response to a challenge, for example, when exposed to an endotoxin (e.g., lipopolysaccharide), has an enhanced ability to release cytokines relative to a monocyte that has not been challenged. An "activated platelet" is understood to mean a platelet that, in response to a challenge, for example, when exposed to an endotoxin (e.g., lipopolysaccharide), becomes adherent to other platelets, to leukocytes, and to certain proteins, for example, coagulation factors. Platelet activation can be quantified by determining the percentage of circulating monocytes that have platelets adhered to their cell surface. Activated leukocytes also include primed leukocytes. For example, a primed neutrophil (PMN), is a neutrophil that, in response to a challenge, for example, when exposed to an endotoxin (e.g., lipopolysaccharide), has an enhanced ability to undergo an oxidative burst response relative to a neutrophil that has not been challenged.

1. Indications

The SCD cartridges, circuits incorporating the SCD cartridges, and methods of the present invention can be used for treating and/or preventing a number of heart or cardiovascular conditions that are associated with inflammation or an inflammatory condition. In particular the SCD cartridges, circuits incorporating the SCD cartridges, and methods of the present invention can be used for treating and/or preventing a number of heart or cardiovascular conditions where a subject is experiencing myocardial dysfunction secondary to inflammatory cell penetration of heart tissue, for example, myocardial tissue. As used herein, the term "subject" refers to any animal (e.g., a mammal), including, but not limited to, a human (e.g., a patient) or a non-human mammal, for example, a non-human primate or other experimental animal, farm animal, companion animal, or the like, which is to be the recipient of a particular diagnostic test or treatment.

In particular, it has now been discovered that cytopheretic devices can be useful in increasing cardiac function, for example, left ventricular ejection fraction, cardiac output, systemic vascular resistance etc., in subjects with myocardial dysfunction secondary to inflammatory cell penetration of heart tissue (for example, the myocardial tissue) such as subjects having or at risk of having chronic heart failure or acute decompensated heart failure. The inflammatory cells that can affect myocardial function include, for example, leukocytes (for example, monocytes or macrophages) or platelets.

As used herein, the term "inflammatory condition," includes any inflammatory disease, any inflammatory disorder, and/or any leukocyte activated disorder wherein the organism's immune cells are activated. Such a condition can be characterized by (i) a persistent inflammatory response with pathologic sequelae and/or (ii) infiltration of leukocytes, for example, mononuclear cells and neutrophils, leading to tissue destruction.

Leukocytes, for example, neutrophils, are major contributors to the pathogenesis and progression of many clinical inflammatory conditions. Several different and diverse types of leukocytes exist; however, they are all produced and derived from a pluripotent cell in the bone marrow known as a hematopoietic stem cell. Leukocytes, also referred to as white blood cells, are found throughout the body, including in the blood and lymphatic system. There are several different types of leukocytes including granulocytes and agranulocytes. Granulocytes are leukocytes characterized by the presence of differently staining granules in their cytoplasm when viewed under light microscopy. These granules contain membrane-bound enzymes, which primarily act in the digestion of endocytosed particles. There are three types of granulocytes: neutrophils, basophils, and eosinophils, which are named according to their staining properties. Agranulocytes are leukocytes characterized by the absence of granules in their cytoplasm and include lymphocytes, monocytes, and macrophages.

Platelets, or thrombocytes, also contribute to inflammatory conditions, as well as to homeostasis. Upon activation, platelets aggregate to form platelet plugs, and they secrete cytokines and chemokines to attract and activate leukocytes. Platelets are found throughout the body's circulation and are derived from megakaryocytes.

The molecules that are primarily responsible for initiation of leukocyte and platelet adhesion to endothelium are P-selectin and von Willebrand factor, respectively. These molecules are found in the same granules, known as Weibel-Palade bodies, in endothelial cells. Upon activation of endothelial cells, the Weibel-Palade bodies migrate to the cell membrane to expose P-selectin and soluble von Willebrand factor at the endothelial cell surface. This, in turn, induces a cascade of leukocyte and platelet activity and aggregation.

The procedures described herein employ a SCD device that is in fluid flow communication with the subject, such that a body fluid (for example, blood) flows from the subject to the SCD device, and after passing through the SCD device flows back to the subject. Activated leukocytes, for example, activated monocytes, and/or activated platelets are sequestered within the SCD device on the fluid contacting surface of a solid support (for example, the outer surface of hollow or solid fibers that contact fluid as it passes through the SCD device or the fluid contacting surfaces of a planar support). The activated leukocytes and/or platelets are deactivated by exposure to one or more leukocyte inhibiting agents that are discussed below.

The devices can be used to increase myocardial function in subjects experiencing myocardial dysfunction that is secondary to inflammatory cell penetration of heart tissue (for example, myocardial tissue). The methods and devices described herein can be used therapeutically or prophylactically to increase myocardial function in a subject with chronic heart failure and/or acute decompensated heart failure. Each of these disorders is considered to be an inflammatory condition that also affects myocardial function in the subject. In addition, the methods and devices described herein can be used to therapeutically or prophylactically treat subjects experiencing or at risk of experiencing organ/tissue rejection following transplantation of an or organ (for example, a heart, liver or kidney) or tissue.

The subjects that are candidates for this treatment can be identified using standard techniques. For example, myocardial dysfunction can be measured by measuring one or more cardiac parameters, which can include, for example, left ventricular ejection fraction, cardiac output, systemic vascular resistance, left ventricular stroke volume, aortic pressure, left ventricular pressure, peak rate of change of left ventricular pressure during isovolumic contraction and relaxation, left ventricular end-diastolic pressure, myocardial oxygen consumption, and coronary flow reserve. These parameters can be easily measured before, during and after treatment with a SCD device.

The improvement of cardiac function is demonstrated below in Example 5, where an improvement in left ventricular ejection fraction, cardiac output and systemic vascular resistance was observed in subjects with chronic heart failure following treatment with a SCD device and a leukocyte inhibiting agent (citrate).

In certain embodiments, treatment of a subject may improve the left ventricular ejection fraction by at least 1% (compared to the left ventricular ejection fraction prior to treatment). For example, treatment of a subject may improve the left ventricular ejection fraction by at least 2%, at least 3%, at least 4%, at least 5%, at least 6%, at least 7%, at least 8%, at least 9%, at least 10%, at least 12%, at least 14%, at least 16%, at least 18%, at least 20%, at least 25%, at least 30%, at least 35%, at least 40%, at least 45%, or at least 50%. The treatment may continue until the subject has attained a left ventricular ejection fraction of at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, or at least 50%. The treatment may provide a residual improvement in the left ventricular ejection fraction for at least 5 minutes, at least 10 minutes, at least 20 minutes, at least 30 minutes, at least 45 minutes, at least 1 hour, at least 2 hours, at least 3 hours, at least 4 hours, at least 5 hours, at least 6 hours, at least 12 hours, at least 1 day, at least 2 days, at least 3 days, at least 4 days, at least 5 days, at least 6 days, at least 7 days, at least 10 days, at least 14 days, at least 21 days, or at least 28 days.

In certain embodiments, treatment of a subject may improve the cardiac output by at least 1% (compared to the cardiac output prior to treatment). For example, treatment of a subject may improve the cardiac output by at least 2%, at least 3%, at least 4%, at least 5%, at least 6%, at least 7%, at least 8%, at least 9%, at least 10%, at least 12%, at least 14%, at least 16%, at least 18%, at least 20%, at least 25%, at least 30%, at least 35%, at least 40%, at least 45%, or at least 50%. The treatment may continue until the subject has attained a cardiac output of at least 2.5 L/min, at least 3.0 L/min, at least 3.5 L/min, at least 4.0 L/min, at least 4.5 L/min, at least 5.0 L/min, or at least 5.25 L/min. The treatment may provide a residual improvement in the cardiac output for at least 5 minutes, at least 10 minutes, at least 20 minutes, at least 30 minutes, at least 45 minutes, at least 1 hour, at least 2 hours, at least 3 hours, at least 4 hours, at least 5 hours, at least 6 hours, at least 12 hours, at least 1 day, at least 2 days, at least 3 days, at least 4 days, at least 5 days, at least 6 days, at least 7 days, at least 10 days, at least 14 days, at least 21 days, or at least 28 days.

In certain embodiments, treatment of a subject may improve the left ventricular stroke volume by at least 1% (compared to the stroke volume prior to treatment). For example, treatment of a subject may improve the left ventricular stroke volume by at least 2%, at least 3%, at least 4%, at least 5%, at least 6%, at least 7%, at least 8%, at least 9%, at least 10%, at least 12%, at least 14%, at least 16%, at least 18%, at least 20%, at least 25%, at least 30%, at least 35%, at least 40%, at least 45%, or at least 50%. The treatment may continue until the subject has attained a left ventricular stroke volume of at least 27 ml, at least 30 ml, at least 35 ml, at least 40 ml, at least 45 ml, at least 50 ml, at least 55 ml, at least 60 ml, at least 65 ml, or at least 70 ml. The treatment may provide a residual improvement in left ventricular stroke volume for at least 5 minutes, at least 10 minutes, at least 20 minutes, at least 30 minutes, at least 45 minutes, at least 1 hour, at least 2 hours, at least 3 hours, at least 4 hours, at least 5 hours, at least 6 hours, at least 12 hours, at least 1 day, at least 2 days, at least 3 days, at least 4 days, at least 5 days, at least 6 days, at least 7 days, at least 10 days, at least 14 days, at least 21 days, or at least 28 days.

In certain embodiments, treatment of a subject may reduce the systemic vascular resistance by at least 1% (compared to the systemic vascular resistance prior to treatment). For example, treatment of a subject may reduce the systemic vascular resistance by at least 2%, at least 3%, at least 4%, at least 5%, at least 6%, at least 7%, at least 8%, at least 9%, at least 10%, at least 12%, at least 14%, at least 16%, at least 18%, at least 20%, at least 25%, at least 30%, at least 35%, at least 40%, at least 45%, or at least 50%. The treatment may continue until the subject has attained a systemic vascular resistance of no more than 3500 dyn·s/$cm^5$, no more than 3000 dyn·s/cm, no more than 2500 dyn·s/cm, no more than 2000 dyn·s/cm, or no more than 1600 dyn·s/$cm^5$. The treatment may provide a residual improvement in the systemic vascular resistance for at least 5 minutes, at least 10 minutes, at least 20 minutes, at least 30 minutes, at least 45 minutes, at least 1 hour, at least 2 hours, at least 3 hours, at least 4 hours, at least 5 hours, at least 6 hours, at least 12 hours, at least 1 day, at least 2 days, at least 3 days, at least 4 days, at least 5 days, at least 6 days, at least 7 days, at least 10 days, at least 14 days, at least 21 days, or at least 28 days.

In addition to assessing myocardial function directly through hemodynamic parameters, subjects can also be assessed by monitoring of biomarkers such as norepinephrine, n-terminal brain natriuretic peptide (BNP), atrial natriuretic peptide (ANP), galectin-3, C-reactive protein, tumor necrosis factor-α (TNF-α), interleukin-1, interleukin-6, and troponin-1.

Although the invention is generally described herein with regard to blood and blood-based body fluids, the invention is applicable to any sample of a body fluid that can flow through an extracorporeal circuit, such as any body fluid from a subject that contains leukocytes and/or platelets. Exemplary extracorporeal circuits are described, for example, in U.S. Pat. Nos. 6,561,997 and 8,251,941; U.S. Patent Application No. 61/584,337, filed Jan. 9, 2012; International Patent Application No. PCT/US11/56469, filed Oct. 14, 2011, and published as International Patent Application Publication No. WO 2012/051595; and International Application No. PCT/US2012/059614 entitled "Cartridge and Method for Increasing Myocardial Function," filed Oct. 10, 2012; the entire disclosures of each of which are incorporated herein by reference. The terms "sample" and "specimen" are used in their broadest sense. On the one hand, they are meant to include a specimen or culture. On the other hand, they are meant to include both biological and environmental samples. Body fluids include, but not limited to, blood, serum, plasma, cerebrospinal fluid (CSF), lymphatic fluid, peritoneal fluid or ascites, pleural fluid, and saliva.

The following sections discuss exemplary SCD cartridges, systems incorporating such SCD cartridges, and their use in increasing cardiac function in a subject in need thereof.

2. Cartridge Considerations

Although the underlying principles for an appropriate SCD are discussed in detail, it is understood that SCD cartridges useful in the practice of the invention are not limited to the particular design configurations discussed herein.

One exemplary SCD cartridge useful in the practice of the invention comprises a rigid housing defining an inner volume (IV), a fluid inlet port and a fluid outlet port. The inner volume is in fluid flow communication with both the fluid inlet port and the fluid outlet port. The inner volume is also referred to herein as the fill volume, and also the extracapillary space or (ECS) in embodiments that contain hollow fibers. The inner volume can be determined by sealing either the fluid inlet port or the fluid outlet port of the rigid housing, filling the SCD cartridge with a liquid, for example, water, via the unsealed port and then measuring the volume of liquid that fills the housing to the top of the unsealed port. In addition, the cartridge comprises a solid support disposed within the housing so at least a portion of the solid support isolated between the fluid inlet port and the fluid outlet port and defining a fluid contacting surface with a surface area (SA) capable of sequestering an activated leukocyte and/or an activated platelet, if present in a biological fluid entering the housing via the fluid inlet port.

It is understood that the choice of surface area of the solid support in a SCD cartridge capable of sequestering the leukocytes and/or the platelets, and the inner volume (also referred to as the fill volume) of the housing of the SCD cartridge that contains the solid support can have a profound effect on the efficacy of the SCD in treating certain inflammatory conditions. (See PCT/US11/056469.) The surface area of the solid support should be sufficient to sequester a portion of the leukocytes and/or platelets to be effective but without sequestering too many leukocytes and/or platelets. The sequestration of too many leukocytes can result in leukocyte deficiency that in turn can result in life-threatening leucopenia. The sequestration of too many neutrophils can result in neutropenia, and the sequestration of too many platelets can result in thrombocytopenia or bleeding diathesis. Furthermore, it can be important to choose a housing with an appropriate inner volume (also referred to as the fill volume or the extracapillary space when the solid support is defined by hollow fibers) depending upon the subject to be treated. For example, in the case of infants, children and severely ill, hemodynamically unstable patients, it is important to choose housings with lower fill volumes so that less body fluid needs to be extracted from the subject to contact or bathe the solid support. Accordingly, the choice of a SCD cartridge having the appropriate ratio of active surface area of the solid support to the inner volume of the SCD cartridge housing containing the solid support can have a profound effect on the efficacy of treatment in a given patient. The age, weight, and infirmity of the subject can be important considerations when choosing a particular SCD cartridge.

Depending upon the device, the SA/IV ratio of the cartridge can be in the range from 25 $cm^{-1}$ to 2,000 $cm^{-1}$, 25 $cm^{-1}$ to 1,750 $cm^{-1}$, 25 $cm^{-1}$ to 1,500 $cm^{-1}$, 25 $cm^{-1}$ to 1,250 $cm^{-1}$, 25 $cm^{-1}$ to 1,000 $cm^{-1}$, 25 $cm^{-1}$ to 800 $cm^{-1}$, 80 $cm^{-1}$ to 2,000 $cm^{-1}$, 80 $cm^{-1}$ to 1,750 $cm^{-1}$, 80 $cm^{-1}$ to 1,500 $cm^{-1}$, 80 $cm^{-1}$ to 1,250 $cm^{-1}$, 80 $cm^{-1}$ to 1,000 $cm^{-1}$, 80 $cm^{-1}$ to 800 $cm^{-1}$, 100 $cm^{-1}$ to 2,000 $cm^{-1}$, 100 $cm^{-1}$ to 2,000 $cm^{-1}$, 100 $cm^{-1}$ to 1,750 $cm^{-1}$, 100 $cm^{-1}$ to 1,500 $cm^{-1}$, 100 $cm^{-1}$ to 1,250 $cm^{-1}$, 100 $cm^{-1}$ to 1,000 $cm^{-1}$, 100 $cm^{-1}$ to 800 $cm^{-1}$, from 125 $cm^{-1}$ to 2,000 $cm^{-1}$, 125 $cm^{-1}$ to 1,750 $cm^{-1}$, 125 $cm^{-1}$ to 1,500 $cm^{-1}$, 125 $cm^{-1}$ to 1,250 $cm^{-1}$, 125 $cm^{-1}$ to 1,000 $cm^{-1}$, or 125 $cm^{-1}$ to 800 $cm^{-1}$, 150 $cm^{-1}$ to 2,000 $cm^{-1}$, 150 $cm^{-1}$ to 1,750 $cm^{-1}$, 150 $cm^{-1}$ to 1,500 $cm^{-1}$, 150 $cm^{-1}$ to 1,250 $cm^{-1}$, 150 $cm^{-1}$ to 1,000 $cm^{-1}$, 150 $cm^{-1}$ to 800 $cm^{-1}$, 200 $cm^{-1}$ to 2,000 $cm^{-1}$, 200 $cm^{-1}$ to 1,750 $cm^{-1}$, 200 $cm^{-1}$ to 1,500 $cm^{-1}$, 200 $cm^{-1}$ to 1,250 $cm^{-1}$, 200 $cm^{-1}$ to 1,000 $cm^{-1}$, 200 $cm^{-1}$ to 800 $cm^{-1}$, 200 $cm^{-1}$ to 600 $cm^{-1}$, from 300 $cm^{-1}$ to 2,000 $cm^{-1}$, from 300 $cm^{-1}$ to 2,000 $cm^{-1}$, from 300 $cm^{-1}$ to 1,750 $cm^{-1}$, from 300 $cm^{-1}$ to 1,500 $cm^{-1}$, from 300 $cm^{-1}$ to 1,250 $cm^{-1}$, from 300 $cm^{-1}$ to 1,000 $cm^{-1}$, 300 $cm^{-1}$ to 800 $cm^{-1}$, from 400 $cm^{-1}$ to 1,200 $cm^{-1}$, from 400 $cm^{-1}$ to 1,000 $cm^{-1}$, from 400 $cm^{-1}$ to 800 $cm^{-1}$, from 500 $cm^{-1}$ to 1,200 $cm^{-1}$, from 500 $cm^{-1}$ to 1000 $cm^{-1}$, or from 500 $cm^{-1}$ to 800 $cm^{-1}$.

In certain embodiments, the SA/IV ratio of the cartridge is greater than 25 $cm^{-1}$, or 80 $cm^{-1}$, or 150 $cm^{-1}$. In certain embodiments, the SA/IV ratio of the cartridge is no greater than 80 $cm^{-1}$ (i.e., is 80 $cm^{-1}$ or less).

Furthermore, in certain embodiments, the solid support (which can comprise a plurality of fibers or planar sheets) is disposed within the housing at a packing density in the range from 20% to 65% (for example, from 20% to 60%, or from 30% to 60% or from 40% to 55%). As used herein, the term "packing density" is understood to mean the percentage of the total volume of the interior of a cartridge that is occupied by the solid support. The volume $V_{supp}$ occupied by the solid support is understood to include, for example, the aggregate volume of all the fibers, sheets, or other elements defining the solid support. If the solid support includes hollow elements, such as hollow fibers, the volume occupied by the solid support is understood to include any hollow spaces (e.g., intracapillary spaces), as well as the volume occupied by the material of the solid support. The total volume of the interior of a cartridge is therefore the sum of the fill volume (IV) of the cartridge and the volume occupied by the solid support. The packing density is the volume occupied by the solid support "inner volume" divided by the total volume of the interior of the cartridge, and can be expressed as $V_{supp}/(IV+V_{supp})$, which can also be presented as a percentage. For example, if the volume of $V_{supp}$ is 10 $cm^3$, and the IV is 20 $cm^3$, the packing density is 0.33 or 33%.

In other embodiments, the cartridge comprises (a) a rigid housing defining an inner volume (IV), a fluid inlet port and a fluid outlet port, wherein the inner volume is in fluid flow communication with the fluid inlet port and the fluid outlet port; and (b) a solid support disposed within the housing and defining a fluid contacting surface with a surface area (SA) capable of sequestering an activated leukocyte and/or an activated platelet if present in a body fluid entering the housing via the fluid inlet port, wherein the SA is greater than 2.6 $m^2$ (for example, from 3.0 $m^2$ to 10.0 $m^2$ or from 3.0 $m^2$ to 5.0 $m^2$).

In another embodiment, the cartridge comprises (a) a rigid housing defining an inner volume (IV), a fluid inlet port and a fluid outlet port, wherein the inner volume is in fluid flow communication with the fluid inlet port and the fluid outlet port; and (b) a solid support comprising a plurality of solid fibers disposed within the housing, the solid support defining a fluid contacting surface with a surface area (SA) capable of sequestering an activated leukocyte and/or an activated platelet if present in a body fluid entering the housing via the fluid inlet port, wherein the SA/IV ratio is greater than 25 cm$^{-1}$ (for example, greater than 80 cm$^{-1}$, greater than 150 cm$^{-1}$, or in the range from 150 cm$^{-1}$ to 1,500 cm$^{-1}$, in the range from 80 cm$^{-1}$ to 800 cm$^{-1}$, in the range from 25 cm$^{-1}$ to 800 cm$^{-1}$).

FIG. 1A shows a schematic, cross-sectional representation of an exemplary SCD cartridge 100. SCD cartridge 100 comprises a housing 110 that defines an inner volume or fill volume 112, a fluid inlet port 114, a fluid contacting inner surface 116, and a fluid outlet port 118. The fluid inlet port 114, inner volume (or fill volume) 112, and fluid outlet port 118 are in fluid flow communication with one another. As shown, the fluid inlet port 114 and the fluid outlet port 118 are disposed on the same side of the housing (i.e., are ipsilateral). In this embodiment, the housing further comprises a solid support 120 defined by the exterior surface(s) of one or more hollow fibers. FIG. 1A shows three hollow fibers. In this embodiment, the interior of the hollow fibers 120 together define an intracapillary space ("ICS") 122, and the volume disposed between the fluid contacting inner surface 116 of the housing and the exterior surface of the hollow fibers 120 together define the inner volume 112, which is also referred to as the extracapillary space ("ECS"). Depending upon the particular embodiment, a fluid, for example, an ultrafiltrate, can be introduced into ICS 122 of the SCD 100 via an ICS inlet 126 which can then pass into or through ICS 122 and, if desired, exit housing 110 via ICS outlet 128. In certain embodiments, however, the ICS inlet 126 can be blocked or otherwise capped with end cap 130 and/or ICS outlet 128 can be blocked or otherwise capped with end cap 132. In this embodiment, at least a portion of solid support 120 is disposed within housing 110 between fluid inlet port 114 and fluid exit port 118.

During operation of this SCD cartridge, the fluid sample of interest is introduced into housing 110 via fluid inlet 114 into inner volume (or ECS) 112. The fluid then passes along the surface of solid support 120 (along the exterior surface of the hollow fibers) in a plane substantially parallel to the plane of the solid support 120, and then exits inner volume (or ECS) 112 via fluid exit port 118. During passage along solid support 120, activated leukocytes and/or platelets are sequestered and optionally deactivated. As a result, during operation, cells (for example, leukocytes) from the body fluid (for example, blood) associate with a particular region within the passageway defined by the cartridge housing, specifically, with the exterior surface of the hollow fibers. Accordingly, in certain embodiments, a passageway region configured to sequester leukocytes may include a porous membrane that permits smaller molecules to pass therethrough but forces larger molecules and/or cells to flow along the membrane. Moreover, in certain embodiments, the passageway region configured to sequester leukocytes is bounded by a surface of a housing and is bounded by, and may include, the exterior surface or surfaces of hollow fibers configured such that the biological sample (e.g., a subject's blood or filtered blood) flows over these surfaces (i.e., over the hollow fibers). See, for example, FIG. 1. The hollow fibers may be porous, semi-porous, or non-porous and a different fluid (e.g., ultrafiltrate) may optionally flow or be present within the hollow fibers. The fibers can be formed from any suitable material described herein.

Accordingly, the invention also provides a method of using a cartridge (i) for processing an activated leukocyte, activated platelet or a combination thereof, or (ii) for treating a subject at risk of developing or having an inflammatory condition. The method comprises providing a cartridge comprising (i) a rigid housing defining an inner volume (IV), a fluid inlet port and a fluid outlet port; and (ii) a solid support disposed within the housing so at least a portion of the solid support isolated between the fluid inlet port and the fluid outlet port and defining a fluid contacting surface with a surface area (SA) capable of sequestering an activated leukocyte, if present in a biological fluid entering the housing via the fluid inlet port. In certain embodiments, the method, the SA/IV ratio of the cartridge is greater than 80 cm$^{-1}$, whereas in certain other embodiments, the SA/IV ratio of the cartridge is no greater than 80 cm$^{-1}$. The method further comprises introducing a body fluid from a subject into the housing via the fluid inlet port under conditions that permit sequestration of an activated leukocyte and/or an activated platelet on the fluid contacting surface of the solid support.

Figure 1B:
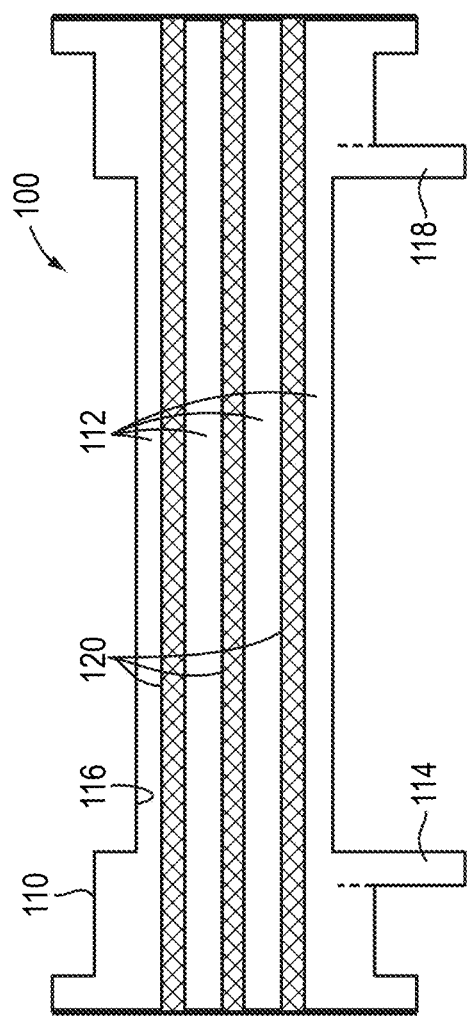
FIGS. 1B-1D are schematic, cross-sectional representations of a SCD cartridge containing a plurality of solid fibers and/or planar support members.

FIG. 1B shows a schematic, cross-sectional representation of another exemplary SCD cartridge 100. SCD cartridge 100 comprises a housing 110 that defines an inner volume 112, a fluid inlet port 114, a fluid contacting inner surface 116, and a fluid outlet port 118. The fluid inlet port 114 and the fluid outlet port 118 are disposed on the same side of the housing (i.e., are ipsilateral). In this embodiment, the housing further comprises a solid support 120 defined by the exterior surfaces of a solid substrate, which can be, for example, one or more (a plurality of) solid fibers or one or more (a plurality of) planar supports (for example, a flat membrane). In this FIG. 1B, which shows a cross-sectional representation of a SCD cartridge, the solid support is defined by three solid fibers or three sheets of a planar support member (for example, a planar membrane). However, it is understood that a plurality of solid fibers or planar support members may together define the solid support. The volume disposed between the fluid contacting inner surface 118 of the housing and the exterior surface of the solid fiber(s) or the planar support member(s) together define the inner volume (or fill volume) 112. In contrast to the embodiment shown in FIG. 1A, the solid fibers or planar support members, because they are not hollow, do not define an ICS. In this embodiment, at least a portion of solid support 120 is disposed within housing 110 between fluid inlet port 114 and fluid exit port 118.

During operation of this SCD cartridge, the fluid sample of interest is introduced into housing 110 via fluid inlet part 114 into the inner volume (ECS) 112. The fluid then passes along the surface of solid support 120 (along the exterior surface of the solid fibers or planar support, or a combination of one or more solid fibers with one or more planar supports) in a plane substantially parallel to the plane of the solid support 120 and then exits inner volume 112 via fluid exit port 118. During movement of the body fluid along solid support 120, activated leukocytes and/or platelets are sequestered.

Figure 1C:
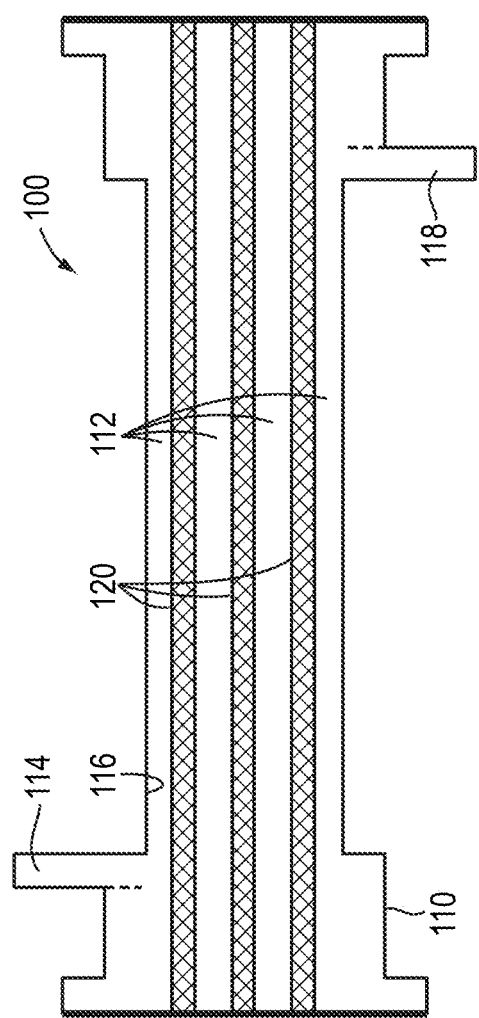
Figure 1D:
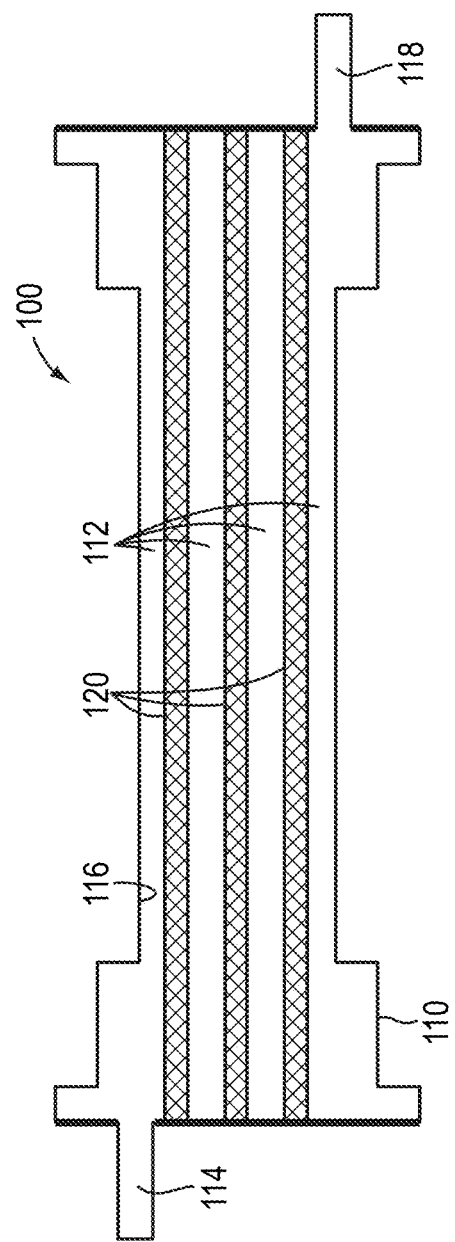

The SCD cartridges shown in FIGS. 1C and 1D are similar to the SCD cartridge shown in FIG. 1B. In FIG. 1C, the fluid inlet port 114 and fluid outlet port 118 are located at opposite sides of the housing (i.e., are contralateral). In FIG. 1C, housing 110 has a first end and a second end opposite the first end, where fluid inlet port 114 is configured to permit fluid flow through first end and fluid outlet port 118 is configured to permit fluid flow through the second end.

The SCD cartridge can be configured in any of a variety of ways to sequester cells, for example, leukocytes. As will be discussed in more detail below, the SCD cartridge preferably is designed with a particular subject and indication in mind. For example, the surface area of the solid support should be sufficient to sequester a portion of the activated leukocytes and/or activated platelets to be effective without sequestering too many leukocytes, which potentially can cause life-threatening leukopenia, neutropenia, or too many platelets resulting in thrombocytopenia, or bleeding diathesis. Furthermore, it can be important to choose a housing with an appropriate inner volume depending upon the subject to be treated. For example, in the case of infants, children and severely ill, hemodynamically unstable patients, it is important to choose housings with lower fill volumes so that less body fluid needs to be extracted from the subject in order to contact or bathe the solid support. It is understood that the SCD cartridge can be configured in any of a variety of ways to sequester cells, for example, leukocytes, and to have the appropriate inner volume.

The solid support can be defined by any number of surfaces, for example, 1, 2, 3, 4, 5, 10, 20, 50, 100, or more different surfaces. Depending upon the subject and the indication to be treated, the surface area of the solid support is greater than about 0.09 $m^2$, is greater than about 0.1 $m^2$, is greater than about 0.2 $m^2$, greater than 0.4 $m^2$, greater than 0.6 $m^2$, greater than 0.8 $m^2$, greater than 1.0 $m^2$, greater than 1.5 $m^2$, or greater than 2.0 $m^2$.

The surface area of the solid support can be in the range of 0.1 $m^2$ to 10.0 $m^2$, or 0.1 $m^2$ to 5.0 $m^2$. More specifically, the surface area of the solid support can be in the range from 0.1 $m^2$ to 0.4 $m^2$, from 0.4 $m^2$ to 0.8 $m^2$, from 0.8 $m^2$ to 1.2 $m^2$, from 1.2 $m^2$ to 1.6 $m^2$, from 1.6 $m^2$ to 2.0 $m^2$, from 2.0 $m^2$ to 2.4 $m^2$, from 2.4 $m^2$ to 2.8 $m^2$, from 2.8 $m^2$ to 3.2 $m^2$, from 3.2 $m^2$ to 3.6 $m^2$, from 3.6 $m^2$ to 4.0 $m^2$, from 4.0 $m^2$ to 4.4 $m^2$, from 4.4 $m^2$ to 4.8 $m^2$, from 4.8 $m^2$ to 5.2 $m^2$, from 5.2 $m^2$ to 5.6 $m^2$, from 5.6 $m^2$ to 6.0 $m^2$, from 6.0 $m^2$ to 6.4 $m^2$, from 6.4 $m^2$ to 6.8 $m^2$, from 6.8 $m^2$ to 7.2 $m^2$, from 7.2 $m^2$ to 7.6 $m^2$, from 7.6 $m^2$ to 8.0 $m^2$, from 8.0 $m^2$ to 8.4 $m^2$, from 8.4 $m^2$ to 8.8 $m^2$, from 8.8 $m^2$ to 9.2 $m^2$, from 9.2 $m^2$ to 9.6 $m^2$, or from 9.6 $m^2$ to 10.0 $m^2$.

As a general guiding principle, it is contemplated that when treating subjects having a body weight less than 50 kg the surface area of the solid support preferably should be in the range of the from 0.4 $m^2$ to 0.8 $m^2$, when treating subjects having a body weight greater than 50 kg but less than 100 kg, the surface area of the solid support preferably should be in the range of the from 0.8 $m^2$ to 1.6 $m^2$, and when treating subjects having a body weight greater than 100 kg the surface area of the solid support preferably should be in the range of the from 1.6 $m^2$ to 5.0 $m^2$. It is understood, however, that when therapy is initiated, if the patient shows symptoms of developing leukopenia and/or neutropenia, the SCD cartridge can be replaced with a cartridge with a lower surface area to avoid sequestering too many leukocytes and/or platelets.

The housing of the cartridge is not limited to a particular set of dimensions (e.g., length, width, weight, or other dimension) in order to achieve a particular fill volume. Depending upon the subject and the indication to be treated, the IV can be less than 300 $cm^3$, or less than 150 $cm^3$, or less than 100 $cm^3$, or less than 80 $cm^3$, or less than 60 $cm^3$, or less than 40 $cm^3$, or less than 20 $cm^3$. In certain embodiments, the IV is in the range of from 10 $cm^3$ to 150 $cm^3$, 75 $cm^3$ to 150 $cm^3$, 20 $cm^3$ to 80 $cm^3$, or 15 $cm^3$ to 120 $cm^3$. In the case of infants, children, and severely ill, hemodynamically unstable patients, the inner volume can be less than 40 $cm^3$, for example, in the range from 5 $cm^3$ to 50 $cm^3$, from 1 $cm^3$ to 20 $cm^3$ or from 5 $cm^3$ to 30 $cm^3$.

In certain embodiments, the SA/IV ratio is in the range from 25 $cm^{-1}$ to 2,000 $cm^{-1}$, 25 $cm^{-1}$ to 1,750 $cm^{-1}$, 25 $cm^{-1}$ to 1,500 $cm^{-1}$, 25 $cm^{-1}$ to 1,250 $cm^{-1}$, 25 $cm^{-1}$ to 1,000 $cm^{-1}$, 25 $cm^{-1}$ to 800 $cm^{-1}$, 80 $cm^{-1}$ to 2,000 $cm^{-1}$, 80 $cm^{-1}$ to 1,750 $cm^{-1}$, 80 $cm^{-1}$ to 1,500 $cm^{-1}$, 80 $cm^{-1}$ to 1,250 $cm^{-1}$, 80 $cm^{-1}$ to 1,000 $cm^{-1}$, 80 $cm^{-1}$ to 800 $cm^{-1}$, 100 $cm^{-1}$ to 2,000 $cm^{-1}$, 100 $cm^{-1}$ to 2,000 $cm^{-1}$, 100 $cm^{-1}$ to 1,750 $cm^{-1}$, 100 $cm^{-1}$ to 1,500 $cm^{-1}$, 100 $cm^{-1}$ to 1,250 $cm^{-1}$, 100 $cm^{-1}$ to 1,000 $cm^{-1}$, 100 $cm^{-1}$ to 800 $cm^{-1}$, from 125 $cm^{-1}$ to 2,000 $cm^{-1}$, 125 $cm^{-1}$ to 1,750 $cm^{-1}$, 125 $cm^{-1}$ to 1,500 $cm^{-1}$, 125 $cm^{-1}$ to 1,250 $cm^{-1}$, 125 $cm^{-1}$ to 1,000 $cm^{-1}$, or 125 $cm^{-1}$ to 800 $cm^{-1}$, 150 $cm^{-1}$ to 2,000 $cm^{-1}$, 150 $cm^{-1}$ to 1,750 $cm^{-1}$, 150 $cm^{-1}$ to 1,500 $cm^{-1}$, 150 $cm^{-1}$ to 1,250 $cm^{-1}$, 150 $cm^{-1}$ to 1,000 $cm^{-1}$, 150 $cm^{-1}$ to 800 $cm^{-1}$, 200 $cm^{-1}$ to 2,000 $cm^{-1}$, 200 $cm^{-1}$ to 1,750 $cm^{-1}$, 200 $cm^{-1}$ to 1,500 $cm^{-1}$, 200 $cm^{-1}$ to 1,250 $cm^{-1}$, 200 $cm^{-1}$ to 1,000 $cm^{-1}$, 200 $cm^{-1}$ to 800 $cm^{-1}$, 200 $cm^{-1}$ to 600 $cm^{-1}$, from 300 $cm^{-1}$ to 2,000 $cm^{-1}$, from 300 $cm^{-1}$ to 2,000 $cm^{-1}$, from 300 $cm^{-1}$ to 1,750 $cm^{-1}$, from 300 $cm^{-1}$ to 1,500 $cm^{-1}$, from 300 $cm^{-1}$ to 1,250 $cm^{-1}$, from 300 $cm^{-1}$ to 1,000 $cm^{-1}$, 300 $cm^{-1}$ to 800 $cm^{-1}$, from 400 $cm^{-1}$ to 1,200 $cm^{-1}$, from 400 $cm^{-1}$ to 1,000 $cm^{-1}$, from 400 $cm^{-1}$ to 800 $cm^{-1}$, from 500 $cm^{-1}$ to 1,200 $cm^{-1}$, from 500 $cm^{-1}$ to 1000 $cm^{-1}$, or from 500 $cm^{-1}$ to 800 $cm^{-1}$.

The housing of the cartridge can be fabricated from a variety of materials, but the material that defines that fluid contacting surface in the inner volume should be biocompatible. The SCD cartridge can be constructed from a variety of materials including, metals such as titanium, or stainless steel with or without surface coatings of refractory metals including titanium, tantalum, or niobium; ceramics such as alumina, silica, or zirconia; or polymers, such as polyvinylchloride, polyethylene, or polycarbonate.

The solid support can be defined by flat surfaces (e.g., sheets), curved surfaces (e.g., hollow tubes, hollow fibers, solid tubes, and solid fibers), patterned surfaces (e.g., z-folded sheets or dimpled surfaces), irregularly-shaped surfaces, or other configurations to sequester cells. It is understood that the solid support can be defined by a variety of materials, which can include, for example, hollow fibers, solid fibers, planar support members (for example, planar membranes) or a combination of two or more of the foregoing (for example, a combination of hollow and solid fibers, a combination of hollow fibers and planar support members, or a combination of solid fibers and planar support members). In certain embodiments, the solid support is substantially parallel to the plane of fluid flow within the SCD cartridge from fluid inlet port 114 to the fluid exit port.

Depending upon the embodiment, the solid support can comprise a membrane. The term "membrane" refers to a surface capable of receiving a fluid on both sides of the surface, or a fluid on one side and gas on the other side of the surface. A membrane can be porous (e.g., selectively porous or semi-porous) such that it is capable of fluid or gas flow therethrough. It is understood that the term "porous" as used herein to describe a surface or membrane includes generally porous, selectively porous and/or semi-porous surfaces or membranes. Moreover, additional surfaces that can facilitate leukocyte sequestration, such as particle (e.g., bead) surfaces, surfaces of one or more projections into the passageway, or surfaces of one or more membranes exposed to the flowing biological sample.

It is understood that the solid support is not limited to a particular type, kind or size, and may be made of any appropriate material; however, the material should be biocompatible. For example, a surface of the solid support may be any biocompatible polymer comprising one or more of nylon, polyethylene, polyurethane, polyethylene terephthalate (PET), polytetrafluoroethylene (PTFE), CUPROPHAN (a cellulose regenerated by means of the cuprammonium process, available from Enka), HEMOPHAN (a modified CUPROPHAN with improved biocompatibility, available from Enka), CUPRAMMONIUM RAYON (a variety of CUPROPHAN, available from Asahi), BIOMEMBRANE (cuprammonium rayon available from Asahi), saponified cellulose acetate (such as fibers available from Teijin or CD Medical), cellulose acetate (such as fibers available from Toyobo Nipro), cellulose (such as that are regenerated by the modified cupramonium process or by means of the viscose process, available from Terumo or Textikombinat (Pirna, GDR) respectively), polyacrylonitrile (PAN), polysulfone, polyethersulfone, polyarylethersulfone, acrylic copolymers (such as acrylonitrile-NA-methallyl-sulfonate copolymer, available from Hospal), polycarbonate copolymer (such as GAMBRONE, a fiber available from Gambro), polymethylmethacrylate copolymers (such as fibers available from Toray), and ethylene vinyl copolymer (such as EVAL, a ethylene-vinyl alcohol copolymer available from Kuraray). Alternatively, a surface may be nylon mesh, cotton mesh, or woven fiber. The surface can have a constant thickness or an irregular thickness. In some embodiments, surfaces may include silicon, for example, silicon nanofabricated membranes (see, e.g., U.S. Patent Publication No. 2004/0124147). In some embodiments, surfaces may include polysulfone fibers. Other suitable biocompatible fibers are known in the art, for example, in Salem and Mujais (1993) DIALYSIS THERAPY 2D ED., Ch. 5: Dialyzers, Eds. Nissensen and Fine, Hanley & Belfus, Inc., Philadelphia, Pa.

Any technique or combination of techniques that facilitate sequestration (for example, binding) of the leukocytes and platelets can be used, including, for example, biological, chemical, mechanical and/or physical techniques. In some embodiments, biological or chemical techniques for sequestration can be used. Such techniques include using tissues, cells, biomolecules (for example, proteins or nucleic acids), or small molecules to sequester leukocytes. In one embodiment, for example, the fluid contacting support of the solid support in the ECS can further comprise a cell adhesion molecule attached thereto to facilitate sequestration.

For example, when a leukocyte is activated, selectins are produced by the leukocyte. This altered selectin production can facilitate binding between the leukocyte and other leukocytes. In turn, the binding between leukocytes can increase selectin production in the additionally bound leukocytes, yielding exponential binding of leukocytes. Thus, selectins may be useful to enhance sequestration. Proteins, protein complexes, and/or protein components known to bind leukocytes include CD11a, CD11b, CD11c, CD18, CD29, CD34, CD44, CD49d, CD54, podocalyxin, endomucin, glycosaminoglycan cell adhesion molecule-1 (Gly-CAM-1), mucosal addressin cell adhesion molecule-1 (MAdCAM-1), E-selectin, L-selectin, P-selectin, cutaneous lymphocyte antigen (CLA), P-selectin glycoprotein ligand 1 (PSGL-1), leukocyte functional antigen-1 (LFA-1), Mac-1, leukocyte surface antigen p150,95, leukocyte integrin CR4, very late antigen-4 (VLA-4), lymphocyte Peyers patch adhesion molecule-1 (LPAM-1), intracellular adhesion molecule-1 (ICAM-1), intracellular adhesion molecule-2 (ICAM-2), intracellular adhesion molecule-3 (ICAM-3), inactivated C3b (C3bi), fibrinogen, fibronectin, peripheral lymph node addressin (PNAd), endothelial vascular adhesion protein 1 (VAP-1), fractalkine, CCL19, CCL21, CCL25, and CCL27. Other large molecules known to bind leukocytes include hyaluronic acid, glycosaminoglycans (GAGs), and fucosylated oligosaccharides and their precursors. In certain embodiments, small molecules or adherents used to sequester a leukocyte can include, but are not limited to, peptides, such as peptides comprising the amino acid sequence arginine-glycine-aspartic acid (RGD), and molecules comprising sialic acid. Accordingly, any of these materials can be used to enhance sequestration.

During use, any of these biological or chemical materials may be bound to the fluid contacting surface of the solid support and/or the fluid contacting surface of the cartridge housing to facilitate or enhance sequestration. Alternatively, or in combination, any of these materials may be used with other additional techniques to facilitate sequestration. For example, materials may be used to bind leukocytes in solution, causing them to agglomerate and to increase their overall size relative to the size of a single leukocyte. The agglomerated leukocytes then can be captured with a membrane having a particular pore size.

It should be understood that the sequestration techniques described herein also can apply to platelets. In the case of platelets, similar biological, chemical, mechanical and/or physical techniques as described above may be used to sequester platelets. In certain embodiments, agents used to sequester platelets include one or more of glycoprotein Ibα (GPIbα), glycoprotein IIb (GPIIb), glycoprotein IIIa (GPIIIa), CD41, CD61, von Willebrand Factor, $\beta_2$-integrin macrophage antigen-1, selectins such as P-selectin, and a cell-adhesion molecule.

In addition, sequestration can also be facilitated and/or enhanced by the control of certain mechanical forces that occur within the SCD cartridge. For example, leukocytes may be sequestered on one or more surfaces of (or in) a passageway or passageway region (e.g., the outside of a porous hollow fiber) by utilizing a flow rate and device configuration that minimizes shear force between the leukocytes and the surface(s), allowing the leukocytes to associate with the surface(s). For example, the housing is configured to create a low shear force environment to permit the cells of interest, for example, leukocytes, platelets, etc, to be sequestered on the solid support as body fluid traverses the inner volume.

More specifically, the cartridge is configured to facilitate shear forces between the flowing cells (for example, leukocytes or platelets) and the sequestration surface(s) less than 1000 dynes/cm$^2$, less than 500 dynes/cm$^2$, less than 100 dynes/cm$^2$, less than 80 dynes/cm$^2$, less than 60 dynes/cm$^2$, less than 40 dynes/cm$^2$, less than 20 dynes/cm$^2$, less than 10 dynes/cm$^2$, or less than 5 dynes/cm$^2$ when a biological fluid enters the cartridge housing through fluid inlet port 114 and exits the cartridge housing through the fluid outlet port 118, for example, at a flow rate in the range of 10 mL (cm$^3$)/minute to about 8,000 mL (cm$^3$)/minute or from 50 mL/minute to about 8,000 mL/minute (for example, 1,000 cm$^3$/minute). As a result, the fluid inlet port 114 and the fluid outlet port 118 are dimensioned to permit a flow rate through the housing in a range from 10 mL/minute to 8,000 mL/minute or from 50 mL/minute to 8,000 mL/minute. For example, when treating certain inflammatory disorders, for example, inflammatory responses during cardiopulmonary bypass, it is understood that treating large flow rates can be tolerated, for example, up to 7000 mL/minute. That said, when treating inflammatory responses associated with other indications, for example, chronic heart failure or acute decompensated heart failure, slower flow rates should be used, for example, less than about 500 mL/minute, from about 100 mL/minute to about 500 mL/minute, and from about 200 mL/minute to about 500 mL/minute. As a result, the inlet port 114 and the outlet port 118 are dimensioned to permit a desired volume of body fluid to pass through the SCD cartridge housing in a given amount of time. It is understood that the fluid inlet port 114 and the fluid outlet port 118 each have an internal diameter of no less than 0.1 cm to 2 cm, or 0.2 cm to 1 cm, or have a cross-sectional surface area of no less than 0.01 cm$^2$, no less than 0.1 cm$^2$, no less than 0.2 cm$^2$, no less than 0.4 cm$^2$, no less than 0.6 cm$^2$, no less than 0.8 cm$^2$, no less than 1.0 cm$^2$, no less than 2.0 cm$^2$, or no less than 3.0 cm$^2$. In certain embodiments, the inlet port, the outlet port, or both the inlet and outlet ports have a cross-sectional surface area of 0.01 cm$^2$ to 1 cm$^2$. The distance between the fluid inlet or fluid outlet to the nearest end of the housing (distance A), can be such that A divided by the length of the housing is between 0.01 and 0.25. It is also understood that the plane of the inlet and/or outlet port can range from 5 degrees to 90 degrees (i.e., is perpendicular) to the plane defined by the longest dimension (usually the length) of the housing.

In certain embodiments, the fluid inlet port 114 and the fluid outlet port 118 are both disposed on one side of the housing 116, for example, as shown in FIGS. 1A and 1B. Alternatively, as shown in FIG. 1C, the fluid inlet port 114 and the fluid outlet port 116 can be disposed on opposite sides of the housing 116. Other orientations of the fluid inlet port 114 and the fluid outlet port 116 are also envisioned. For example, if the housing comprises a first end and a second end opposite the first end, the fluid inlet port can be configured to permit fluid flow through the first end and/or the fluid outlet port can be configured to permit fluid flow through the second end. One such orientation is depicted in FIG. 1D, in which fluid inlet port 114 permits fluid flow through the left end of housing 116, and fluid outlet port 118 permits the fluid to exit through the right end of housing 116.

It is understood that the size and shape of the housing of the SCD cartridge may be designed to provide the appropriate fill volume and to minimize turbulence when a fluid is passed through the SCD cartridge. Furthermore, it is understood that the size, shape and composition of the solid support located within the SCD cartridge may be designed to provide the appropriate surface area and to minimize turbulence when a fluid is passed through the SCD cartridge.

By way of example, when solid fibers are used to create the solid support in the cartridge, if a cartridge having a total surface area of 1.8 m$^2$ to 2.5 m$^2$ is desired, the cartridge can be designed to contain about 43,000 fibers when the fiber length is 26 cm and the fiber diameter is 50 µm, or about 22,000 fibers when the fiber length is 26 cm and the fiber diameter is 100 µm, or about 11,000 fibers when the fiber length is 26 cm and the fiber diameter is 200 µm, or about 43,000 fibers when the fiber length is 13 cm and the fiber diameter is 100 µm, or about 22,000 fibers when the fiber length is 13 cm and the fiber diameter is 200 µm. Alternatively, if the cartridge having a total surface area of 3.6 m$^2$ to 5.0 m$^2$ is desired, the cartridge can be designed to contain about 87,000 fibers when the fiber length is 26 cm and the fiber diameter is 50 µm, or about 43,000 fibers when the fiber length is 26 cm and the fiber diameter is 100 µm, or about 87,000 fibers when the fiber length is 13 cm and the fiber diameter is 100 µm.

In contrast, and by way of example, when planar support members are used to create the solid support, if a cartridge with a total surface area of 1.8 m$^2$ to 2.5 m$^2$ is desired, the cartridge can contain, for example, a plurality of sheets having an average thickness of 50 µm and an average width of 5 cm (for example, about 115 sheets of a membrane about 12 cm in length, or 63 sheets of membrane about 26 cm in length). In contrast, if a cartridge with a total surface area of 3.6 m$^2$ 5.0 m$^2$ is desired, the cartridge can contain about 125 sheets of membrane having an average thickness of 50 µm, an average width of 5 cm, and average length of 26 cm. The sheets may be placed within the cartridge such that, in certain embodiments, the spacing between the sheets is about 50 µm or 100 µm.

In certain embodiments, the cartridge can be designed such that the solid support (for example, the fibers or planar supports that constitute the solid support) is disposed within the housing at a packing density from 20% to 65%, 20% to 60%, from 30% to 60%, or from 40% to 55%. The packing density should be chosen to minimize the risk of clotting when blood is passed across the solid support disposed within the IV of the housing.

In certain embodiments, for example, when hollow fibers are used in the SCD cartridge, the SA/IV ratio preferably is at least 80 cm$^{-1}$ or more. Exemplary SCD cartridges with a SA/IV ratio greater than 80 cm$^{-1}$ include the F-50, F-60, F-70 and F-80A cartridge, which are available commercially from Fresenius Medical Care North America, Waltham, Mass., U.S.A.) or Renaflow cartridges (PSH series) from Baxter (Deerfield, Ill., U.S.A.). These cartridges have been approved by the USFDA for use in acute and chronic hemodialysis. The F-80A cartridge, for example, has a solid support (defined by the exterior surfaces in a bundle of hollow fibers) with a surface area capable of sequestering leukocytes and/or platelets of about 2.5 m$^2$, has an inner volume of about 250 mL, and a SA/IV ratio of about 100.

In certain embodiments, exemplary cartridges can have the features set forth in Table 1.

TABLE 1

| Device | ECS SA (m$^2$) | ECS SA (cm$^2$) | ECS Fill (cm$^3$) | SA/V (cm$^{-1}$) |
|---|---|---|---|---|
|  | 0.98 | 9800 | 130 | 75 |
| 2 | 2.5 | 25000 | 250 | 100 |
| 3 | 1.25 | 12500 | 125 | 100 |
| 4 | 2.5 | 25000 | 125 | 200 |
| 5 | 2.5 | 25000 | 109 | 230 |
| 6 | 2.5 | 25000 | 94 | 267 |
| 7 | 5 | 50000 | 93 | 536 |
| 8 | 5 | 50000 | 125 | 400 |
| 9 | 6.7 | 67000 | 125 | 537 |
| 10 | 10 | 100000 | 125 | 800 |

In certain embodiments, in particular, for pediatric uses, exemplary cartridges can have the features set forth in Table 2.

TABLE 2

| Device | ECS SA (m$^2$) | ECS SA (cm$^2$) | ECS Fill (cm$^3$) | SA/V (cm$^{-1}$) |
|---|---|---|---|---|
| 1 - 1.5 cm case; 200 µm fibers | 0.17 | 1700 | 9 | 185 |
| 2 - 1.5 cm case; 100 µm fibers | 0.35 | 3500 | 9 | 392 |
| 3 - 1.5 cm case; 75 µm fibers | 0.47 | 4700 | 9 | 530 |
| 4 - 1.5 cm case; 50 µm fibers | 0.70 | 7000 | 9 | 784 |
| 5 - 2.5 cm case; 200 µm fibers | 0.49 | 4900 | 25 | 199 |
| 6 - 2.5 cm case; 100 µm fibers | 0.98 | 9800 | 25 | 399 |
| 7 - 2.5 cm case; 75 µm fibers | 1.30 | 13000 | 25 | 526 |
| 8 - 2.5 cm case; 50 µm fibers | 1.96 | 19600 | 25 | 797 |

In certain embodiments, a system can achieve sequestration by subjecting the leukocytes, platelets or cells of interest to a series of cartridges, for example, 2, 3, 4, 5, 6, 7, 8, 9, 10, or more cartridges (e.g., hollow fiber cartridges), each comprising one or more sequestration passageways, or passageway regions, so as to increase the length of the region configured to sequester the leukocytes and the residence time of the leukocytes therein. In any of the aforementioned embodiments, the devices are configured to accomplish sequestration of leukocytes in a manner permitting inhibition of release of a pro-inflammatory substance from a leukocyte and/or deactivation of a leukocyte before, during, or after sequestering. Inhibition of release of a pro-inflammatory substance from a leukocyte and/or deactivation of a leukocyte can be achieved both during sequestration and during transport through a passageway, passageway region, or entire system of the present invention.

In some embodiments, the SCD cartridges or fluid circuits incorporating the SCD cartridges are configured to sequester the leukocytes for any desired amount of time, for example, from 1 to 59 seconds, from 1 to 59 minutes, from 1 to 24 hours, from 1 to 7 days, one or more weeks, one or more months, or one year or more. In some embodiments, the devices are configured to sequester leukocytes for an amount of time sufficient to permit the subsequent inhibition of release of a pro-inflammatory substance from the leukocytes and/or deactivation the leukocytes. In certain embodiments, leukocytes and/or platelets are sequestered within the SCD cartridge for a time (e.g., at least 1, 2, 3, 4, 5, 6, 7, 8, 9, 10, 15 minutes or at least an hour) sufficient to deactivate the leukocyte and/or inhibit the release of a pro-inflammatory substance.

It is understood that the fluid contacting surface of the solid support can sequester (for example, bind) activated leukocytes and/or activated platelets during operation. In certain embodiments, the fluid contacting surface can preferentially sequester (for example, preferentially bind) activates leukocytes and/or platelets relative to unactivated or deactivated leukocytes or platelets.

In certain embodiments, leukocytes from the subject are treated over a period of at least 2 hours, at least 4 hours, at least 6 hours, at least 8 hours, or at least 12 hours. In other embodiments, leukocytes from the subject are treated over a period of 2 to 24 hours, 2 to 12 hours, 4 to 24 hours, or 4 to 12 hours.

It is understood that the SCD cartridge, once fabricated should be sterilized prior to use. Sterility can be achieved through exposure to one or more sterilizing agents, separately or in combination, such as high temperature, high pressure, radiation, or chemical agents such as ethylene oxide, for example. The SCD cartridge preferably is sterilized once it has been packaged, for example, after it has been hermetically sealed within an appropriate container or packaging (i.e., the cartridge is terminally sterilized). The packaging may comprise plastic, and may be entirely plastic or may comprise a pouch defined by plastic adhered to a planar support, for example, a paper support. The sterilization process preferably achieves a sterility assurance level (SAL) of $10^{-3}$ or less; i.e. the probability of any given unit being nonsterile after the process is no more than 1 in $10^3$. More preferably, the sterilization process achieves an SAL of no more than $10^{-4}$, no more than $10^{-5}$, or no more than $10^{-6}$. Furthermore, it is understood that the cartridge may comprise a cap sealing fluid inlet port 114 and/or a cap sealing fluid exit port 118. Caps disposed on the fluid inlet and outlet ports may help preserve the sterility of the inner volume of the cartridge prior to use, and can be removed before the cartridge is connected into a system with a fluid line that facilitates the flow of a body fluid from the subject to the cartridge and a fluid line that facilitates the flow of the body fluid from the cartridge back to the subject.

In certain embodiments, the cartridge comprises a label disposed on (for example, adhered to) an outer surface of the rigid housing. The label may comprise a lot number or bar code for identifying and/or tracking the cartridge.

2. System Configurations

It is understood that the SCD cartridges can be used in a variety of different fluid circuits depending upon the indication to be treated. See, for example, U.S. Pat. No. 8,251,941 and International application WO2012/051595.

In some embodiments, fluid circuits incorporating the SCD cartridge optionally can also perform other blood treatments. For example, fluid circuits optionally can further include additional devices that can filter, oxygenate, warm, or otherwise treat the blood before or after the blood enters the SCD cartridge. Moreover, the SCD cartridge and/or additional devices in a system can include more than one component for treating blood in other or complementary ways, for example, porous filters, oxygen pumps, and/or xenographic or allographic cells (for example, xenographic or allographic renal cells such as renal tubule cells). In certain embodiments, the SCD cartridge is free of such additional components. For example, a SCD cartridge may be free of cells such as xenographic or allographic cells (e.g., xenographic or allographic renal cells). These basic principles are described in more detail below.

The fluid circuits are configured to accomplish selective cytopheresis. In basic form, the system includes a SCD cartridge, a fluid connection for blood to flow from a blood source (for example, a subject, such as a patient) to the SCD cartridge, and a fluid connection for treated blood to flow from the SCD cartridge to a receptacle (for example, back to the subject). The SCD cartridge acts to sequester cells, for example, leukocytes, such as activated leukocytes, and facilitate inhibition of release of a pro-inflammatory substance from the leukocytes and/or deactivate the leukocytes. Sequestration of leukocytes can be achieved using the SCD cartridges described hereinabove. Inhibition of the release of a pro-inflammatory substance from the leukocytes and/or deactivation of the leukocytes can be achieved by any technique described in Section 3 below.

The leukocytes may become activated within the subject as result of a primary patient condition or secondary to other types of medical intervention, for example, during passage through a hemofilter (for example, as described hereinbelow, with reference to FIGS. 2C and 2D). The activated leukocytes then enter a SCD cartridge wherein the activated leukocytes are sequestered. In the case of the circuit in FIG. 2D, replacement fluid equal to the volume of the ultrafiltrate produced optionally is provided to the subject.

In other words, in the SCD cartridge, the activated leukocytes from the blood are sequestered, for example, by temporarily adhering to one or more surfaces inside the cartridge. Sequestration of the leukocytes can be achieved by a variety of approaches, for example, by association with molecules in a passageway or passageway region in the cartridge that bind leukocytes, for example, activated leukocytes, or by setting blood flow within the device to provide low shear stress on leukocytes, allowing them to associate with one or more surfaces inside the SCD cartridge. These sequestered leukocytes then are exposed to an agent, for example, citrate, to deactivate the leukocytes or inhibit their release of pro-inflammatory substances. The cartridges can also be used to sequester and deactivate other cell types, such as platelets.

It is believed that calcium chelators, for example, citrate, lead to a low $Ca_i$ environment in the cartridge thereby inhibiting release of a pro-inflammatory substance from the leukocytes and/or deactivating the leukocytes. Pro-inflammatory substances may include destructive enzymes and/or cytokines from the leukocytes. This inhibition and/or deactivation leads to an amelioration of the inflammatory state of the leukocytes. In this way, the SCD cartridge sequesters leukocytes, for example, neutrophils and monocytes, and inhibits release of a pro-inflammatory substance from the leukocytes and/or deactivates the leukocytes, for example, with citrate and/or a low-$Ca_i$ environment. The sequestration and inhibition and/or deactivation of platelets can be achieved in a similar fashion.

It has been demonstrated that the addition of a calcium chelator, e.g. citrate, to a device of the present invention including a housing containing hollow fibers that sequester leukocytes can improve myocardial function in a subject with myocardial dysfunction subsequent to infiltration by inflammatory immune cells. Accordingly, it is contemplated that the SCD cartridges of the invention can treat a variety of conditions associated with myocardial inflammation, such as chronic heart failure and acute decompensated heart failure by directly treating blood from the subject. After treatment, the blood is returned to the subject.

2.A. Single Device System

Figure 2A:
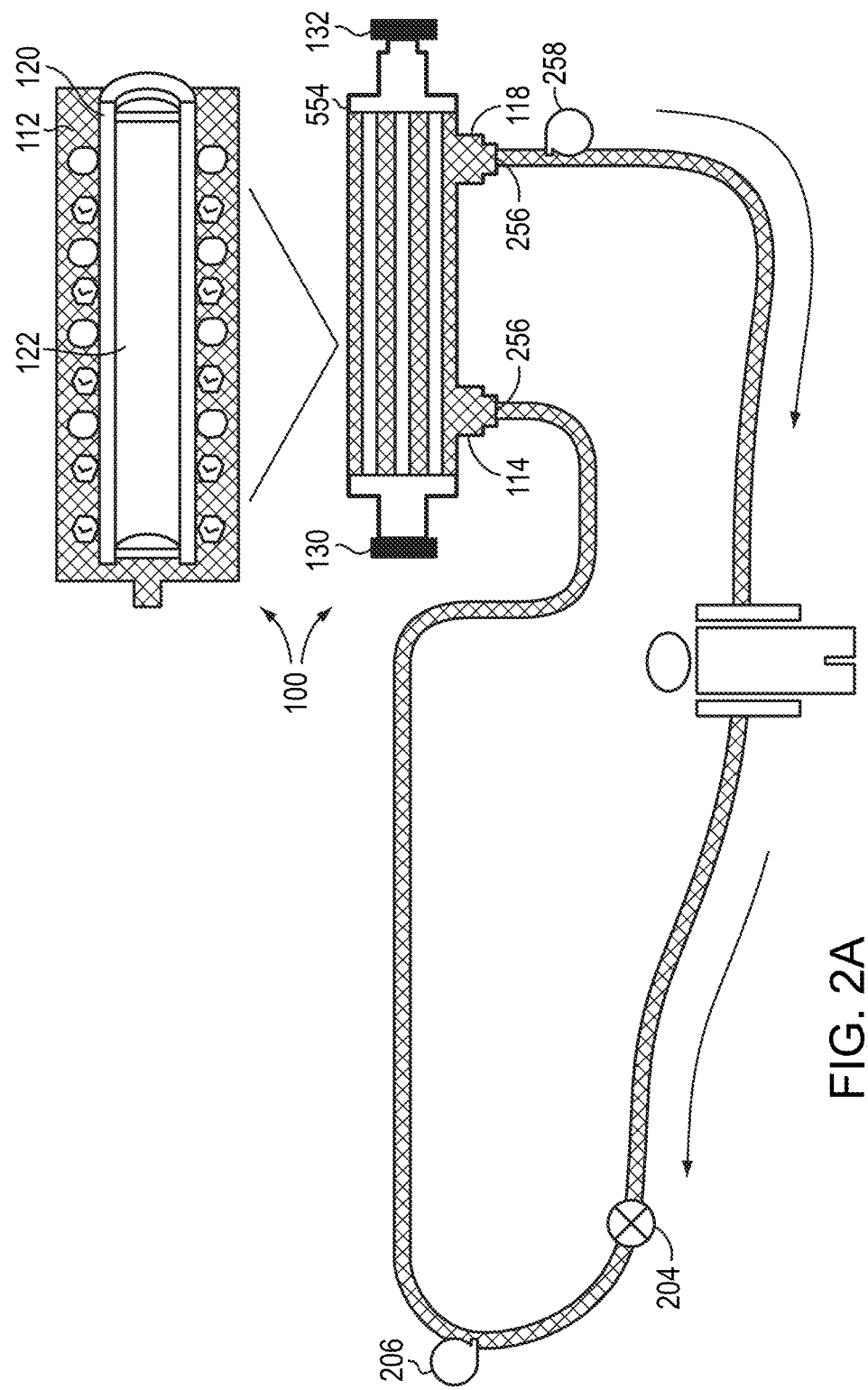
FIG. 2A is a schematic representation of a fluid circuit containing a SCD cartridge where the intracapillary space (ICS) has both ends capped.
Figure 2B:
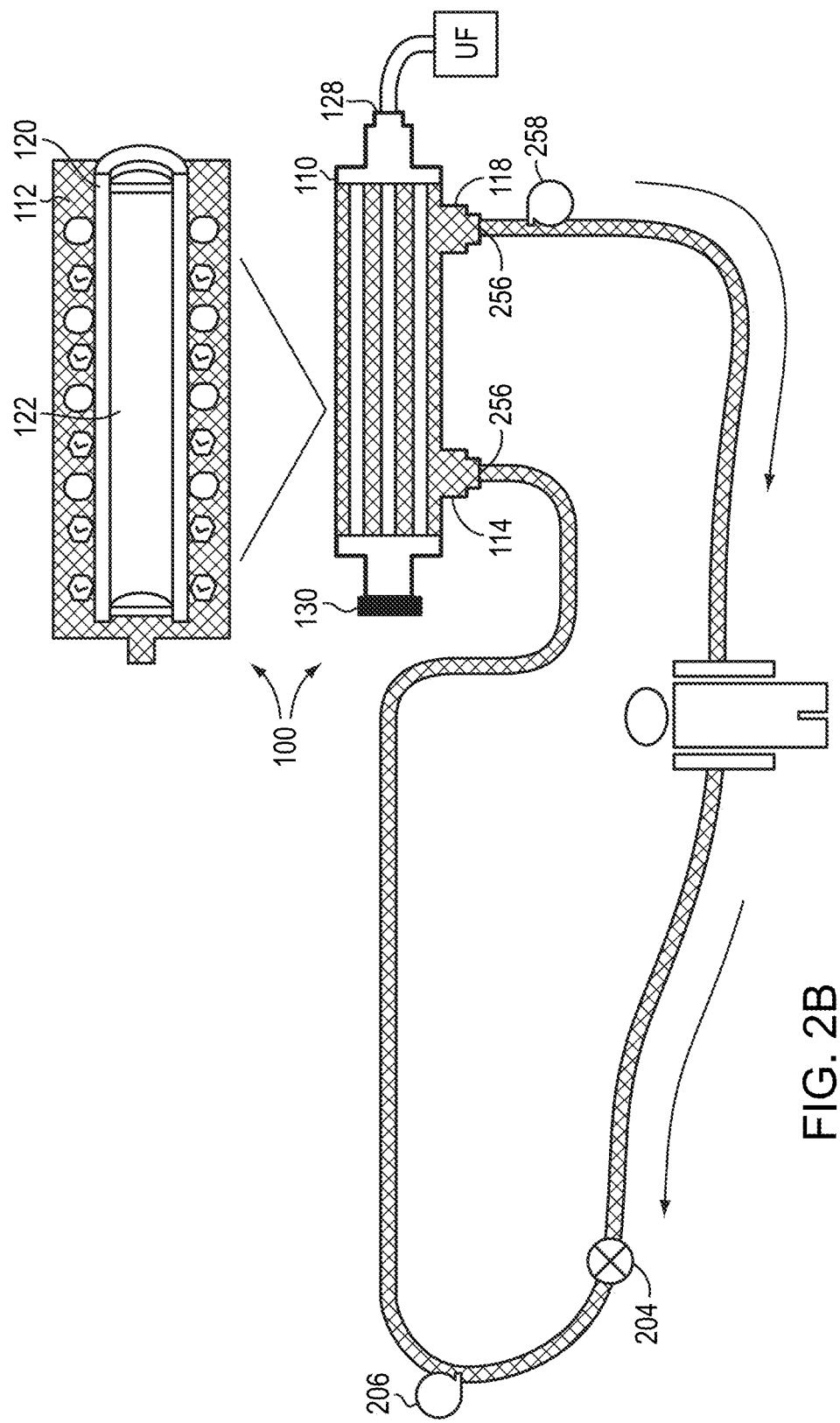
FIG. 2B is a schematic representation of an embodiment similar to FIG. 2A except that ultrafiltrate (UF) is collected from a SCD cartridge having only one end of the ICS capped.

As mentioned, a system can contain a SCD cartridge to accomplish selective cytopheresis and, optionally, other blood treatments without additional treatment devices in the system (see FIGS. 2A-2B). In one embodiment, such a SCD cartridge is shown schematically in FIG. 1A. During operation, leukocytes and/or platelets are sequestered within the SCD cartridge, for example, at the external surface of the hollow fibers, and exposed to an agent, for example citrate, capable of inhibiting release of a pro-inflammatory substance from a leukocyte and/or deactivating a leukocyte. The agent can be infused into a line upstream of the fluid inlet 114 or may be infused into the SCD itself via a port. Alternatively, or in addition, the SCD cartridge can be prepared with the agent prior to its use. Flow rates in the ECS are chosen in the ranges described herein such that there is a low shear force (in the ranges described herein) at the surface of the fiber to allow leukocytes to associate therewith. In this way, inhibition and/or deactivation of the leukocytes and/or platelets is achieved or initiated. Then, the blood in the ECS exits the SCD via fluid outlet 118, which enters into an outflow line.

FIG. 2A shows an exemplary SCD cartridge 100 of FIG. 1A in an exemplary fluid circuit. Body fluid, for example, blood, from a subject enters a blood line and is moved through that line via a pump 204. On the same blood line, a leukocyte inhibiting agent (e.g., citrate) can be infused at a port 206, optionally with a pump. The blood in the blood line then enters the inlet 114 and exits the SCD cartridge 100 at outlet 118. Blood lines at the inlet 114 and outlet 118, respectively, are attached using blood line connectors with locking mechanisms 256. Leukocytes are shown sequestered in the ECS 112 at the external surface of the solid support 120, which is depicted as a single hollow fiber. A blood outflow line from the outlet 118 returns blood to the subject. Another agent, such as calcium (e.g., calcium chloride or calcium gluconate), can be infused at a port 258 on this blood outflow line to prepare the blood for re-entry into the subject. In certain embodiments, the ICS can contain xenographic or allographic cells, for example, renal tubule cells, cultured in a monolayer on the lining of the ICS 122 of each fiber to further aid in treatment of the blood. However, in other embodiments, the ICS is cell-free. In one embodiment of the circuit of FIG. 2A, the lumen 122 of SCD cartridge 100 can be filled with saline.

The circuit of FIG. 2B includes the same components as FIG. 2A and operates in the same manner, except that FIG. 2B utilizes a SCD cartridge 100 in which ultrafiltrate is produced. The SCD cartridge 100 contains a plurality of porous membranes, which are hollow fibers. The luminal space within the fibers is the ICS 122 and the surrounding space outside the solid support 120 (depicted as hollow fibers) and within the SCD cartridge housing 110 is the ECS 112. Body fluid, for example, blood containing leukocytes enters the inlet 114 and moves into the ECS 112 surrounding the hollow fibers and exits at the outlet 118. Leukocyte sequestration and inhibition and/or deactivation can be achieved as described above. However, in this SCD, only the ICS inlet is capped with end cap 130. The ICS outlet 128 is not capped. Accordingly, depending on the characteristics of the porous hollow fibers (e.g., permeability and pore size), a portion of the blood in the ECS 112 can pass across the hollow fibers, and into the ICS 112 as ultrafiltrate (UF). A tube can be connected to the ICS outlet 128 for collecting ultrafiltrate (UF), which may be discarded as waste.

Flow rates and membrane characteristics for the embodiments shown in the circuits of FIGS. 2A-2B with the SCD of FIG. 1A can be as described below. For example, the ECS flow rate may be from about 100 mL/minute to about 500 mL/minute. The flow rate of the ultrafiltrate waste (e.g., for the SCD cartridge shown in FIG. 2B) may include, for example, flow rates from about 5 mL/minute to about 50 mL/minute. In the case of the circuit in FIG. 2B, replacement fluid equal in volume to the ultrafiltrate waster produced can optionally be added to the subject.

2.B. Selective Cytopheresis Inhibitory Device as Part of a Hemodialysis or Hemofiltration System As mentioned, in some embodiments the SCD cartridge can be part of a system with other devices for treating blood. For example, the SCD cartridge can be a part of a hemofiltration system, a hemodialysis system and/or a hemodiafiltration system that includes one or more filtration cartridges separate from the SCD cartridge within the system. When describing the part of the system that is not the SCD, the term "hemofiltration" can refer to hemodialysis, hemodiafiltration, hemofiltration, and/or hemoconcentration, and "hemofilter" can include a device (e.g., a cartridge) for performing one or more of hemodialysis, hemodiafiltration, hemofiltration, and/or hemoconcentration. The hemofiltration cartridge(s) can be configured to be in parallel or series with a SCD within an extracorporeal blood circuit, and associated blood pumps and tubing can be used to move the blood through the extracorporeal circuit.

Figure 2C:
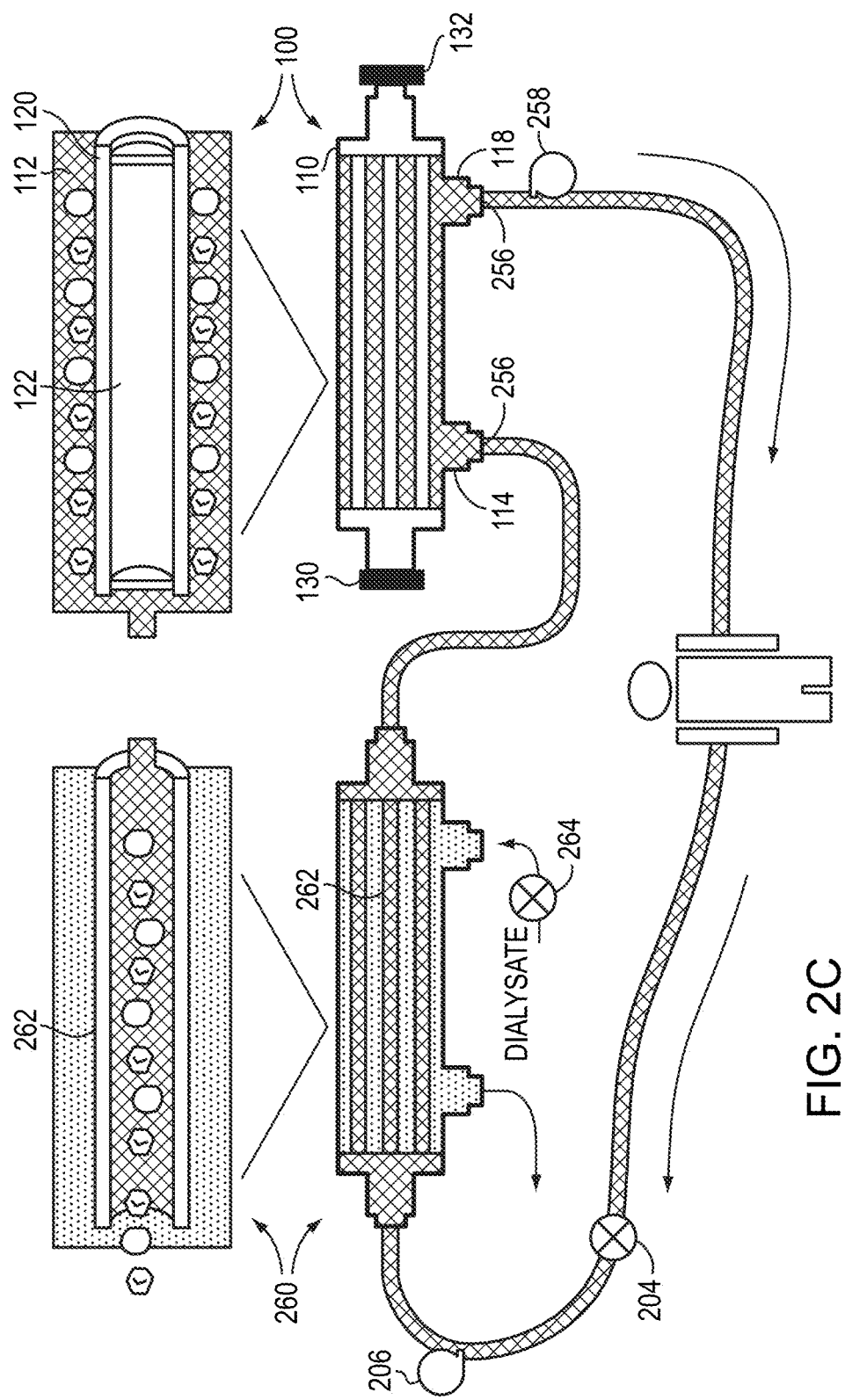
FIG. 2C is a schematic representation of an embodiment of a fluid circuit containing a first device, for example, a hemofiltration device, and a SCD cartridge that includes an ICS with both ends capped.
Figure 2D:
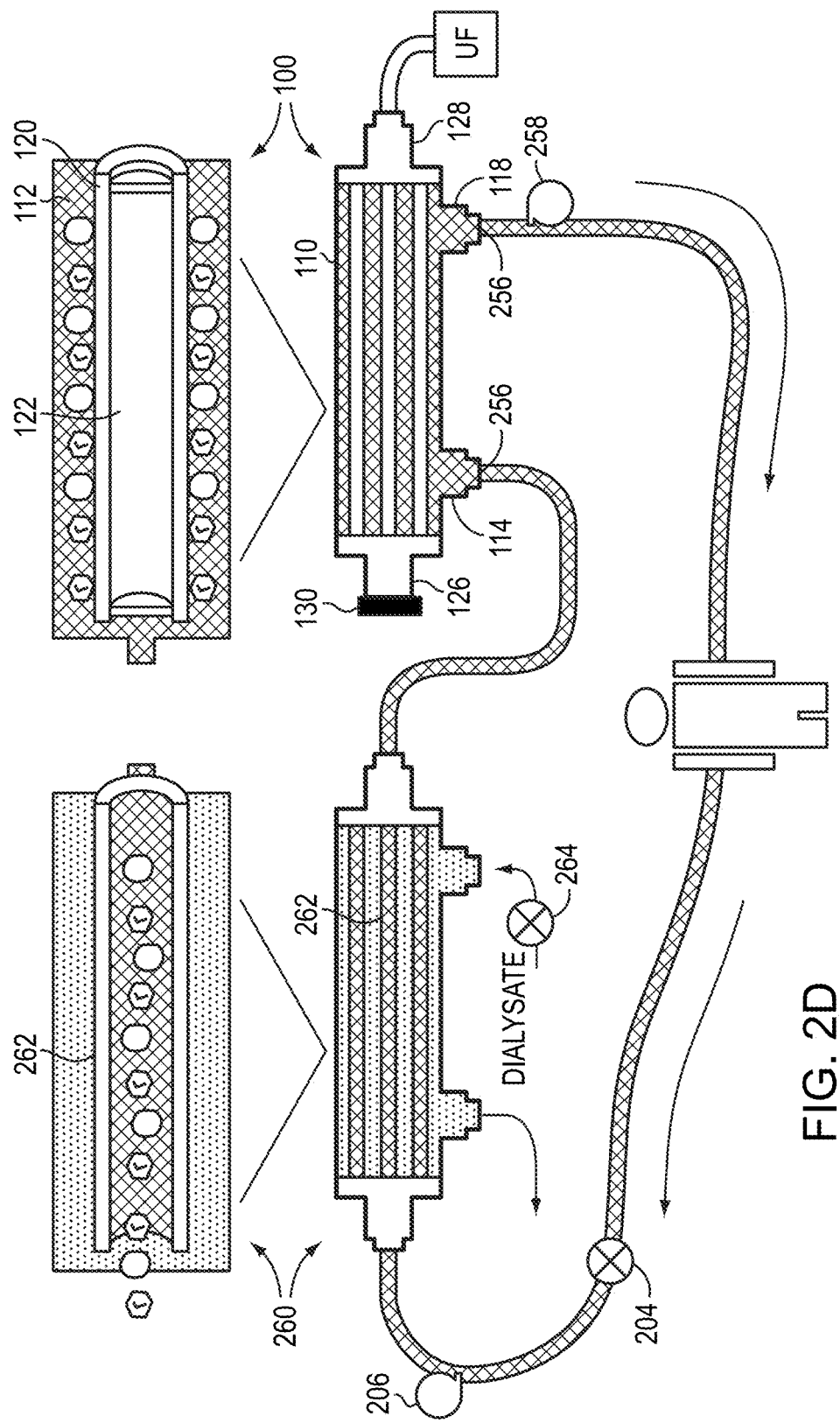
FIG. 2D is a schematic representation of an embodiment similar to FIG. 2C except that ultrafiltrate (UF) is collected from the SCD cartridge where only one end of the ICS is capped.

For example, as shown in FIGS. 2C and 2D, blood flows from a subject through a blood line. The blood is moved through the blood line via a pump 204. A leukocyte inhibiting agent (e.g., citrate) can be infused into the same blood line at a port 206, optionally with a pump before entering a conventional hemofilter 260. The blood then flows through hollow fibers 262 in hemofilter 260. Dialysate is infused into the ECS surrounding the hollow fibers 262 and within the housing of hemofilter 260, and dialysis occurs with solutes being removed as "waste" from the blood across the hemofilter filtration membrane 262 (the hollow fibers) and into the dialysate. The dialysate flows in a counter current fashion relative to the blood, and the dialysate is moved with a dialysate pump 264. Additionally, molecules and fluid from the blood can pass across the hemofilter filtration membrane 262 (the hollow fibers) as ultrafiltrate, depending on the pore size through the membrane.

The exemplary system of FIG. 2C shows a circuit with the SCD cartridge 100 of FIG. 1A, in which the ICS inlet and outlet ports have been capped with end caps. Blood exits the hemofilter 260 and enters the SCD cartridge 100 at the inlet 114. The blood then is processed through the SCD cartridge, which sequesters leukocytes on the solid support 120 (depicted as hollow fibers) and inhibits release of a pro-inflammatory substance from a leukocyte and/or deactivates a leukocyte in the manner described for FIGS. 2A-2B, above. The blood lines into and out of the SCD cartridge 100 are attached using a connection with a locking mechanism 256. The blood then is returned to the subject via a blood outflow line from the outlet 118. Another agent, such as calcium, can be infused at a port 258 on this blood outflow line in order to prepare the blood for re-entry into the subject. In certain embodiments, the intracapillary space (ICS) of the SCD can contain xenographic or allographic cells, for example, renal tubule cells, cultured in a monolayer on the lining of the lumen of each fiber to further aid in treatment of the blood. However, in other embodiments the ICS is cell free. In certain embodiments of the fluid circuit shown FIG. 2C, the ICS 122 of the SCD 100 is filled with saline and the end ports of the ICS are capped with end caps 130 and 132.

The circuit of FIG. 2D includes the same components as FIG. 2C and operates in the same manner, except that FIG. 2D utilizes a SCD cartridge 100 that produces ultrafiltrate (i.e., the ICS outlet port is not capped with end caps). The flow of body fluid (e.g., blood) through the SCD cartridge 100 is described above in the context of FIG. 2B. Additionally, SCD cartridge 100 functions as described above, in the context of FIG. 2B. As noted above, SCD cartridge 100 has only the ICS inlet 126 capped with end cap 130. The ICS outlet 128 is not capped with an end cap. Accordingly, depending on the characteristics of the porous hollow fibers, a portion of the blood in the ECS 112 can pass across the hollow fibers, and into the ICS as ultrafiltrate (UF). A tube can be connected to the ICS outlet 128 for collecting ultrafiltrate (UF), which may be discarded as waste.

Without wishing to be bound by theory, it is contemplated that the flow geometry in these embodiments of the SCD system (and those shown in FIGS. 2A-2D and 3A and 3B) allows leukocytes to exist in a low shear force environment in the ECS of the SCD cartridge and, therefore, associate with one or more internal surfaces in the SCD cartridge, for example, the hollow fibers. Conversely, in a typical use of a hemofiltration cartridge (for example, the first device 260 in the circuits of FIGS. 2C and 2D), blood flow through the small diameter lumens of the hollow fibers yields a higher shear force (than that in the SCD) that prevents association of leukocytes with the hollow fibers and sequestration of leukocytes within the device. Accordingly, a hemofiltration device having the conventional flow circuit supporting its operation reversed (i.e., blood flowing outside the hollow fibers rather than inside the hollow fibers) can act as a SCD to sequester potentially damaging and circulating activated leukocytes. These sequestered leukocytes can be treated with a leukocyte inhibiting agent (e.g. citrate).

Further, it is contemplated that the inflammatory response of sequestered leukocytes is inhibited and/or deactivated in the presence of low $Ca_i$ (caused, for example, by citrate) before, during, and/or after sequestration. The low-$Ca_i$ environment may inhibit the inflammatory activity of, or deactivate, the leukocytes.

In certain embodiments, the circuit of FIG. 2D can be modified such that the dialysate produced by hemofilter 260 can be introduced into the ICS of SCD cartridge 100 via ICS inlet 126. Although the ICS can be cell free, it is understood that this system optionally also can include cells within the ICS 122, for example, renal tubule cells. The rate of the blood flow is chosen to have a sufficiently low shear force (in the ranges described herein) at the surface of the porous, hollow fibers to allow sequestration of leukocytes by association with the fibers, for example at a blood flow rate from about 100 mL/minute to about 500 mL/minute. Alternatively, the blood flow rate through the extracorporeal circuit, through the lumens of the hollow fibers in the hemofilter 260, and through the ECS 112 of the SCD cartridge 100 can be about 120 mL/minute. The ultrafiltrate can be moved at rates in the ranges described herein, for example, at flow rates less than about 50 mL/minute, from about 5 mL/minute to about 50 mL/minute, and from about 10 mL/minute to about 20 mL/minute. Alternatively, the ultrafiltrate flow rate can be maintained at 15 mL/minute. Optionally, a balanced electrolyte replacement solution (e.g., a solution containing bicarbonate base) can be infused into the bloodline on a 1:1 volume replacement for ultrafiltrate produced. The fluid (e.g., ultrafiltrate) and blood (or leukocyte-containing fluid) can flow in the same direction or in opposite directions.

In this and other embodiments, the blood flow configuration through the SCD cartridge is opposite the blood flow configuration through a typical hemofiltration cartridge. That is, blood flows through the interior of the hollow fibers of the hemofiltration cartridge in its intended use versus around the outside of the hollow fibers of the SCD cartridge. This unconventional blood flow configuration through the SCD cartridge allows for a lower shear force within the ECS at the exterior surface of the hollow fiber relative to the higher shear force within the lumen of the hollow fibers of a hemofilter, thus facilitating sequestration of leukocytes in the ECS of the SCD. Conversely, the blood flow through the interior of the hollow fibers of the hemofilter prohibits leukocyte sequestration due to high shear force created by blood flowing through the small diameter lumens of the hollow fibers. For example, the passage of blood within the interior of a hollow fiber of a hemofilter can create a shear force of $1.5 \times 10^7$ dynes/$cm^2$ whereas blood flow through the ECS of certain embodiments of a SCD creates a shear force of 10 dynes/$cm^2$, or about $10^6$ less shear force. For comparison, the shear force at a typical arterial wall is 6 to 40 dynes/$cm^2$ and the shear force at a typical vein wall is 1-5 dynes/$cm^2$. Thus, a capillary wall has a shear stress of less than 5 dynes/$cm^2$.

Accordingly, use of the SCD cartridge uses a sufficiently low shear force at a surface in a region of a passageway configured to sequester leukocytes to be able to associate leukocytes with that surface and sequester leukocytes, such as activated leukocytes in the region. For example, in some embodiments a shear force of less than 1000 dynes/$cm^2$, or less than 500 dynes/$cm^2$, or less than 100 dynes/$cm^2$, or less than 80 dynes/$cm^2$, or less than 60 dynes/$cm^2$, or less than 40 dynes/$cm^2$, or less than 20 dynes/$cm^2$, or less than 10 dynes/$cm^2$, or less than 5 dynes/$cm^2$, is useful at a surface in the passageway region configured to sequester leukocytes. It should be understood that these shear forces may be useful in any of the SCD embodiments described herein. In certain embodiments, having two devices, such as a hemofilter and a SCD, the difference in shear force between blood flowing in the hemofilter and blood flowing in the SCD can be at least 1000 dynes/$cm^2$.

In these and other embodiments, so long as the unconventional flow configuration is followed (i.e., blood flows outside of the hollow fibers, rather than inside the hollow fibers) to yield the requisite shear force, the SCD can be comprised of a conventional (e.g., Model F-80A, Fresenius Medical Care North America, Waltham, Mass., U.S.A.), which is approved by the FDA for use in acute and chronic hemodialysis. Similarly, the extracorporeal perfusion circuit of this or any other embodiment can use standard dialysis arteriovenous blood tubing. The cartridges and blood tubing can be placed in any dialysate delivery pump system (e.g., Fresenius 2008H) that is currently in use for chronic dialysis.

In one exemplary system, the system includes tubing leading from a subject (a blood line) with a bag of a citrate solution infused into the tubing by an infuser. A first F-40 hemofilter cartridge (Fresenius Medical Care North America, Waltham, Mass., U.S.A.) is connected with the blood line at a point after the citrate enters the blood line. Blood in the blood line then flows through the interior of hollow fibers (the ICS) inside the cartridge, from an end port inlet to an end port outlet, and dialysate flows outside these hollow fibers and within the cartridge (the ECS) from one side port to a second side port in a countercurrent manner with respect to the blood flow. A dialysate/ultrafiltrate mixture exiting from the second side port is collected. Substantially no blood cells, platelets, or plasma cross from the ICS to the ECS, and substantially no leukocytes adhere to the interior of the hollow fibers. The hollow fibers are disposed parallel to one another in a bundle, and each fiber has a diameter of approximately 240 micrometers. Furthermore, the pores of the hollow fibers are small enough to prevent passage of albumin, a molecule of about 30 angstroms, through the fibers, and the pores are generally this size across the entire fiber. The filtered blood then continues from the end port outlet, through tubing, to a side port inlet of an F-80A-based cartridge (Fresenius Medical Care North America, Waltham, Mass., U.S.A.), which operates as a SCD cartridge. The blood flows through the ECS of the F-80A-based cartridge and exits the cartridge at a side port outlet. Any ultrafiltrate that is produced in the F-80A-based cartridge enters the ICS and exits through an end port. The other end port of the cartridge is capped. Substantially no blood cells, platelets, or plasma cross from the ECS to the ICS, and leukocytes adhere to the exterior of the hollow fibers for some period of time. Blood exiting the F-80A cartridge enters tubing where a calcium solution is infused into the blood using an infuser. Finally, the tubing returns the processed blood to the subject. In certain embodiments, the blood flow rate in the system does not exceed 500 mL/minute, and blood does not displace air in the system at any point. Additionally, the pumping and infusion rates can be manually changed in view of bedside readings of electrolytes and white blood cell counts. An i-STAT® handheld monitoring device produces these readings from a small amount of blood withdrawn from the subject.

It is contemplated that the risk of using such a system is similar to the risk associated with hemodialysis treatment and includes, for example, clotting of the perfusion circuit, air entry into the circuit, catheter or blood tubing kinking or disconnection, and temperature dysregulation. However, dialysis machines and associated dialysis blood perfusion sets have been designed to identify these problems during treatment with alarm systems and to mitigate any clot or air embolism to the subject with clot filters and air bubble traps. These pump systems and blood tubing sets are FDA approved for this treatment indication.

As mentioned above, infusion of a leukocyte inhibition agent, for example, citrate, can be local to the SCD, regional, or throughout the system. In this or any embodiment, citrate can also be used as an anti-clotting agent, in which case perfusion throughout the system would be useful. Clinical experiences suggest that if clotting occurs within a hemofiltration system, it is initiated in the first dialysis cartridge. Anticoagulation protocols, such as systemic heparin or regional citrate, are currently established and routinely used in clinical hemodialysis.

Figure 3A:
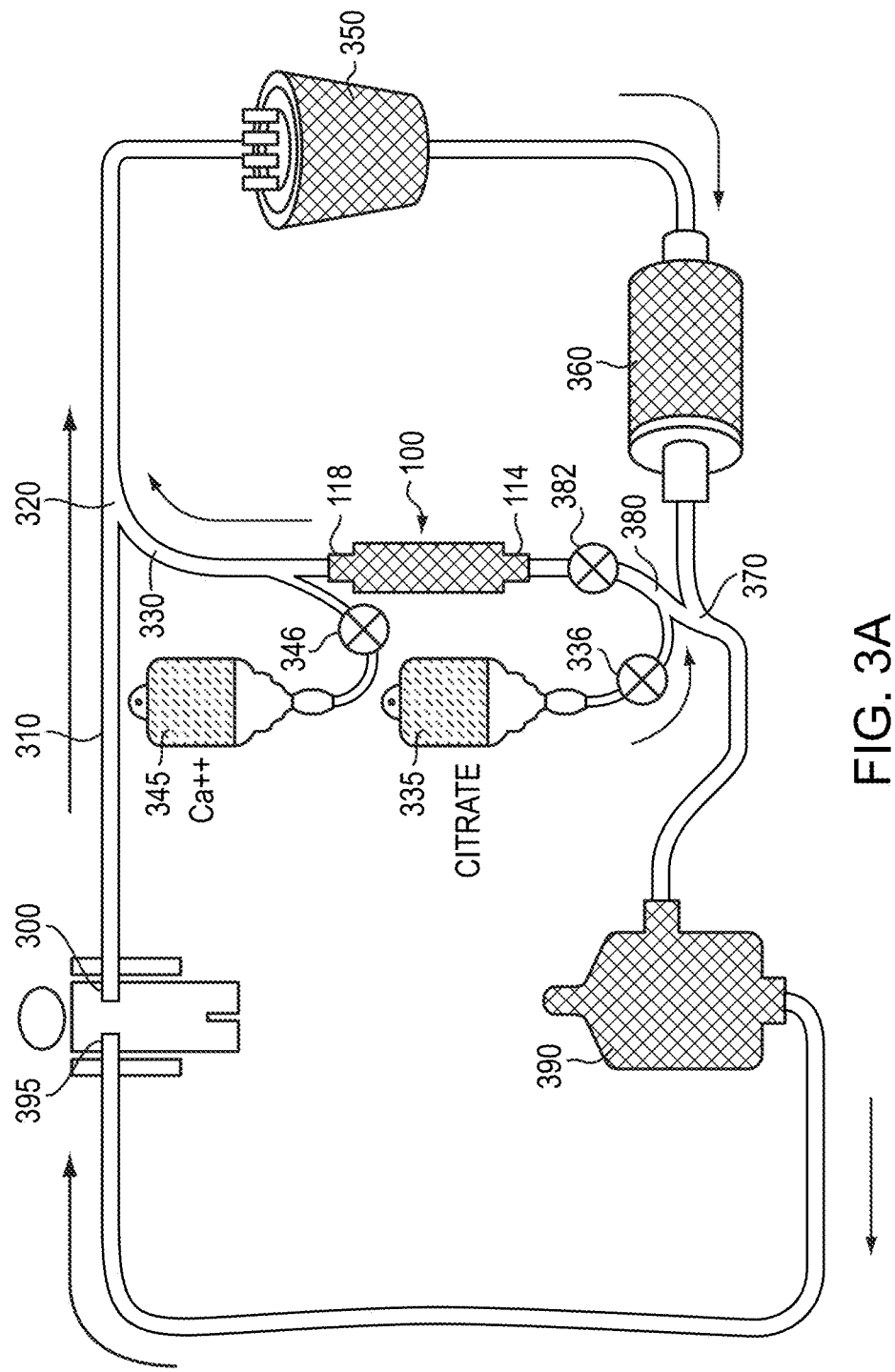
FIGS. 3A and 3B are schematic representations of embodiments of system configurations that can be used as a CPB circuit.
Figure 3B:
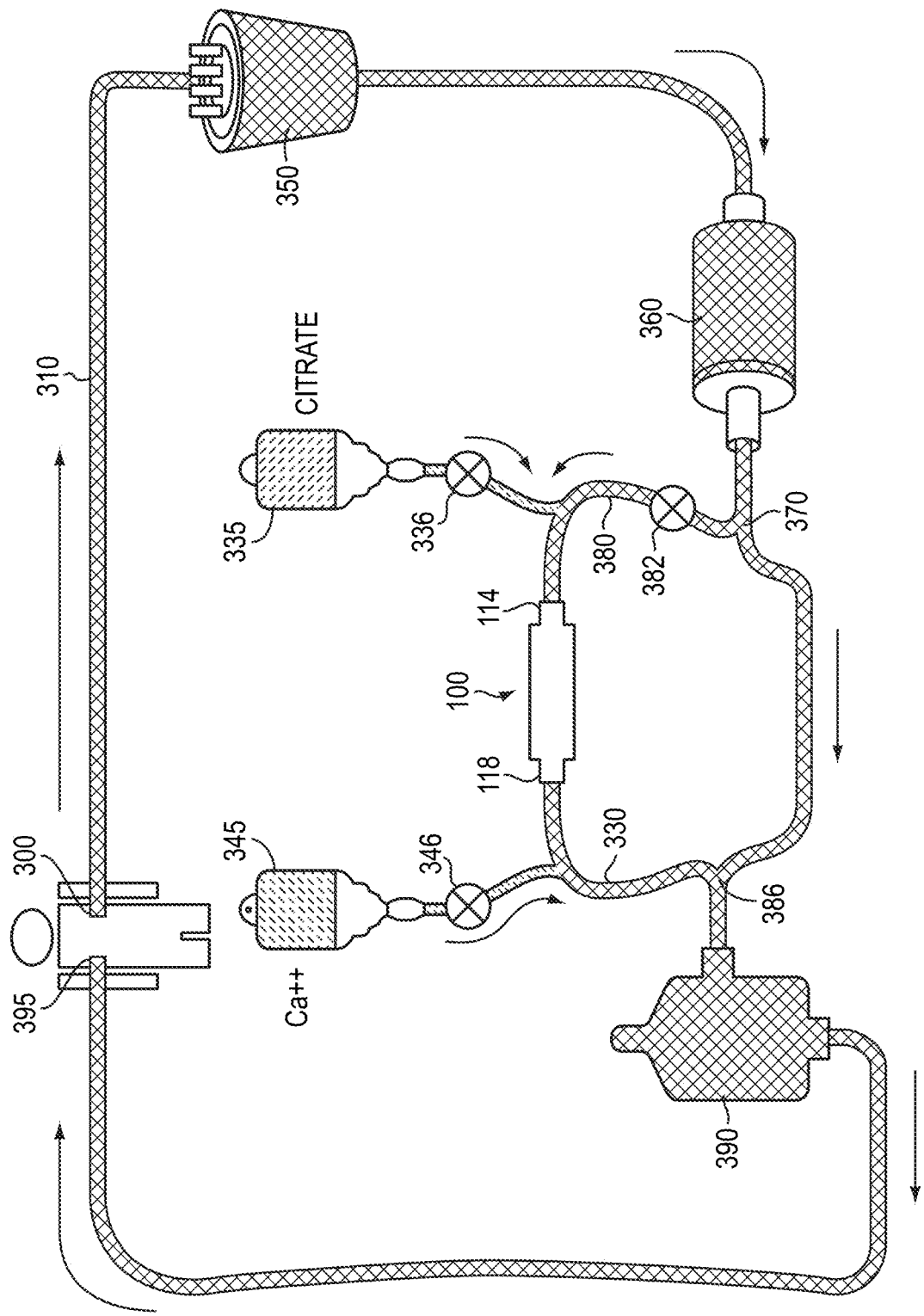

2.C. Selective Cytopheresis Inhibitory Device as Part of a Cardiopulmonary Bypass System As shown in FIGS. 3A-3B, a SCD cartridge can be used within a cardiopulmonary bypass (CPB) circuit to treat and/or prevent inflammatory conditions secondary to surgeries (e.g., bypass surgery). FIGS. 3A and 3B show the SCD cartridge of FIG. 1A in exemplary CPB systems. CPB is used to divert blood from both the left and right sides of the heart and lungs. This is achieved by draining blood from the right side of the heart and perfusing the arterial circulation. However, since systemic-to-pulmonary collaterals, systemic-to-systemic collaterals, and surgical site bleeding return blood to the left side of the heart, special drainage mechanisms of the left side of the heart are required during CPB. Optionally, cardioplegia can be delivered through a special pump and tubing mechanism. A standard CPB system has several features that can be broadly classified into three subsystems. The first subsystem is an oxygenating-ventilating subsystem that supplies oxygen and removes carbon dioxide from the blood. The second subsystem is a temperature control system. The third subsystem includes in-line monitors and safety devices.

As shown in the embodiment of FIG. 3A, blood is moved via a venous cannula 300 from a subject into a blood line 310. Blood flows through the blood line 310, passing a recirculation junction 320, which is connected to a SCD outflow line 330. The SCD outflow line 330 contains blood treated by the SCD device 100. The blood in the blood line 310 mixes with the SCD-treated blood and continues to a venous reservoir 350 and onto an oxygenator 360 where the blood is oxygenated. The oxygenated blood then flows from the oxygenator 360 to a junction 370 with a SCD inflow line 380. Here, where a portion of the blood in the blood line 310 is diverted to the SCD 100 via the SCD inflow line 380 for treatment by the SCD cartridge 100. The flow of blood through the SCD inflow line 380 is controlled by a pump 382. The SCD cartridge 100 is designed to sequester select cells associated with inflammation, for example, leukocytes or platelets. Blood containing leukocytes enters the inlet 114 and moves into the ECS 112 (see in FIG. 1A) surrounding the hollow fibers. Leukocytes are sequestered in the device, for example, on the fluid contacting surface of solid support 120 (see in FIG. 1A) (i.e., the exterior surface of the hollow fibers). Flow rates at pump 382 can be chosen at ranges described herein such that there is a low shear force (in the ranges described herein) at the surface of the hollow fibers to allow leukocytes to associate therewith. Blood in the ECS 112 (see in FIG. 1A) exits the SCD via outlet 118 and enters the SCD outflow line 330. At junction 370, a portion of the blood in the blood line 310 also continues to an arterial filter/bubble trap 390, before being returned to the subject at an arterial cannula 395.

Although no agents need be added to the blood, in one embodiment, a citrate feed 335 and citrate pump 336 add citrate to the blood in the SCD inflow line 380 and a calcium feed 345 and calcium pump 346 add calcium to the blood in the SCD outflow line 330. Citrate (or another leukocyte inhibiting agent described herein) is added to the blood flowing into the SCD cartridge 100 from the citrate feed 335 to inhibit and/or deactivate cells associated with inflammation, such as leukocytes. Calcium can be added back into the blood to prepare the blood for reentry into the subject.

The circuit shown in FIG. 3B is different from the circuit of FIG. 3A in that it does not recirculate blood within the circuit, for example, at a recirculation junction 320 (see, FIG. 3A). Rather, as shown in FIG. 3B, blood is moved via the venous cannula 300 from a subject into the blood line 310, where the blood flows directly to the venous reservoir 350 and onto an oxygenator 360 where the blood is oxygenated. The oxygenated blood then flows from the oxygenator 360 to the junction 370 with the SCD inflow line 380. Here, a portion of the blood in the blood line 310 is diverted to the SCD cartridge 100 via the SCD inflow line 380 for sequestration of leukocytes by the SCD cartridge 100, as described above for FIG. 3A. Blood exiting the SCD cartridge 100 enters the SCD outflow line 330 and mixes with oxygenated blood at junction 386. After blood from the SCD cartridge mixes with blood in the blood line 310 it continues in the blood line 310 to the arterial filter/bubble trap 390, before being returned to the subject at the arterial cannula 395.

A citrate feed 335 and citrate pump 336 to add citrate to the blood in the SCD inflow line 380 and a calcium feed 345 and calcium pump 346 to add calcium to the blood in the SCD outflow line 330. As described for FIG. 3A, citrate or any other leukocyte inhibiting agent is added to the blood from the citrate feed 335 to inhibit and/or deactivate cells associated with inflammation, such as leukocytes. Calcium can be added back into the blood to prepare the blood for reentry into the subject.

2.D. Additional Features of Selective Cytopheresis Inhibitory Devices

In some embodiments, the SCD cartridges are configured for treating and/or preventing a certain disorder. It is understood, however, that a number of different configurations can be used to treat and/or prevent a particular disorder.

Moreover, the SCD cartridge can be oriented horizontally or vertically and placed in a temperature controlled environment. The temperature of a SCD cartridge containing cells preferably is maintained at about 37° C. to about 38° C. throughout the SCD's operation to ensure optimal function of the cells in the SCD cartridge. For example, but without limitation, a warming blanket may be used to keep the SCD cartridge at the appropriate temperature. If other devices are utilized in the system, different temperatures may be needed for optimal performance.

In some embodiments, the SCD cartridges and/or the fluid circuits incorporating the SCD cartridges are controlled by a processor (e.g., computer software). In such embodiments, a device can be configured to detect changes in activated leukocyte levels within a subject and provide such information to the processor (e.g., information relating to leukocyte levels and/or increased risk for developing an inflammation disorder). In some embodiments, when a certain activated leukocyte level is reached or a subject is deemed at a certain risk for developing an inflammation disorder (e.g., SIRS), the subject's blood is processed through a SCD for purposes of reducing the possibility of developing an inflammation disorder. In some embodiments, the fluid circuit can automatically process the subject's blood through the SCD in response to these measurements. In other embodiments, a health professional is alerted to the elevated leukocyte level or increased risk within the subject, and the professional initiates the treatment.

It is contemplated that the cartridges of the present invention can be included with various kits or systems. For example, the kits or systems may include the SCD cartridges of the present invention, leukocyte inhibiting agents (e.g., calcium chelating agents, such as citrate), allographic cells (e.g., renal tubule cells), or other parts. Additionally, the SCD cartridges may be combined with various surgical instruments necessary for implanting the filtration device into a subject.

4. Inhibition and/or Deactivation of Cells Associated with Inflammation

The SCD cartridges are configured, and the methods of the present invention when performed inhibit release of a pro-inflammatory substance from leukocytes and/or deactivate leukocytes, such as activated leukocytes, in a subject's blood such that an inflammatory response within the subject is prevented and/or diminished. Various techniques can be used. For example, in some embodiments, the SCD cartridges and the fluid circuits incorporating one or more of the SCD cartridges can inhibit release of a pro-inflammatory substance from a leukocyte and/or deactivate a leukocyte by exposing the leukocytes (e.g., sequestered activated and/or primed leukocytes) to leukocyte inhibiting agents. A leukocyte inhibiting agent can be bound, covalently or non-covalently, to a fluid contacting surface of the SCD cartridge, for example, a hollow fiber. Additionally or alternatively, a leukocyte inhibiting agent can be infused into the SCD cartridge or a circuit incorporating a SCD cartridge before, during, or after sequestration of the leukocytes, for example, at or near a membrane surface.

The present invention is not limited to a particular type or kind of leukocyte inhibiting agent. Leukocyte inhibiting agents include, for example, anti-inflammatory biological agents, anti-inflammatory small molecules, anti-inflammatory drugs, anti-inflammatory cells, and anti-inflammatory membranes. In some embodiments, the leukocyte inhibiting agent is any material or compound capable of inhibiting activated leukocyte activity including, but not limited to, non-steroidal anti-inflammatory drugs (NSAIDs), anti-cytokines, imatinib mesylate, sorafenib, sunitinib malate, anti-chemokines, immunosuppressant agents, serine leukocyte inhibitors, nitric oxide, polymorphonuclear leukocyte inhibitor factor, secretory leukocyte inhibitor, and calcium chelating agents. Examples of calcium chelating agents include, but are not limited to, citrate, sodium hexametaphosphate, ethylene diamine tetra-acetic acid (EDTA), triethylene tetramine, diethylene triamine, o-phenanthroline, oxalic acid and the like. The leukocyte inhibiting agent can be any protein or peptide known to inhibit leukocytes or immune cells including, but not limited to, angiogenin, MARCKS, MANS, Complement Factor D, the disulfide C39-C92 containing tryptic angiogenin fragment LHGGSPWPPC$^{92}$QYRGLTSPC$^{39}$K (SEQ ID NO: 1) and synthetic homologs of the same; the agent also can be those proteins, peptides, and homologs reported by Tschesche et al. (1994) J. BIOL. CHEM. 269(48): 30274-80, Horl et al. (1990) PNAS USA 87: 6353-57, Takashi et al. (2006) AM. J. RESPIRAT. CELL AND MOLEC. BIOL. 34: 647-652, and Balke et al. (1995) FEBS LETTERS 371: 300-302, that may facilitate inhibition of release of a pro-inflammatory substance from a leukocyte and/or deactivate a leukocyte. Moreover, the leukocyte inhibiting agent can be any nucleic acid known to inhibit release of a pro-inflammatory substance from the leukocyte and/or deactivate the leukocyte. The leukocyte inhibiting agent can be in solution or lyophilized.

Any amount or concentration of leukocyte inhibiting agent can be used to inhibit the release of pro-inflammatory substances from a leukocyte and/or deactivate the leukocyte. The leukocyte inhibiting agent can be introduced into a passageway, passageway region, device, device region, or system region of a system by any methods known in the art. For example, the leukocyte inhibiting agent can be infused at a port. The amount of leukocyte inhibiting agent infused in a passageway can be sufficient to inhibit release of a pro-inflammatory substance from a leukocyte and/or deactivate a leukocyte sequestered within the same passageway or within an adjacent passageway. In some embodiments, a leukocyte inhibiting agent, for example, citrate, can be infused into the system, a region of the system, or one or more devices within the system, including devices that perform other functions and do not sequester leukocytes. More particularly, the leukocyte inhibiting agent (e.g. citrate) can be infused upstream from, into, or downstream from a passageway that sequesters leukocytes. Alternatively, the leukocyte inhibiting agent can be contained in one or more passageways, passageway regions, devices, or system regions within a system. For example, a leukocyte inhibiting agent can be bound to a surface in the passageway configured to sequester leukocytes, or in another passageway, in an amount sufficient to inhibit release of a pro-inflammatory substance from the leukocytes and/or deactivate the leukocytes.

The inhibition of release of a pro-inflammatory substance from a leukocyte and/or deactivation of a leukocyte can occur temporally before, during, and/or after sequestration of the leukocyte. Moreover, the leukocyte can remain inhibited or deactivated for a period of time following sequestration. In certain embodiments, a leukocyte can be inhibited or deactivated during the period of time that the leukocyte is exposed to a target concentration of a leukocyte inhibiting agent or is exposed to a target concentration of $Ca_i$ (typically from about 0.20 mmol/L to about 0.40 mmol/L) that results from exposure to a leukocyte inhibiting agent such as citrate. The period of time that the leukocyte is exposed to the target concentration of leukocyte inhibiting agent or target concentration of $Ca_i$ can precede, include, and/or follow the period of time that the leukocyte is sequestered. In certain embodiments, the leukocyte can continue to become or remain inhibited or deactivated for a period of time following exposure to the leukocyte inhibiting agent.

The time of exposure to the leukocyte inhibiting agent can vary depending upon the agent used, the extent of leukocyte activation, the extent of production of pro-inflammatory substances, and/or the degree to which the inflammatory condition has compromised patient health. Exposure can be, for example, from 1 to 59 seconds, from 1 to 59 minutes, from 1 to 24 hours, from 1 to 7 days, one or more weeks, one or more months, or one year or more. In certain embodiments, the leukocytes treated (for example, are permitted to be sequestered by the cartridge and/or exposed to the leukocyte inhibiting agent (for example, a calcium chelating agent) over a period of at least 2 hours, at least 4 hours, at least 6 hours, at least 8 hours, or at least 12 hours. In certain embodiments, the leukocytes from the subject are treated over a period of 2 to 24 hours, 2 to 12 hours, 4 to 24 hours, or 4 to 12 hours.

The leukocyte inhibiting agent can be applied to the system before or during operation the system. In certain embodiments, the leukocyte inhibiting agent is applied during operation of the system and the amount of leukocyte inhibiting agent applied to the system is monitored.

In some embodiments, a leukocyte inhibiting agent can be titrated into the system (e.g., at a port 206 as shown in FIGS. 2A-2D or from a feed 335 and pump 336 as shown in FIGS. 3A and 3B). The titration can be adjusted relative to a monitored blood characteristic. For example, citrate can be titrated into the system to keep the $Ca_i$ in the blood at a certain level, for example, at a $Ca_i$ concentration of about 0.2 to about 0.4 mmol/L. Any type of citrate that is biologically compatible can be used, for example, 0.67% trisodium citrate or 0.5% trisodium citrate. See, e.g., Tolwani et al. (2006) CLIN. J. AM. SOC. NEPHROL. 1: 79-87. In some embodiments, a second solution can be added into the system following inhibition of the release of pro-inflammatory substances from a leukocyte and/or deactivation of the leukocyte (e.g., at port 258 as shown in FIGS. 2A-2D, or from a feed 335 and pump 336 as shown in FIGS. 3A and 3B), to readjust the blood for reentry into the subject. For example, in embodiments in which a calcium chelating agent is used as the leukocyte inhibiting agent, calcium can be added back into the blood before reentry into the subject.

In one embodiment, a 1000 mL bag containing a citrate solution, for example ACD-A (Baxter Fenwal, Chicago Ill.; contents per 100 mL: dextrose 2.45 g, sodium citrate 2.2 g, citric acid 730 mg, pH 4.5-5.5 at 25° C.) can be attached to an infusion pump and then attached to an arterial line (outflow from subject to devices) of the system (e.g. at port 206; the outflow from a subject in a CPB situation is called a venous line, and infusion occurs from, for example, the feed 335 and pump 336). A negative pressure valve can be employed to facilitate citrate pump function (infusing into a negative pressure area proximal to the blood pump). The initial rate of citrate infusion can be constant, for example, about 1.5 times, in mL/hour, the blood flow rate, in mL/minute (e.g., if the blood flow rate is about 200 mL/minute, then the initial constant rate of citrate infusion may be about 300 mL/hour). In addition, a calcium chloride infusion at a concentration of about 20 mg/mL may be added near the venous port of the system (e.g., port 258 of FIGS. 2A-2D); the analogous location in the CPB situation is shown as a feed 335 and pump 336 in FIGS. 3A and 3B). The initial calcium infusion can be set at 10% of the citrate infusion rate (e.g., 30 mL/hour). The $Ca_i$ can be monitored continuously or at various times, for example, every two hours for the first eight hours, then every four hours for the next sixteen hours, then every six to eight hours thereafter. The monitoring can be increased as needed and can be monitored at more than one location in the system, for example, after citrate infusion and after calcium infusion.

Exemplary citrate and calcium chloride titration protocols are shown in Table 3 and in Table 4, respectively. In this embodiment, the target $Ca_i$ range in the SCD is from about 0.20 mmol/L to about 0.40 mmol/L, with the $Ca_i$ target concentration achieved by infusion of citrate (e.g., ACD-A citrate solution). As this is a dynamic process, the rate of citrate infusion may need to be changed to achieve the target $Ca_i$ range in the SCD. The protocol for doing so is shown below, with infusion occurring at the infusion points described above.

TABLE 3

| Citrate Infusion Titration Guidelines | |
|---|---|
| Circuit Ionized $Ca^{2+}$ (between the SCD and patient) | Infusion Adjustment with ACD-A citrate solution (as described above) |
| If circuit ionized $Ca^{2+}$ is less than 0.20 mmol/L | then decrease the rate of citrate infusion by 5 mL/hour |
| If circuit ionized $Ca^{2+}$ is 0.20-0.40 mmol/L (Optimal Range) | then make no change to the rate of citrate infusion |
| If circuit ionized $Ca^{2+}$ is 0.41-0.50 mmol/L | then increase the rate of citrate infusion by 5 mL/hour |
| If circuit ionized $Ca^{2+}$ is greater than 0.50 mmol/L | then increase the rate of citrate infusion by 10 mL/hour |

TABLE 4

Calcium Infusion Titration Guidelines

| Patient Ionized $Ca^{2+}$ (drawn systemically from patient) | $Ca^{2+}$ Infusion (20 mg/mL $CaCl_2$) Adjustment |
|---|---|
| If patient ionized $Ca^{2+}$ is greater than 1.45 mmol/L | then decrease the rate of $CaCl_2$ infusion by 10 mL/hour |
| If patient ionized $Ca^{2+}$ is 1.45 mmol/L (maximum allowable amount) | then decrease the rate of $CaCl_2$ infusion by 5 mL/hour |
| If patient ionized $Ca^{2+}$ is 0.9 mmol/L (minimum allowable amount) | then increase the rate of $CaCl_2$ infusion by 5 mL/hour |
| If patient ionized $Ca^{2+}$ is less than 0.9 mmol/L | then administer a 10 mg/kg $CaCl_2$ bolus and increase the rate of $CaCl_2$ infusion by 10 mL/hour |
| Default Range (preferred target level) | 1.0-1.2 mmol/L |

It should be understood that the deactivation techniques described herein also can apply to platelets. In certain embodiments, agents used to deactivate a platelet and/or inhibit release of a pro-inflammatory substance from a platelet include, but are not limited to, agents that inhibit thrombin, antithrombin III, meglatran, herudin, Protein C and Tissue Factor Pathway Inhibitor. In addition, some leukocyte inhibiting agents can act as platelet inhibiting agents. For example, calcium chelating agents, such as citrate, sodium hexametaphosphate, ethylene diamine tetraacetic acid (EDTA), triethylene tetramine, diethylene triamine, o-phenanthroline, and oxalic acid can deactivate a platelet and/or inhibit release of a pro-inflammatory substance from a platelet.

In light of the foregoing description, the specific non-limiting examples presented below are for illustrative purposes and not intended to limit the scope of the invention in any way.

EXAMPLES

Example 1. Treatment of Inflammation Associated with Acute Sepsis in an Animal Model Activated leukocytes, especially neutrophils, are major contributors to the pathogenesis and progression of sepsis as well as other clinical inflammatory disorders. This example describes in vivo experiments that evaluate the effect of different SCD cartridges on leukocyte sequestration and deactivation. The results demonstrate that the choice of a particular SCD cartridge can have a profound effect on the pathogenesis and progression of sepsis in a large animal model. In particular, the results demonstrate that a SCD cartridge having a larger sequestration area is more effective than a SCD cartridge having a smaller sequestration area in alleviating complications associated with sepsis and in prolonging survival.

(I) Methods and Materials
A—Animal Model

The efficacy of the SCD cartridge in treating inflammation was evaluated in a well-established porcine model of acute septic shock. (See, e.g., Humes et al. (2003) CRIT. CARE MED. 31:2421-2428.)

Pigs weighing 30-35 kg were utilized. After administration of anesthesia and intubation, the pigs underwent placement of an arterial catheter and a Swan-Ganz thermodilution catheter (which were connected to transducers) to monitor arterial blood pressure, cardiac output, and central venous pressures. An ultrasonic flow probe was placed on a renal artery for continuous assessment of renal blood flow (RBF).

To induce septic shock, the pigs received $30 \times 10^{10}$ bacteria/kg body weight of E. coli into their peritoneal cavities. To better replicate the human clinical situation, the antibiotic Cefriaxione (100 mg/kg) was administered 15 minutes after bacteria infusion. During the first hour following bacteria infusion, all animals were resuscitated with 80 mL/kg of crystalloid and 80 mL/kg of colloid. All treatment groups received identical volume resuscitation protocols. No animal received vasopressor or inotropic agents.

B—Extracorporeal Circuit Containing the SCD Cartridge

Figure 4:
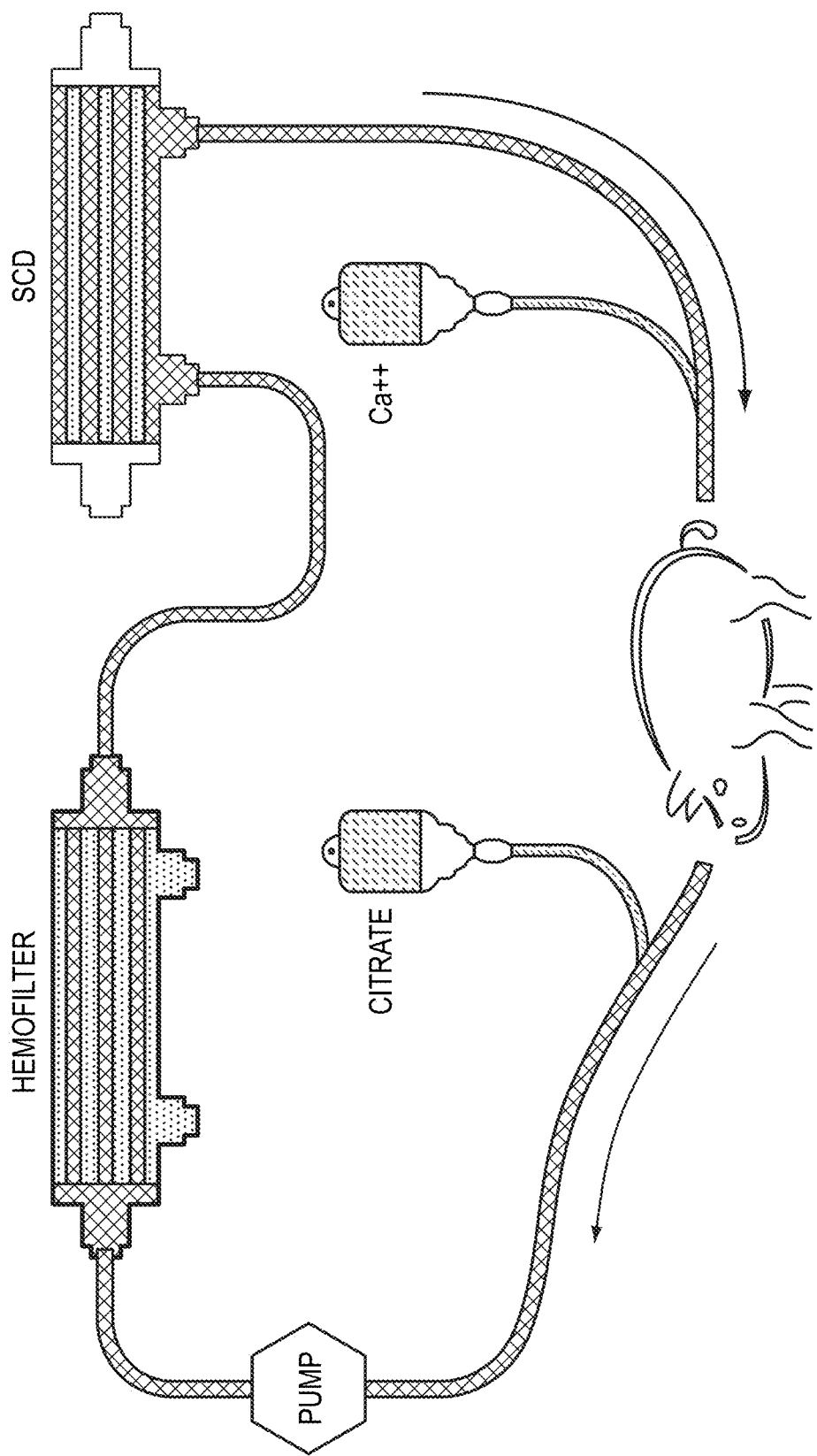
FIG. 4 is a schematic representation of an embodiment of a system configuration used in treating a subject with sepsis. The container to the left of the animal, below the hemofilter contains citrate. The container to the right of the animal, below the SCD cartridge contains calcium ions.

Immediately after bacterial administration, the animals were connected to an extracorporeal circuit containing a standard continuous renal replacement therapy (CRRT) hemofilter and a SCD device, as depicted in FIG. 4. The hemofilter was a Fresenius F-40 hemofiltration cartridge (Fresenius AG). The SCD cartridge (CytoPherx, Inc.) was connected to the blood port of the hemofilter through its side port using a special blood line connector. Two types of SCD cartridges were tested. The first type of SCD cartridge (based on a Fresenius F-40 hemofiltration cartridge) had a membrane surface area of 1.0 $m^2$ facing the extracapillary space, which had an ECS fill volume of 130 mL. The second type of SCD cartridge (based on a Fresenius F-80A hemofiltration cartridge) had a membrane surface area of 2.5 $m^2$ facing the extracapillary space, which had an ECS fill volume of 250 mL. The F-40 and F-80A SCD cartridges each contained polysulfone hollow fibers with an inner diameter of 200 µm and a wall thickness of 40 µm. The pressure drop across the SCD was 70-75 mmHg. Either the Gambro AK-10 or the Fresenius 2008H dialysis pump system was utilized for these experiments. Extracorporeal blood flow was regulated at 100-150 mL/min.

A balanced electrolyte replacement solution (Na 150 mEq/L, Cl 115 mEq/L, $HCO_3$ 38 mEq/L, Ca 2.5 mEq/L, and Mg 1.6 mEq/L in Dextrose 5%) was infused into the blood line on a 1:1 volume replacement basis for the net ultrafiltrate which would exit the circuit. In addition, continuous volume resuscitation with normal saline at 150 mL/h was employed to maintain mean arterial pressure and cardiac output in the treated animals.

As a control, one group animals (n=3) underwent extracorporeal blood perfusion in a circuit containing the hemofilter alone but without the SCD device. These animals also received regional citrate infusion and were referred to as the conventional citrate (Con-citrate) group. A second group of animals was treated similarly to the SCD group with citrate but without bacterial infusion. These animals were referred to as the non-septic control (NS-control) group.

C—Anticoagulation Process

The anticoagulation process was a critical variable in this series of experiments. One group of animals referred to as the SCD-heparin group (SCD-H, n=12), received systemic heparinization to maintain patency of the extracorporeal circuit with targeted activated clotting times (ACTs) of 200-300 sec and treated with a SCD cartridge based on the Fresenius F-40 cartridge with a membrane surface area of 1.0 $m^2$ facing the extracapillary space. A second group of animals referred to as the SCD-citrate, F-40 group (SCD-C, F-40; n=13) were treated with SCD cartridges based on the Fresenius F-40, cartridge with a membrane surface area of 1.0 $m^2$ facing the extracapillary space received regional citrate anticoagulation (Pinnick, R. V. et al., (1983) N. ENGL. J. MED., 308(5): 258-261; Lohr, J. W. et al., (1989) AM. J. KIDNEY DIS., 13(2):104-107; Tobe, S. W. et al. (2003) J. CRIT. CARE, 18(2): 121-129). In addition, a third group of animals also received regional citrate anticoagulation and were treated with SCD cartridges based on the Fresenius F-80A, with a membrane surface area of 2.5 m² facing the extracapillary space (SCD-C, 2.5; n=3). Regional citrate coagulation was achieved by infusing citrate dextrose-A (ACD-A, Baxter) pre-hemofilter at a rate of 2.5-5.0 mM citrate per 1000 mL whole blood. This essentially lowered iCa concentration in the circuit to 0.2-0.5 mmol/L. Calcium chloride was infused into the venous return of the circuit to maintain systemic iCa values of 1.1-1.3 mmol/L. iCa levels were monitored using an iSTAT reader (Abbott Labs).

D—Complete Blood Counts, Serum Chemistries, and Systemic Inflammation Parameters Complete blood counts and serum chemistries were measured with a Hemavet automated analyzer (Drew Scientific) and a VET Test automated analyzer (IDEXX), respectively. Serum myeloperoxidase (MPO) activity was measured using a modified o-dianisidine assay containing 4-aminobenzoic acid hydrazide as a potent and specific inhibitor of MPO (Fietz S, et al., (2008) RES. VET. SCI., 84(3):347-353). Cytokine concentrations, including IL-1β, IL-6, IL-8, IL-10, TNF-α and IFN-γ, were measured with commercially available enzyme-linked immunosorbent assay (ELISA) kits from R&D Systems.

E—Assessment of Leukocyte Activation

FITC-conjugated anti-porcine CD11b antibody (SeroTec) was added to pre-chilled peripheral blood. Red blood cells were lysed and the remaining leukocytes were fixed by addition of a FACS lysing solution (Becton-Dickinson). Cells were collected by centrifugation and resuspended for flow-cytometric analysis. CD11b expression was quantitatively assessed as mean fluorescent intensity (MFI) with an Accuri flow cytometer.

Peripheral blood mononuclear cells (PBMCs) were isolated from the venous blood. Mononuclear cells were isolated using standard Ficoll-Hypaque gradient technique (Humes et al. (2003) CRIT. CARE MED. 31:2421-2428). These cells were then incubated for 24 hours in culture plates containing RPMI-1640 medium supplemented with antibiotics in the absence or the presence of 1 μg/mL of lipopolysaccharide (LPS). The supernatants were collected and cytokine concentrations measured. The ratio of stimulated to unstimulated cytokine concentrations in the supernatants was then calculated.

F—Lung Histology and Immunohistochemistry

Lung samples were harvested post-mortem from septic pigs treated under SCD-citrate or SCD-heparin conditions. Two random sections from each of the 5 lobes of the lungs were processed for cryosections. Frozen lung samples were cut at 5-μm thickness and fixed with 4% paraformaldehyde on ice for 10 minutes. Tissues were stained with hematoxylin and eosin for light microscopic examination, or for CD11b evaluation; nonspecific adsorption was minimized by incubating the section in goat serum in PBS for 1 hour.

For evaluation of CD11b expression, lung sections were incubated with primary anti-CD11b antibody at recommended dilutions for 1 hour at room temperature. This was followed by incubation with an anti-mouse IgG Alexafluor594 conjugate (1:200 dilution) at room temperature for 30 minutes, and counterstaining the nuclei with DAPI. ImageJ software (Abramoff, M. D. (2004) Biophotonics International, 11(7): 36-42) was used to quantify the percentage of CD11b-positive areas in random 10× images taken with fixed capture settings. Cell number normalization was achieved by determining the percentage of DAPI-positive areas in the same picture. The results were expressed as the ratio of percent CD11b-positive area by percent DAPI-positive area.

G—Cell Elution from SCD Cartridges

Prior to disconnecting the circuit, blood was returned to the pig by perfusion with replacement fluid. The SCD extracapillary space (ECS) was then continuously flushed with replacement fluid until the perfusate fluid was free of visible blood. After draining off the replacement fluid, the cartridge was either fixed for histologic processing (Humes, H. D. et al., (2010) BLOOD PURIFICATION, 29:183-190) or exchanged with a stabilization buffer containing a calcium chelating agent. Adherent cells were mechanically removed from the SCD eluent for analysis. To ensure that all cells adherent to the device were eluted, several cartridges were digested after elution with a DNA isolation buffer (SDS and proteinase K). The DNA extracted in this manner, on average, was less than 5 percent of the eluted DNA from the cartridge.

H—Statistical Analysis

Group comparisons at multiple time points utilized ANOVA with repeated measures. Otherwise, comparisons between groups used Students' T test, paired or unpaired, as appropriate. Statistical significance was defined as $p<0.05$.

(II) Results and Discussion

A—Observations of Cardiovascular Parameters

The porcine model of septic shock was utilized to evaluate the effectiveness of SCD cartridges having different membrane surface areas combined with either systemic heparin or regional citrate anticoagulation. Specifically, one group of animals (SCD-H) was treated with systemic heparin anticoagulation and either an F-40-based SCD or an F-80A-based SCD cartridge. A second group of animals was treated with regional citrate anticoagulation and an F-40-based SCD cartridge (SCD-C, F-40). A third group of animals was treated with regional citrate anticoagulation and an F-80A-based SCD cartridge (SCD-C, F-80A). A fourth group of animals received citrate without a SCD device (con-citrate).

Figure 5B:
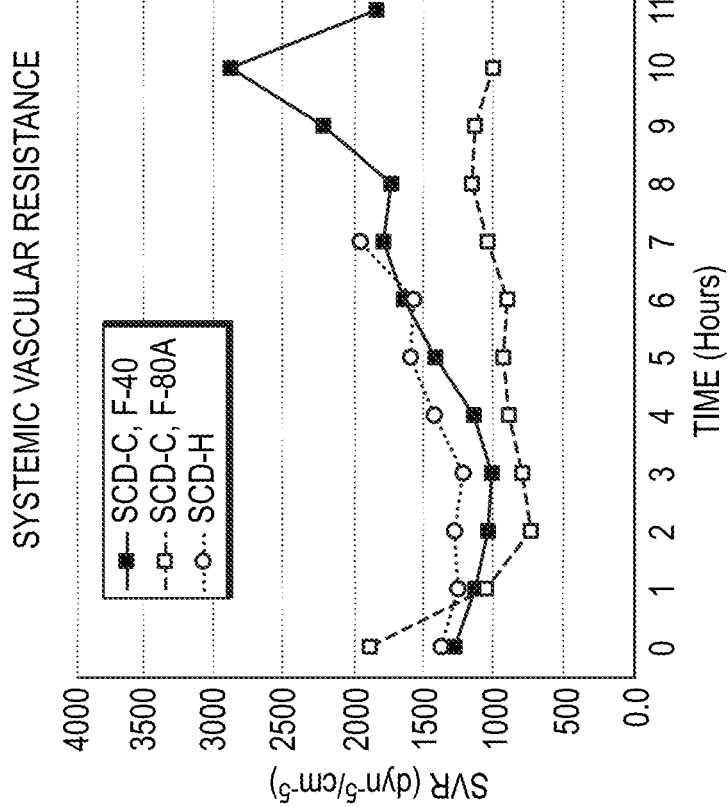
FIGS. 5A-F are graphical depictions of changes in cardiovascular parameters of subjects with sepsis treated with an F-40 SCD device in the presence of heparin (SCD-H); an F-40 SCD device in the presence of citrate (SCD-C, F-40); or an F-80A SCD device in the presence of citrate (SCD-C, F-80A). Results are shown for mean arterial blood pressure (FIG. 5A); systemic vascular resistance (FIG. 5B); renal vascular resistance (FIG. 5C); cardiac output (FIG. 5D); pulmonary vascular resistance (FIG. 5E); and hematocrit (FIG. 5F).
Figure 5A:
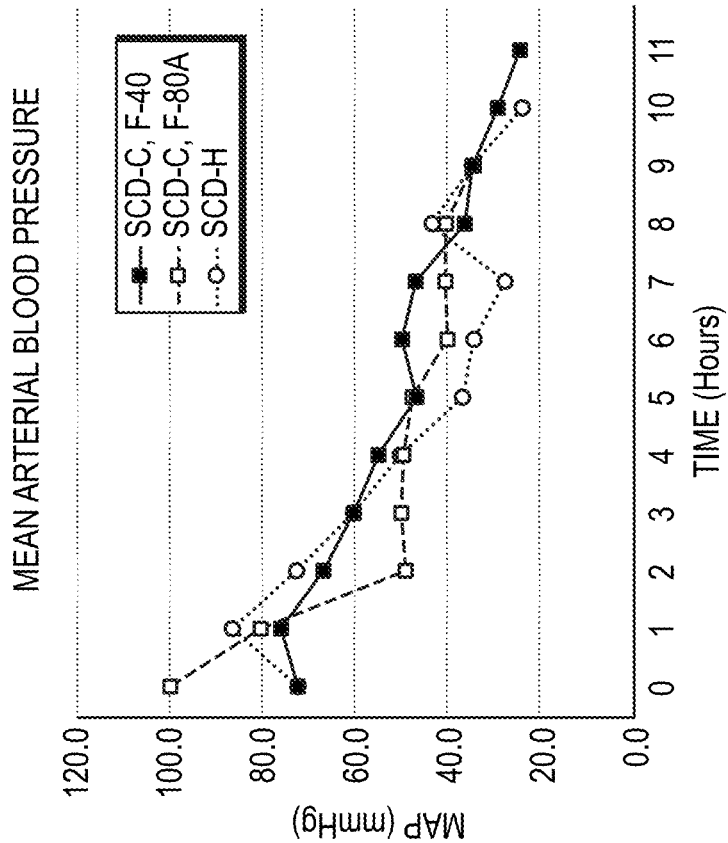

As indicated in Table 5 and FIG. 5A, the intraperitoneal administration of bacteria induced a rapid and profound decline in mean arterial pressure (MAP) in all four groups of animals. This decline was progressive and ultimately fatal.

TABLE 5

| | Cardiovascular Parameters | | | | | | |
|---|---|---|---|---|---|---|---|
| Parameter | 0 | 1 | 2 | 3 | 4 | 5 | 6 |
| Cardiac output, L/min | | | | | | | |
| SCD-Citrate F-40 | 4.3 ± 0.3 | 4.9 ± 0.2 | 4.7 ± 0.2 | 4.4 ± 0.3 | 3.7 ± 0.2 | 2.7 ± 0.3 | 2.3 ± 0.2 |
| SCD-Citrate F-80A | 3.9 ± 0.8 | 5.2 ± 0.6 | 4.8 ± 0.3 | 4.5 ± 0.4 | 4.1 ± 0.5 | 3.7 ± 0.5 | 3.1 ± 0.2 |

TABLE 5-continued

Cardiovascular Parameters

| | | | | | | | |
|---|---|---|---|---|---|---|---|
| SCD-Heparin | 4.1 ± 0.3 | 5.2 ± 0.2 | 4.2 ± 0.3 | 3.8 ± 0.2 | 2.6 ± 0.2 | 1.7 ± 0.2 | 1.5 ± 0.2 |
| Con-Citrate | 4.5 ± 0.3 | 4.7 ± 0.5 | 5.2 ± 1.2 | 3.6 ± 0.5 | 3.8 ± 0.5 | 2.6 ± 0.4 | 1.5 ± 0.3 |
| Systolic blood pressure, mmHg | | | | | | | |
| SCD-Citrate F-40 | 96.9 ± 5.7 | 99.9 ± 2.2 | 94.5 ± 3.2 | 88.9 ± 4.4 | 80.3 ± 4.1 | 69.7 ± 6.5 | 69.5 ± 7.0 |
| SCD-Citrate F-80A | 118.7 ± 29.2 | 98.7 ± 9.7 | 65.7 ± 4.4 | 70.3 ± 4.1 | 69.0 ± 5.1 | 67.0 ± 4.6 | 59.3 ± 4.5 |
| SCD-Heparin | 96.6 ± 4.7 | 104.9 ± 4.8 | 94.4 ± 6.5 | 88.0 ± 4.4 | 76.4 ± 6.3 | 58.4 ± 4.4 | 52.4 ± 8.4 |
| Con-Citrate | 87.3 ± 1.8 | 103.0 ± 11.4 | 77.3 ± 4.2 | 69.0 ± 3.2 | 74.7 ± 13.7 | 51.7 ± 4.9 | 30.0 ± 20.0 |
| Diastolic blood pressure, mmHg | | | | | | | |
| SCD-Citrate F-40 | 60.5 ± 4.6 | 64.5 ± 2.9 | 54.0 ± 4.7 | 45.5 ± 4.4 | 42.1 ± 4.7 | 39.7 ± 4.8 | 39.9 ± 4.8 |
| SCD-Citrate F-80A | 89.3 ± 25.9 | 70.0 ± 6.1 | 40.3 ± 6.6 | 40.0 ± 1.0 | 39.3 ± 1.2 | 36.7 ± 1.2 | 29.0 ± 0.6 |
| SCD-Heparin | 61.4 ± 3.3 | 75.6 ± 4.5 | 61.7 ± 6.6 | 48.3 ± 3.4 | 38.6 ± 3.6 | 27.6 ± 3.4 | 26.1 ± 5.1 |
| Con-Citrate | 53.3 ± 2.0 | 71.7 ± 6.3 | 50.3 ± 4.5 | 42.7 ± 1.5 | 48.3 ± 12.9 | 31.0 ± 2.1 | 20.0 ± 10.0 |
| Mean arterial pressure, mmHg | | | | | | | |
| SCD-Citrate F-40 | 72.2 ± 4.8 | 75.8 ± 2.6 | 67.2 ± 4.1 | 59.9 ± 4.2 | 54.8 ± 3.9 | 47.1 ± 6.4 | 49.5 ± 4.5 |
| SCD-Citrate F-80A | 99.1 ± 27 | 79.6 ± 7.3 | 48.8 ± 5.8 | 50.1 ± 1.5 | 49.2 ± 2.5 | 46.8 ± 2.1 | 39.1 ± 1.6 |
| SCD-Heparin | 72.0 ± 3.3 | 86.1 ± 4.4 | 72.6 ± 6.5 | 60.6 ± 3.1 | 50.3 ± 4.4 | 36.5 ± 3.6 | 34.3 ± 6.3 |
| Con-Citrate | 64.7 ± 1.7 | 82.1 ± 8.0 | 59.3 ± 4.1 | 51.4 ± 1.1 | 44.5 ± 0.5 | 37.9 ± 2.9 | 23.3 ± 13.3 |
| Systemic vascular resistance, dyn · s/cm$^5$ | | | | | | | |
| SCD-Citrate F-40 | 1288 ± 119 | 1119 ± 61 | 1027 ± 73 | 994 ± 72 | 1101 ± 64 | 1414 ± 111 | 1601 ± 143 |
| SCD-Citrate F-80A | 1881 ± 152 | 1073 ± 23 | 710 ± 143 | 784 ± 59 | 874 ± 114 | 926 ± 131 | 884 ± 59 |
| SCD-Heparin | 1371 ± 137 | 1250 ± 120 | 1268 ± 110 | 1200 ± 58 | 1412 ± 75 | 1567 ± 140 | 1552 ± 242 |
| Con-Citrate | 1034 ± 111 | 1149 ± 94 | 1067 ± 72 | 976 ± 96 | 1174 ± 103 | 1375 ± 343 | 1274 |
| Pulmonary vascular resistance, dyn · s/cm$^5$ | | | | | | | |
| SCD-Citrate F-40 | 141 ± 17 | 180 ± 25 | 255 ± 33 | 321 ± 47 | 393 ± 78 | 573 ± 118 | 632 ± 97 |
| SCD-Citrate F-80A | 164 ± 13 | 228 ± 83 | 207 ± 86 | 281 ± 63 | 317 ± 55 | 377 ± 55 | 475 ± 61 |
| SCD-Heparin | 268 ± 102 | 287 ± 51 | 384 ± 46 | 525 ± 58 | 763 ± 76 | 1293 ± 243 | 1024 ± 198 |
| Con-Citrate | 147 ± 18 | 122 ± 17 | 404 ± 177 | 602 ± 83 | 525 ± 151 | 982 ± 248 | 1199 ± 14 |
| Pulmonary capillary wedge pressure, mmHg | | | | | | | |
| SCD-Citrate F-40 | 7.8 ± 0.7 | 8.5 ± 0.9 | 8.3 ± 1.0 | 7.0 ± 1.1 | 7.2 ± 1.1 | 7.2 ± 1.1 | 5.9 ± 0.9 |
| SCD-Citrate F-80A | 8.3 ± 0.9 | 11.3 ± 2.4 | 10.7 ± 3.7 | 7.3 ± 1.2 | 6.3 ± 0.9 | 5.7 ± 0.9 | 6.0 ± 0.6 |
| SCD-Heparin | 7.0 ± 0.8 | 8.5 ± 1.2 | 7.2 ± 0.8 | 6.6 ± 0.7 | 7.3 ± 1.4 | 6.3 ± 1.0 | 5.7 ± 1.0 |
| Con-Citrate | 7.7 ± 1.2 | 10.7 ± 0.9 | 9.0 ± 1.5 | 7.3 ± 1.3 | 6.3 ± 0.3 | 6.3 ± 0.3 | 8.5 ± 1.5 |
| Renal arterial blood flow, mL/min | | | | | | | |
| SCD-Citrate F-40 | 197.4 ± 16.9 | 183.7 ± 12.8 | 193.4 ± 25.5 | 173.2 ± 23.4 | 125.1 ± 18.2 | 79.9 ± 18.0 | 69.3 ± 17.9 |
| SCD-Citrate F-80A | 152.0 ± 15.5 | 141.0 ± 2.3 | 170.7 ± 31.5 | 173.3 ± 33.5 | 153.0 ± 23.9 | 131.3 ± 26.9 | 103.0 ± 23.5 |
| SCD-Heparin | 207.0 ± 22.8 | 155.2 ± 15.7 | 152.0 ± 21.7 | 148.5 ± 18.8 | 111.8 ± 21.4 | 53.4 ± 13.6 | 37.6 ± 13.8 |
| Con-Citrate | 200.3 ± 19.5 | 157.3 ± 38.1 | 184.3 ± 63.0 | 183.0 ± 48.3 | 138.0 ± 17.7 | 69.0 ± 24.0 | 19.0 ± 19.0 |
| Renal vascular resistance, mmHg/min/mL | | | | | | | |
| SCD-Citrate F-40 | 0.39 ± 0.03 | .037 ± .0.6 | 0.37 ± 0.05 | 0.48 ± 0.07 | 1.05 ± 0.29 | 1.37 ± 0.44 | 2.18 ± 0.63 |
| SCD-Citrate F-80A | 0.67 ± 0.27 | 0.49 ± 0.06 | 0.25 ± 0.05 | 0.28 ± 0.07 | 0.30 ± 0.05 | 0.35 ± 0.08 | 0.44 ± 0.09 |
| SCD-Heparin | 0.39 ± 0.08 | 0.58 ± 0.08 | 0.55 ± 0.11 | 0.41 ± 0.04 | 0.63 ± 0.20 | 0.77 ± 0.16 | 1.30 ± 0.37 |
| Con-Citrate | 0.30 ± 0.02 | 0.52 ± 0.12 | 0.33 ± 0.08 | 0.26 ± 0.05 | 0.28 ± 0.04 | 0.67 ± 0.31 | 0.75 |

| Parameter | 7 | 8 | 9 | 10 | 11 |
|---|---|---|---|---|---|
| Cardiac output, L/min | | | | | |
| SCD-Citrate F-40 | 2.1 ± 0.3 | 1.7 ± 0.1 | 1.0 ± 0.3 | 1.1 ± 0.1 | 1.1 ± 0.1 |
| SCD-Citrate F-80A | 2.8 ± 0.2 | 2.4 ± 0.3 | 2.1 ± 0.4 | 1.4 ± 0.2 | |
| SCD-Heparin | 1.3 ± 0.2 | 1.1 | | | |
| Con-Citrate | 1 | | | | |
| Systolic blood pressure, mmHg | | | | | |
| SCD-Citrate F-40 | 68.0 ± 6.5 | 55.0 ± 8.7 | 45.8 ± 5.1 | 53.5 ± 0.5 | 36.5 ± 8.5 |
| SCD-Citrate F-80A | 60.7 ± 8.7 | 61.7 ± 8.1 | 51.0 ± 4.5 | 33.3 ± 7.9 | |
| SCD-Heparin | 41.0 ± 12.1 | 55 | | | |

TABLE 5-continued

Cardiovascular Parameters

Con-Citrate
Diastolic blood
pressure, mmHg

| | | | | | |
|---|---|---|---|---|---|
| SCD-Citrate F-40 | 36.1 ± 3.4 | 26.3 ± 3.2 | 26.5 ± 4.7 | 32.5 ± 4.5 | 19.5 ± 2.5 |
| SCD-Citrate F-80A | 30.3 ± 1.8 | 27.3 ± 1.9 | 25.0 ± 2.9 | 17.0 ± 3.5 | |
| SCD-Heparin | 24.0 ± 7.3 | 36.5 | | | |
| Con-Citrate | | | | | |

Mean arterial
pressure, mmHg

| | | | | | |
|---|---|---|---|---|---|
| SCD-Citrate F-40 | 46.5 ± 3.7 | 35.7 ± 4.9 | 34.3 ± 5.3 | 28.4 ± 10.1 | 23.3 ± 2.7 |
| SCD-Citrate F-80A | 40.4 ± 3.9 | 38.8 ± 3.9 | 33.7 ± 3.3 | 22.4 ± 4.9 | |
| SCD-Heparin | 26.8 ± 8.6 | 42.7 ± 0.3 | | | |
| Con-Citrate | | | | | |

Systemic vascular
resistance, dyn · s/cm$^5$

| | | | | | |
|---|---|---|---|---|---|
| SCD-Citrate F-40 | 1767 ± 204 | 1701 ± 179 | 2170 ± 183 | 2856 ± 722 | 1776 ± 336 |
| SCD-Citrate F-80A | 1028 ± 139 | 1134 ± 186 | 1088 ± 87 | 971 | |
| SCD-Heparin | 1918 ± 533 | | | | |
| Con-Citrate | | | | | |

Pulmonary vascular
resistance, dyn · s/cm$^5$

| | | | | | |
|---|---|---|---|---|---|
| SCD-Citrate F-40 | 859 ± 145 | 935 ± 131 | 948 ± 343 | 1602 ± 242 | 1067 ± 133 |
| SCD-Citrate F-80A | 543 ± 54 | 634 ± 49 | 694 ± 58 | 552 | |
| SCD-Heparin | 1121 ± 291 | 1504 | | | |
| Con-Citrate | | | | | |

Pulmonary capillary
wedge pressure,
mmHg

| | | | | | |
|---|---|---|---|---|---|
| SCD-Citrate F-40 | 5.9 ± 0.8 | 4.9 ± 1.0 | 6.8 ± 2.1 | 5.0 ± 2.6 | 3.5 |
| SCD-Citrate F-80A | 6.3 ± 0.7 | 6.3 ± 0.7 | 6.0 ± 0.6 | 12.0 ± 5.5 | |
| SCD-Heparin | 6.8 ± 1.0 | 5.5 | | | |
| Con-Citrate | | | | | |

Renal arterial blood
flow, mL/min

| | | | | | |
|---|---|---|---|---|---|
| SCD-Citrate F-40 | 48.5 ± 14.7 | 37.1 ± 11.8 | 37.0 ± 13.9 | 47.5 ± 12.5 | 13.5 ± 8.5 |
| SCD-Citrate F-80A | 83.0 ± 13.1 | 67.3 ± 8.2 | 49.7 ± 9.2 | 30.5 ± 24.5 | |
| SCD-Heparin | 45.8 ± 20.1 | 24 | | | |
| Con-Citrate | | | | | |

Renal vascular
resistance,
mmHg/min/mL

| | | | | | |
|---|---|---|---|---|---|
| SCD-Citrate F-40 | 1.93 ± 0.72 | 1.05 ± 0.31 | 0.82 ± 0.37 | 2.38 ± 1.56 | |
| SCD-Citrate F-80A | 0.50 ± 0.08 | 0.59 ± 0.07 | 1.69 ± 1.14 | | |
| SCD-Heparin | 0.78 ± 0.23 | 1.64 ± 0.30 | | | |
| Con-Citrate | | | | | |

Figure 5D:
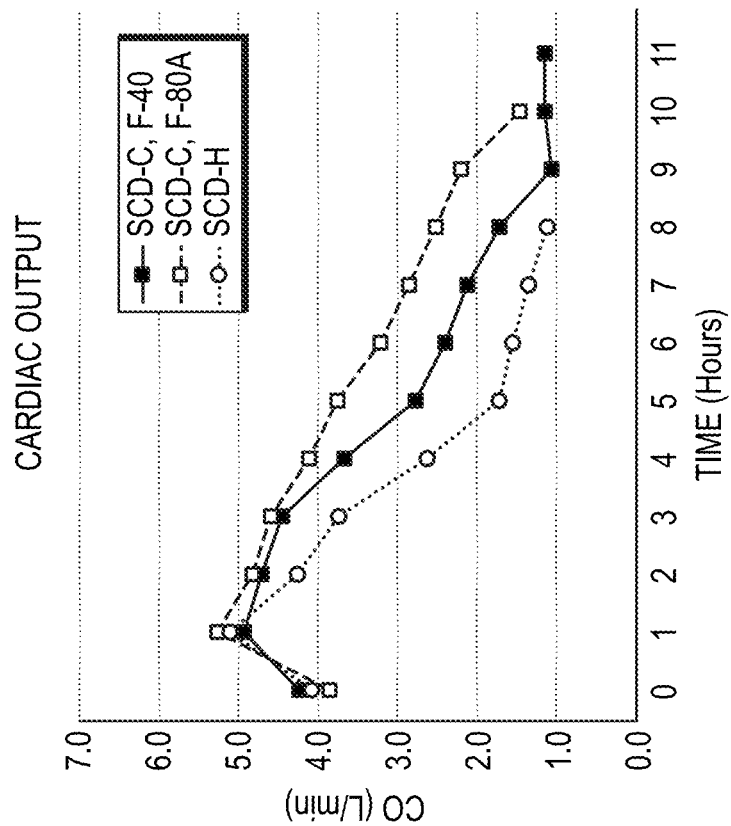
Figure 5C:
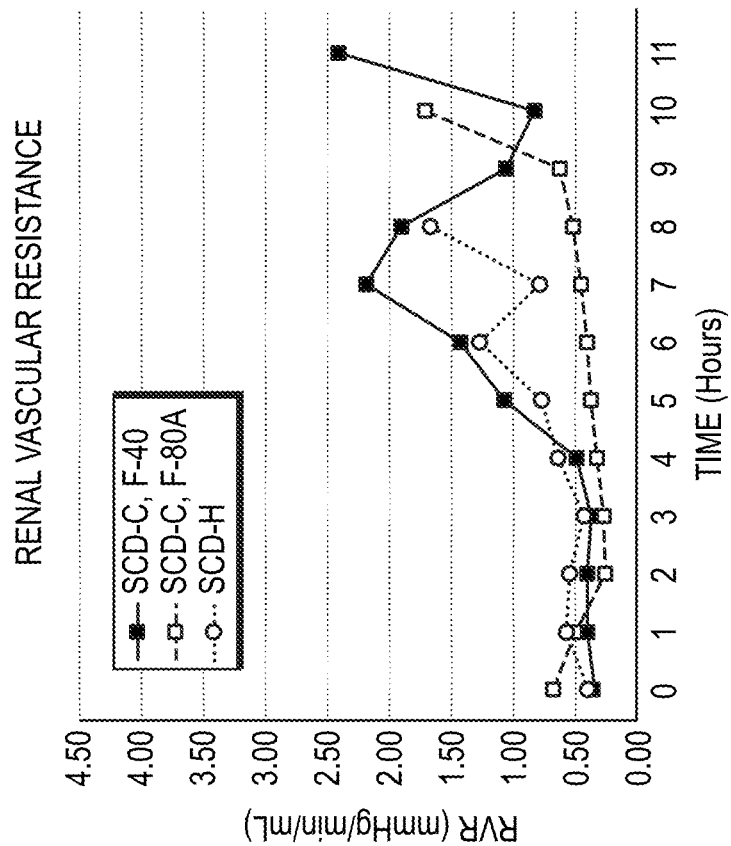

Cardiac outputs (CO) were also assessed. As depicted in FIG. 5B, CO was significantly higher (p<0.02) in the SCD-C groups. This increase in CO was not due to differences in left ventricular filling pressures, since pulmonary capillary wedge pressures were similar in all three groups. Rather, the increase in CO in the SCD-C groups was associated with lower levels of systemic vascular resistance (SVR; p<0.03; FIG. 5C) and pulmonary vascular resistance (PVR; p<0.001; FIG. 5D). Notably, the SCD-C, F-80A group consistently showed the most improvement in cardiac out and also had lower SVR, PVR, and renal vascular resistance (FIG. 5E) when compared to the other groups.

Figure 5F:
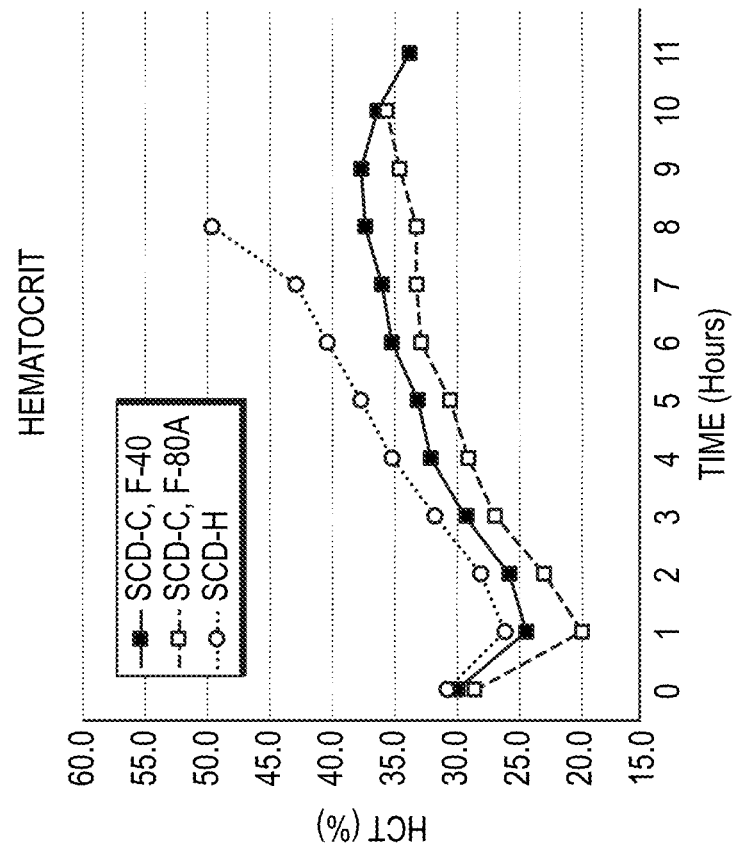
Figure 5E:
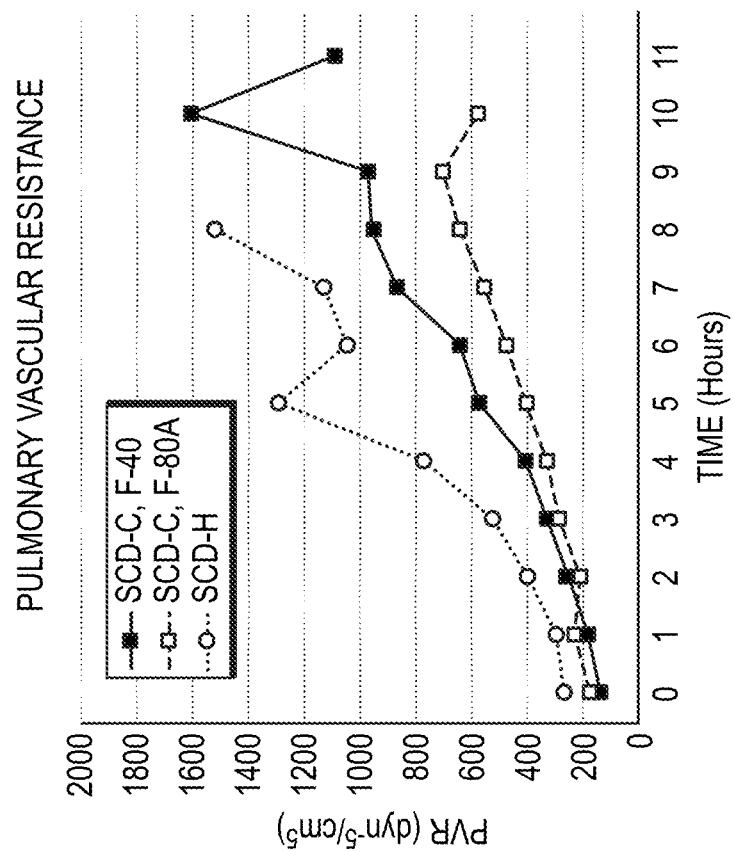

As a quantitative measure of the systemic capillary leak induced by bacterial sepsis, changes in hematocrit (HCT) were assessed. As depicted in FIG. 5F, the SCD-H group had a higher rate of HCT increase, reflective of larger rates of volume loss from the intravascular compartment. In comparison, HCT levels plateaued after 6 hours in the SCD-C groups. Notably, the SCD-C, F-80A group showed the most protection to the bacterially activated systemic capillary leak.

Figure 6D:
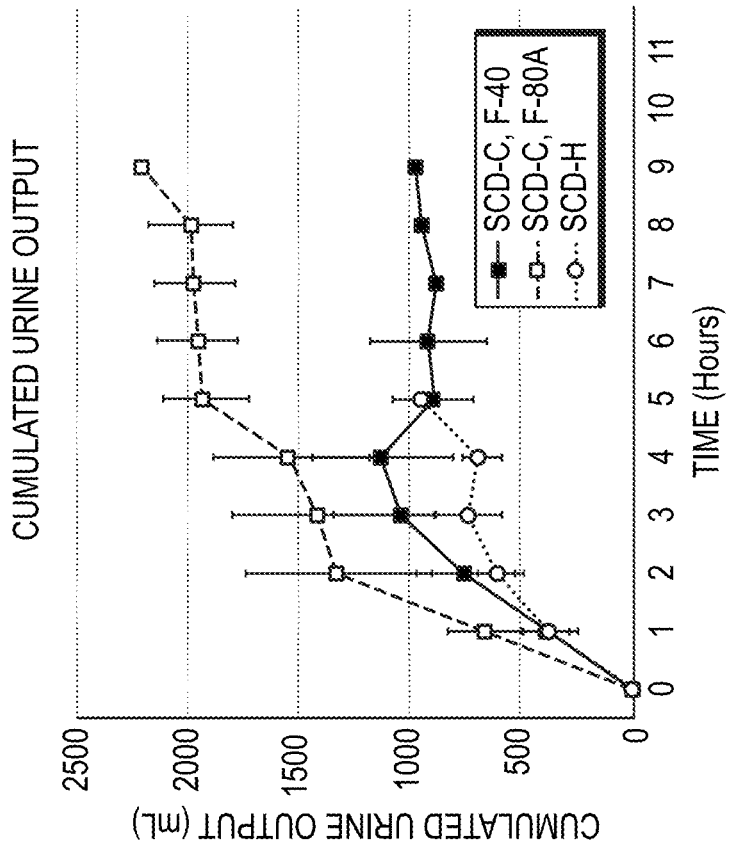
Figure 6C:
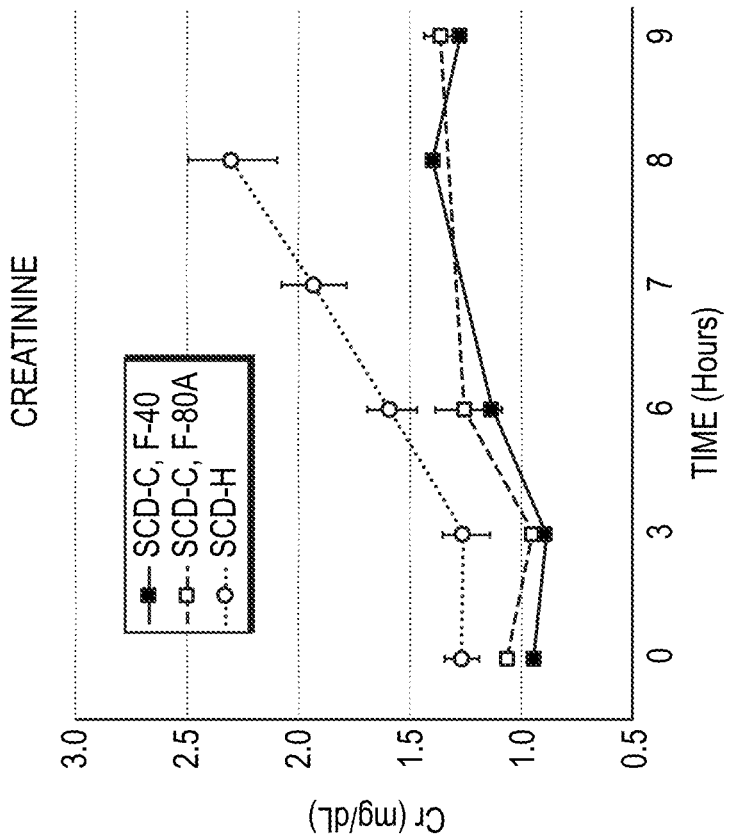

Renal parameters were also assessed. As shown in FIG. 6, the SCD-C groups exhibited much better renal function than the SCD-H group as reflected in the lower BUN (p<0.02) and serum creatinine levels (p=0.007). Renal blood flow (RBF) was also much better preserved in the SCD-C, F-80A group as compared to the SCD-H group (p<0.05). Furthermore, the SCD-C, F-80A group also exhibited must higher urine output (p<0.05).

Figure 7:
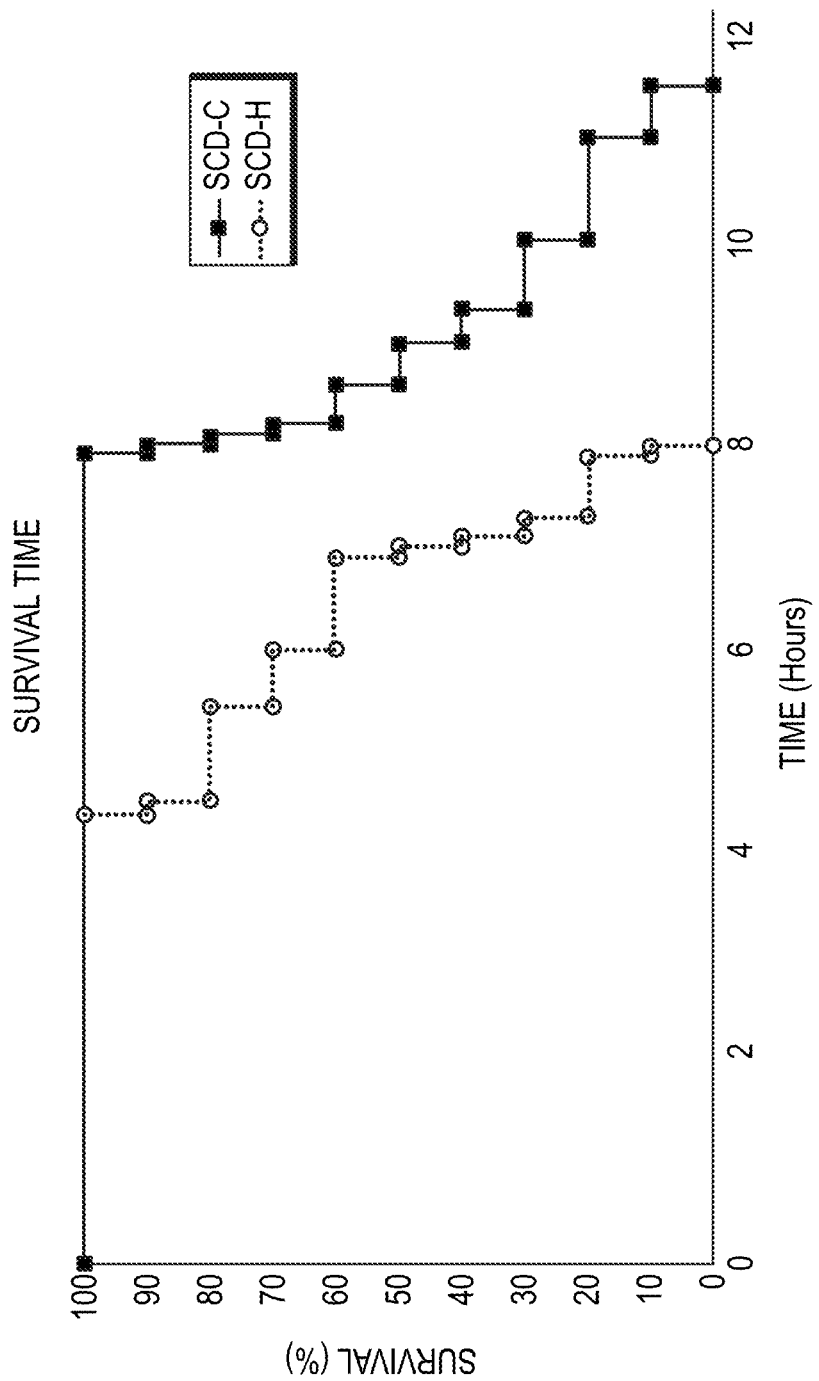
FIG. 7 is a graphical depiction of survival times for subjects with sepsis treated with an F-40 SCD device in the presence of heparin (SCD-H) or with an F-40 or F-80A SCD device in the presence of citrate (SCD-C).
Figure 8:
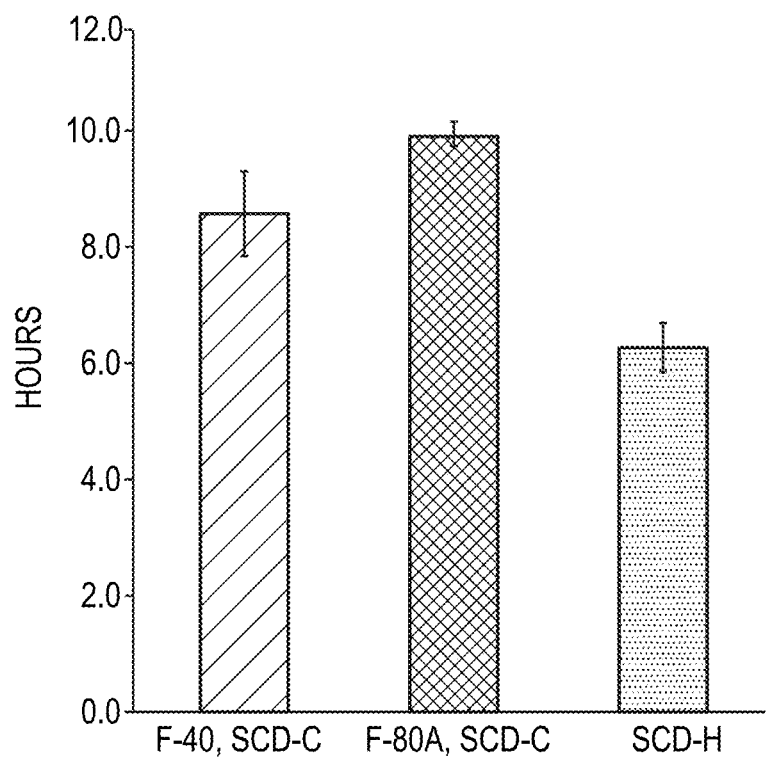
FIG. 8 is a bar graph depicting survival times for subjects with sepsis treated an F-40 SCD device in the presence of heparin (SCD-H); an F-40 SCD device in the presence of citrate (F-40, SCD-C); or an F-80A SCD device in the presence of citrate (F-80A, SCD-C).

The improved cardiovascular and renal parameters observed with the SCD-C groups translated to longer survival time. As shown in FIG. 7, the citrate-treated animals survived 8.8±0.4 hours compared to 6.4±0.3 hours for the SCD-H animals (p=0.0002). Notably, the SCD-C, F-80A group had the longest survival times (11.5, 10, and 9.5 hours), as shown in FIG. 8.

Only those animals treated with a combination of the SCD device and citrate exhibited improved cardiovascular parameters and organ function. The Con-citrate group of animals treated with a single hemofilter cartridge with citrate anticoagulation but without the SCD device demonstrated similar cardiovascular parameters as the SCD-H group, with a average survival time of 6.5±0.5 hours. Thus, both the SCD cartridge and the citrate anticoagulation protocol were required to provide a survival advantage. Furthermore, it was found that the surface area for sequestration can have a profound effect on alleviating complications relating to sepsis and in prolonging survival time post infection.

B—Observations of Leukocyte Sequestration and Activation

Figure 10A:
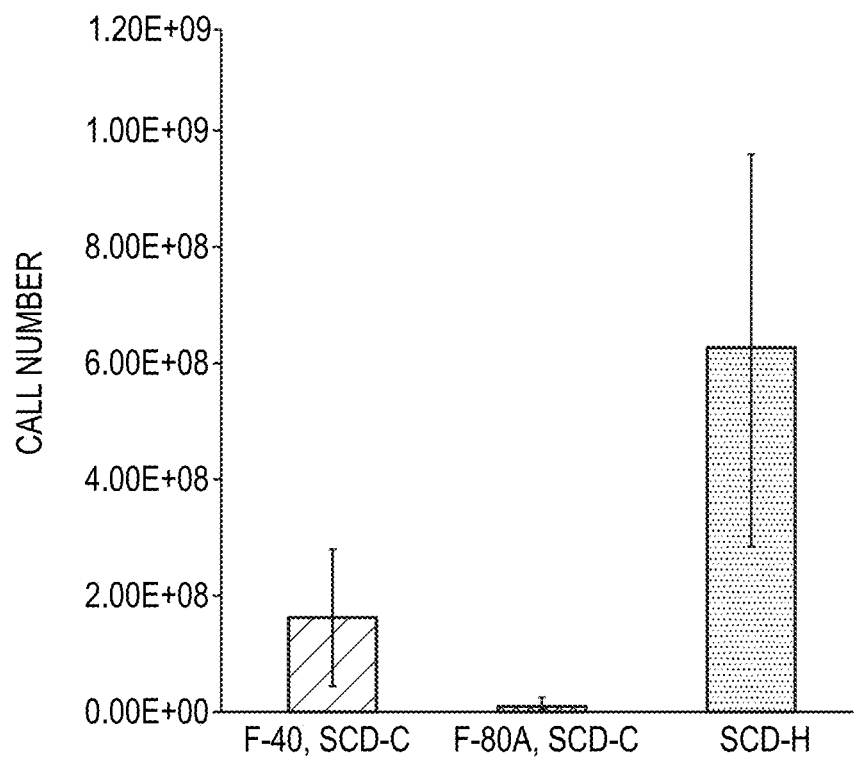
FIGS. 10A and 10B are bar graphs depicting the number (FIG. 10A) and distribution (FIG. 10B) of cells eluted from SCD membranes following their use in SCD devices to treat septic subjects. The subjects were treated with an F-40 SCD device in the presence of heparin (SCD-H); an F-40 SCD device in the presence of citrate (F-40 SCD-C); or an F-80A SCD device in the presence of citrate (F-80A SCD-C).
Figure 10B:
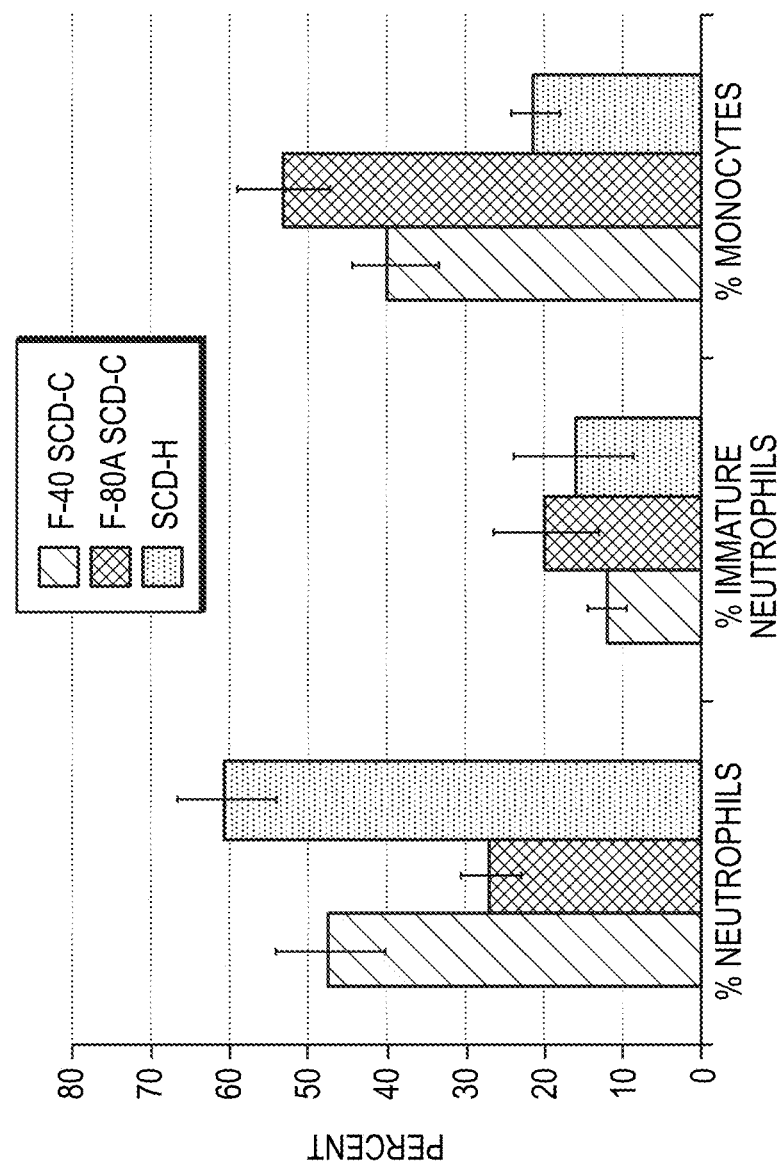

To assess the sequestration of activated leukocytes along the SCD membranes, the SCD cartridges were processed for histologic evaluation at the conclusion of the porcine sepsis study. The light microscopy findings depicted in FIG. 9 clearly showed leukocyte attachment and aggregation along the outer surface of the SCD membranes. To determine the amount and type of adherent leukocytes, the devices were processed and cells eluted off the membrane at the end of the treatment period. The number of white blood cells (WBCs) eluted off the SCD-H and SCD-C, F-40 cartridges were $6.44\pm3.4\times10^8$ and $1.72\pm1.20\times10^8$ cells (FIG. 10A) (p<0.05), respectively, indicating that citrate anticoagulation reduced the number of adherent leukocytes. Furthermore, the distributions of eluted cells were 79±5% neutrophils and 21±4% monocytes in the SCD-H group as compared to 55±4 neutrophils and 30±5% monocytes in the SCD-C, F-40 group (FIG. 10B). Surprisingly, an average of $1.88\pm1.21\times10^7$ cells were eluted off from the cartridges of the SCD-C, F-80A group (FIG. 10A), which was about ten fold lower than the average number of eluted cells from the SCD-C, F-40 group. Thus, even though the substantially larger membrane surface area of the F-80A might have led to increased retention of leukocytes, the SCD cartridge's efficiency in deactivating leukocytes apparently led to a dramatic reduction in leukocyte retention by the end of the procedure. An average of $8\times10^6$ cells were eluted from the cartridges of non-septic control animals (n=2), suggesting that most of the cells that were sequestered in the cartridges of the SCD-H and SCD-C groups were activated leukocytes. The SCD-C group had fewer than $2\times10^4$ cells eluted from lumens of the cartridges with luminal blood perfusion.

Figure 11A:
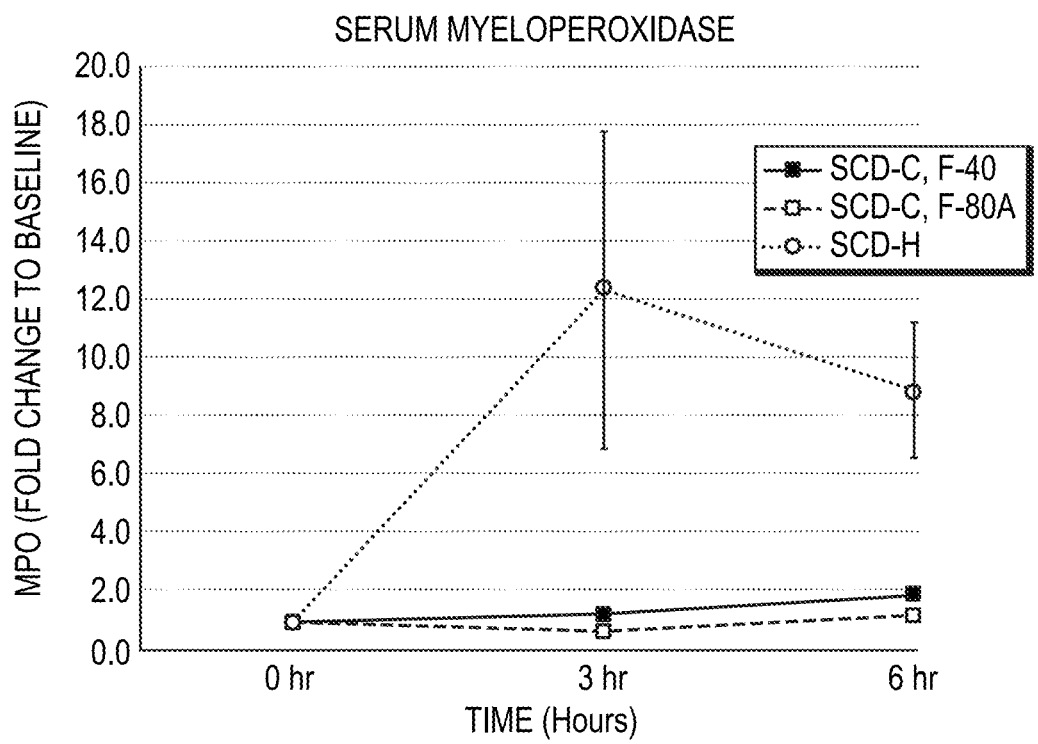
FIGS. 11A-B are graphical depictions of levels of serum myeloperoxidase (FIG. 11A) or systemic neutrophil activation, as measured by CD11b mean fluorescent intensity (FIG. 11B) shows hematocrit levels in subjects with sepsis treated with an F-40 SCD device in the presence of heparin (SCD-H) or with an F-40 or F-80A SCD device in the presence of citrate (SCD-C).
Figure 11B:
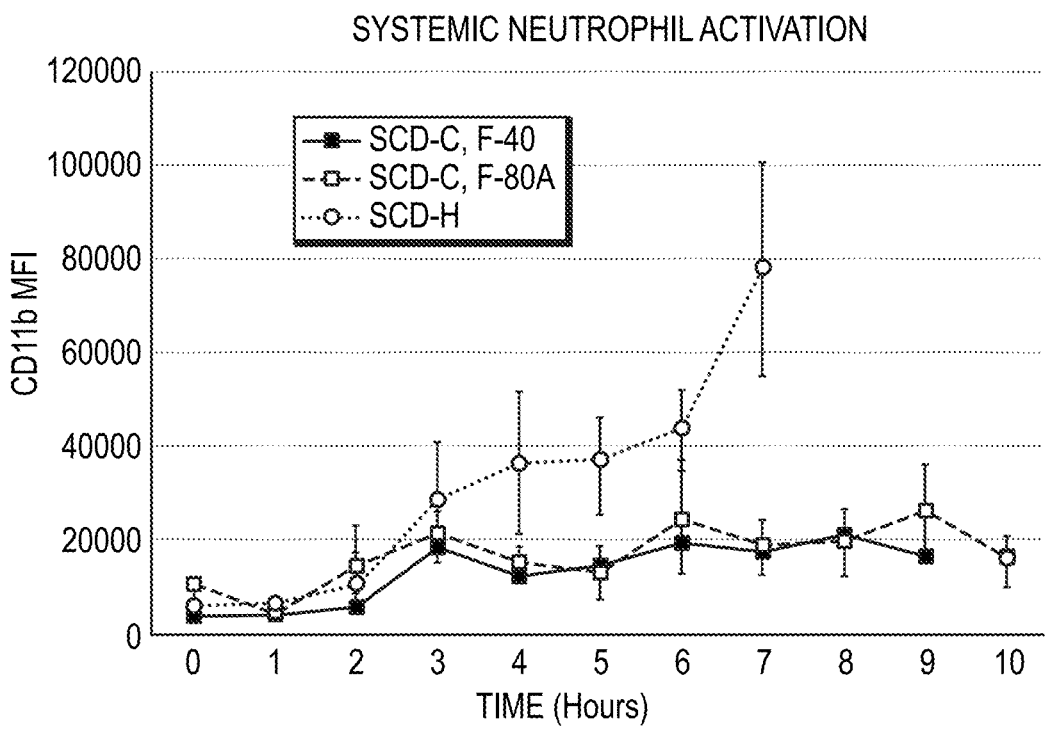

In order to determine whether the SCD cartridge with citrate anticoagulation can influence the activity of neutrophils in the systemic circulation, biomarkers of neutrophil activation were assessed. Activated neutrophils release various enzymes in response to invading microbes or tissue injury. Since the dominant enzyme released from neutrophil granules is myeloperoxidase (MPO) (Klebanoff, S. J., et al., (2005) LEUKOC. BIOL. 77(5): 598-625), blood MPO levels reflect the level of neutrophil activation. As depicted in FIG. 11A, plasma MPO levels in the SCD-C groups were significantly lower compared with the SCD-H group, reflective of a lower level of activated neutrophils. Furthermore, the SCD-C, F-80A group showed the lowest level of MPO. Systemic circulating neutrophil activation was also assessed by measuring the amount of CD11b expression on circulating neutrophils. CD11b is a membrane protein involved in the adherence of leukocytes to activated endothelium at the site of inflammation (Fan, S. T., et al., (1993) J. IMMUNOL., 150(7): 2972-2980). As depicted in FIG. 11B, the amount of CD11b expression on circulating neutrophils was dramatically decreased in the SCD-C groups compared to the SCD-H groups (p=0.03), indicating a lower level of neutrophil activation.

Figure 12A:
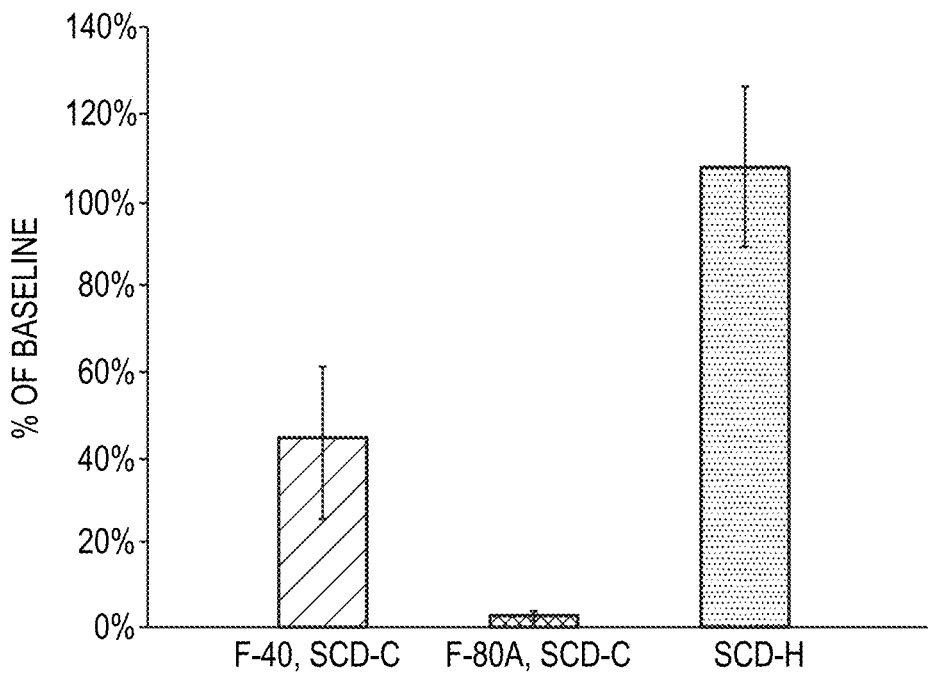
FIGS. 12A-B are graphical depictions of release of IL-8 (FIG. 12A) and TNF-α (FIG. 12B) from peripheral blood mononuclear cells isolated from subjects after 6 hours of treatment for sepsis with an F-40 SCD device in the presence of heparin (SCD-H); an F-40 SCD device in the presence of citrate (F-40 SCD-C); or an F-80A SCD device in the presence of citrate (F-80A SCD-C).
Figure 12B:
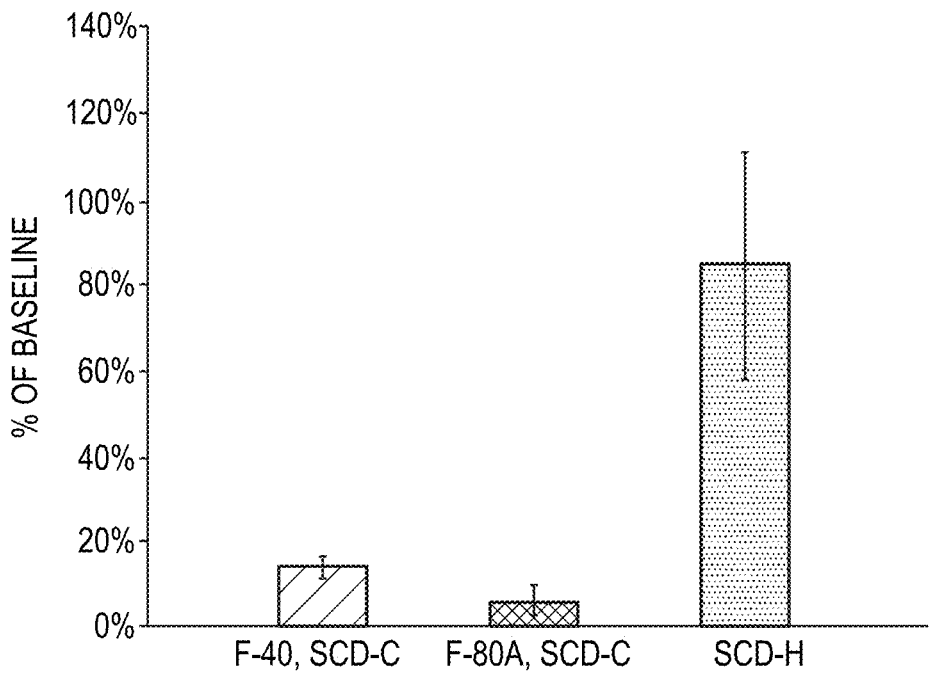

To further assess the immunomodulatory effect of the SCD cartridge and regional citrate coagulation, systemic cytokine levels were evaluated. Serum levels of various cytokines including IL-1β, IL-6, IL-8, IL-10, TNF-α and IFN-γ were not significantly different between the SCD-H and the SCD-C groups, although the pro-inflammatory cytokines IL-1β and IL-8 appeared to be slightly higher in the SCD-H group. Since the SCD device also sequesters monocytes, PBMCs were isolated and assessed for cytokine release. Prior to sepsis induction, PBMC release of TNF-α and IL-8 in response to LPS were 2.1±1.8 and 6.5±2.8 pg/$10^6$ cells, respectively, in the SCD-H group; in the SCD-C group, the release was 5.1±0.9 and 18.7±8.1 pg/$10^6$ cells, respectively. At 6 hours post sepsis, PBMC release of TNF-α and IL-8 in response to LPS was significantly lower in the SCD-C groups as compared to the SCD-H group (p<0.05) (FIGS. 12A and 12B). These results indicated that the overall pro-inflammatory cytokine profile in the septic state was dampened in the SCD-C groups. Again, it appeared that the SCD device having a membrane surface area of 2.5 $m^2$ had the greatest immunomodulatory effect.

Figure 13:
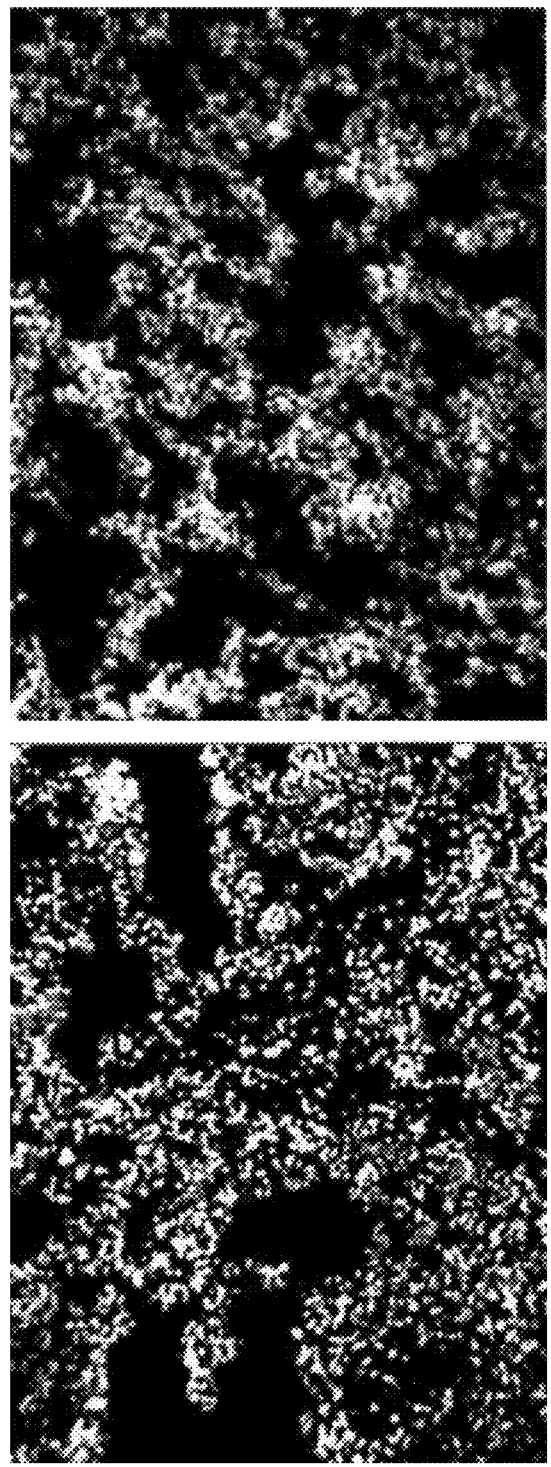
FIG. 13 is a photograph of lung sections incubated with primary anti-CD11b antibody, followed by incubation with an anti-mouse IgG Alexafluor594 conjugate. Nuclei were counterstained with DAPI. The left panel is from a subject treated for sepsis with an F-40 SCD device in the presence of heparin; the right panel is from a subject treated for sepsis with a SCD device in the presence of citrate. A significant decrease in CD11b-labeled cells was observed in the lungs of the patients whose regimen included citrate rather than heparin.
Figure 14:
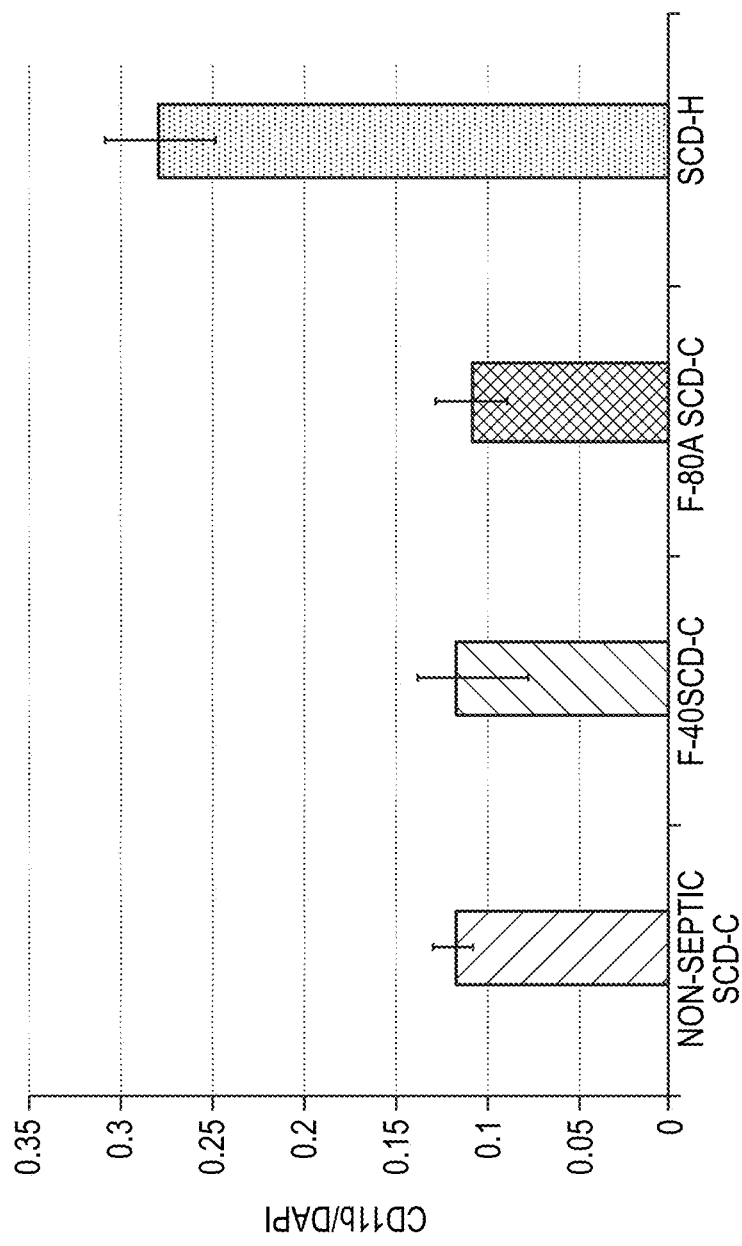
FIG. 14 is a bar graph depicting the number of CD11b-positive cells detected in non-septic subjects; septic subjects treated with an F-40 SCD device in the presence of citrate (F-40 SCD-C); septic subjects treated with an F-80A SCD device in the presence of citrate (F-80A SCD-C); or septic subjects treated with an F-40 SCD device in the presence of heparin (F-40 SCD-H).

Previous studies have reported that the lung was the first organ targeted for activated leukocyte sequestration and infiltration after endotoxemia or sepsis (Welbourn, C. R. et al., (1992), BR. J. SURG., 79(10): 998-1003; Andonegui, G., et al., (2009), J. CLIN. INVEST., 119(7): 1921-1930). Thus, we evaluated the effect of the SCD device and citrate anticoagulation on the sequestration of activated leukocytes in lung tissues. As demonstrated in FIG. 13, a significant decrease in CD11b-labeled cells in the lung was observed in the SCD-C group compared to the SCD-H group. Further, a histomorphometric analysis showed that the ratios of percent CD11b-positive area by percent DAPI-positive area in the SCD-C group and SCD-H group were 0.114±0.21 versus 0.334±0.052 (p=0.007), respectively (FIG. 14). Together, these results indicated a reduced lung sequestration of activated leukocytes in animals treated with the SCD device and citrate.

Figure 15A:
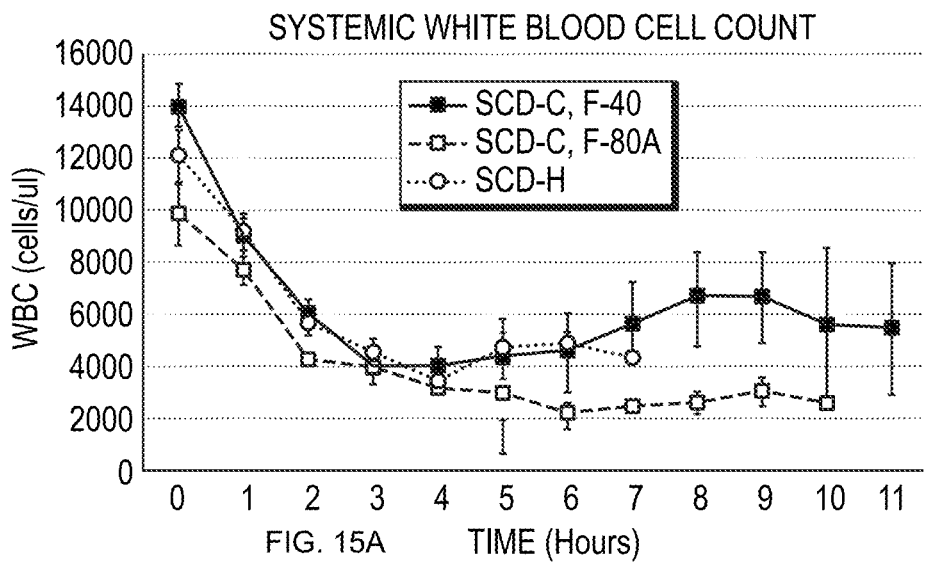
FIGS. 15A-C are graphical depictions of systemic white blood cell counts (FIG. 15A), systemic absolute neutrophil counts (FIG. 15B), and systemic immature neutrophil counts (FIG. 15C) over time in septic subjects treated with an F-40 SCD device in the presence of citrate (SCD-C, F-40), with an F-80A SCD device in the presence of citrate (SCD-C, F-80A), or with an F-40 SCD device in the presence of heparin (SCD-H).
Figure 15B:
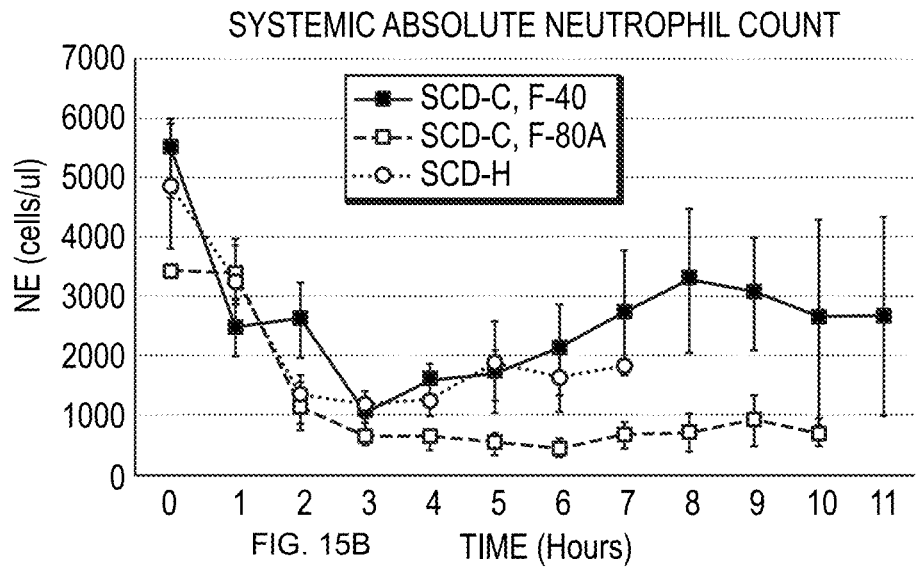
Figure 15C:
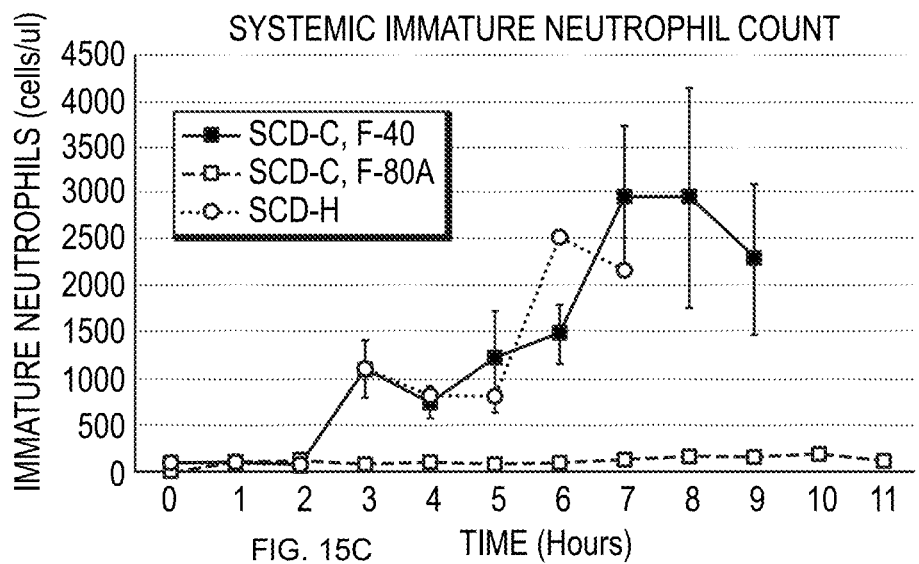

White blood cell (WBC) kinetics may also provide insights into the manner in which the SCD device may influence leukocyte response to infection. To determine the kinetics of the circulating pool of leukocytes in the SCD-H and SCD-C groups, absolute WBC and neutrophil counts were measured (FIG. 15). Both the SCD-H and SCD-C, F-40 groups reached a nadir of 1125±240 and 1094±166 neutrophils/$mm^3$ at 3 hours post sepsis induction, respectively. These groups did not reach absolute neutropenia (defined as counts below 500) due to an increase in immature neutrophils from the bone marrow, as determined by manual examination of blood smears, beginning at 3 hours post sepsis induction. Notably, the SCD-C, F-80A, group consistently exhibited a low neutrophil count reaching a nadir of 457±77 at 6 hours. This was due to a markedly diminished release of immature neutrophils from the bone marrow, suggesting that the SCD device with a larger surface area may function to alter the kinetics of bone marrow release of immature neutrophils. The Con-citrate F-40 group had a similar decline and rebound of leukocyte counts as the SCD-H F-40 group, whereas the NS-control animals tended to have neutrophilia, with neutrophil counts rising from approximately 4,000 to 14,000 over the 8-hour evaluation period.

Figure 16:
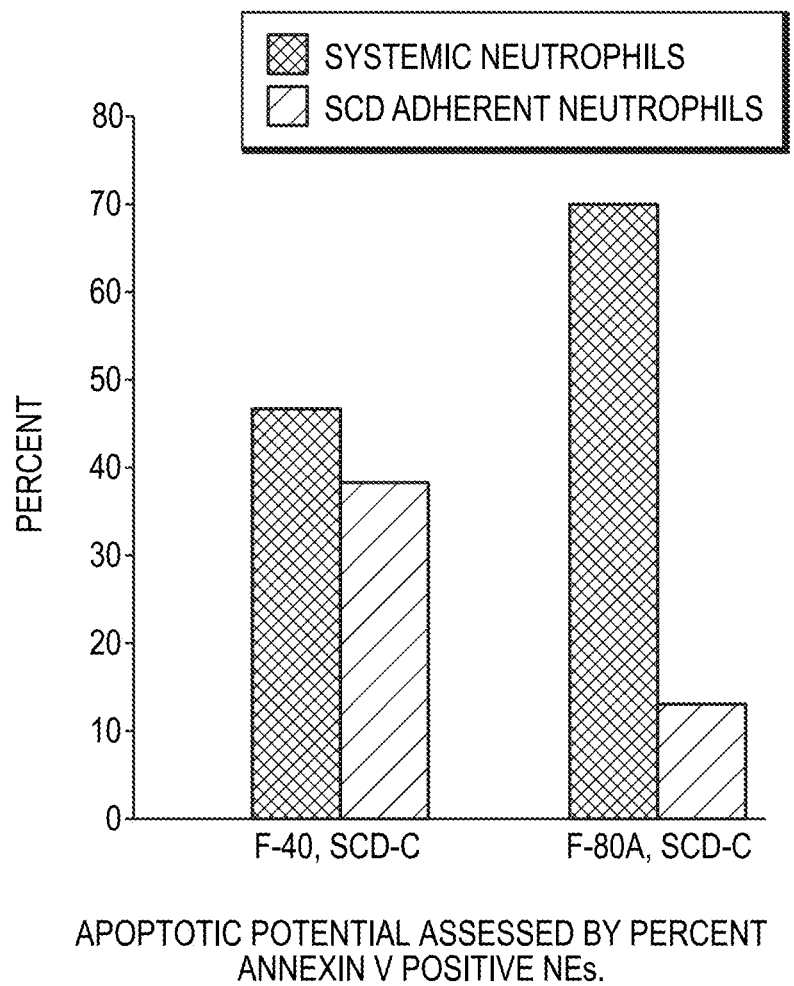
FIG. 16 is a bar graph depicting the percentage of neutrophils that were detected as positive for annexin V, as an assessment of the apoptotic potential of the cells. Both systemic neutrophils and SCD-adherent neutrophils were measured following treatment of septic patients with an F-40 SCD (F-40 SCD-C) or an F-80A SCD (F-80A SCD-C) in the presence of citrate.

Under septic conditions, activated neutrophils have an increased lifespan with a delay in apoptosis. The apoptotic potential of the circulating and adherent leukocytes isolated from the SCD-C groups was assessed. As shown in FIG. 16, the SCD-C, F-80A group had a higher number of apoptotic circulating neutrophils as compared to the SCD-C, F-40 group, suggesting that this SCD device with the larger membrane surface area decreased the activation state of circulating neutrophils. On the other hand, the SCD-C, F-80A group had fewer apoptotic SCD-cartridge-adherent neutrophils, suggesting that this SCD device selectively sequestered activated neutrophils thus removing them from the circulating pool.

Together, the above results demonstrated the efficacy of the SCD device combined with citrate in ameliorating cardiovascular instability, reducing renal dysfunction, and improving survival time in a porcine model of septic shock. More importantly, these results demonstrated that a SCD cartridge having larger sequestration area is more effective in alleviating the complications associated with sepsis.

Example 2. In Vitro Studies of Leukocyte Sequestration and Deactivation

This example describes in vitro experiments to evaluate the effect of the SCD device on leukocyte sequestration and activation.

(I) Methods and Materials

A—In Vitro Assessment of Leukocyte Interaction with the Membrane of a SCD Cartridge A custom microscopic flow chamber system was set up to enable microscopic analysis of leukocyte interaction with the SCD membrane. The flow chamber consisted of a polycarbonate housing with an inlet and outlet for perfusion. A polysulfone membrane was affixed to the polycarbonate block with a gasket which directed shear flow. The thickness of the gasket (100 μm) along with the length (2 cm) and the width of the channel (1.5 mm) determined the volume of the flow chamber. Microscopic imaging was accomplished through an optical window made up of a cover glass affixed to the bottom of the polycarbonate block. Either isolated blood or purified leukocytes were used for this study.

Isolated blood was prone to activation from excessive handling. Thus, 5 mL of fresh heparinized porcine blood was minimally manipulated prior to the flow chamber study. Briefly, leukocytes were fluorescently labeled using 50 μg/mL of Hoechst 33342 dye. Further, the leukocytes were activated by adding 1 μg/ml lipopolysaccharide (LPS) directly to the blood samples. Similarly, 125 μL of Anticoagulant Citrate Dextrose Solution USP (ACD) Formula A (Baxter) was added to 5 mL of isolated blood and ionized calcium levels were measured prior to microscopic flow analysis with i-stat EG-7+ cartridges. Blood passed through the flow chamber at a rate of 20 μL/min with calculated shear forces between 1-10 dynes/cm$^2$. For each isolated blood sample, sequences were acquired in triplicate.

Microscopic analysis of cell capture events was accomplished using either a Zeiss Axiovert 200M or Axio-Observer epifluorescence microscope equipped with a microscope stage-top incubator to control environmental temperature and $CO_2$ content. Fluorescence images were acquired with either a Zeiss MRm3 or an Icc1 camera at a frequency of 1 frame/second for 5 minutes, for analysis of leukocyte/membrane interaction, and at 1 frame/minute for 1 hour sequences, for analysis of long term leukocyte attachment. Frame by frame evaluation of leukocyte rolling, attachment and detachment of leukocytes was carried out to determine the total number and duration of these phenomena. An attachment event was defined as when a leukocyte appeared in the same location for multiple frames within a sequence. Detachment was defined as release events associated with previously defined attached leukocytes. Rolling events were defined by identifying the same leukocyte in multiple sequence frames within a sequence where the leukocyte was not in same exact location, but in close proximity to the prior location.

B—Assessment of In Vitro Leukocyte Activation

Heparinized human whole blood was added to tubes with or without lipopolysaccharide (LPS) (10 μg/mL) or formyl-Methionyl-Leucyl-Phenylalanine (fMLF, 50 nM). Citrate anticoagulation was achieved by adding citrate dextrose solution (ACD) to the tubes (Damsgaard, C. T., (2009) J. IMMUNOL. METHODS, 340(2): 95-101; Wutzler, S., (2009) J. TRAUMA, 66(5): 1273-1280). The release of IL-6, IL-8, or IL-10 was measured using commercially available ELISA kits from R&D Systems. The release of elastase was measured using a commercially available ELISA kit from Bender MedSystems. The release of lactoferrin was measured using a commercially available ELISA kit from EMD Chemicals. The iCa levels were measured using an I-STAT reader and were confirmed to be ≤0.25 mM and 1.25 mM in the citrate treated or nontreated samples, respectively. Samples were incubated for various times at 37° C. and 5% $CO_2$. CD11b activation was measured using an FITC-conjugated mouse anti-human antibody (AbD Serotech) and evaluated on an Accuri C6 flow cytometer.

(II) Results and Discussion

A—Observation of Leukocyte Parameters

Figure 17:
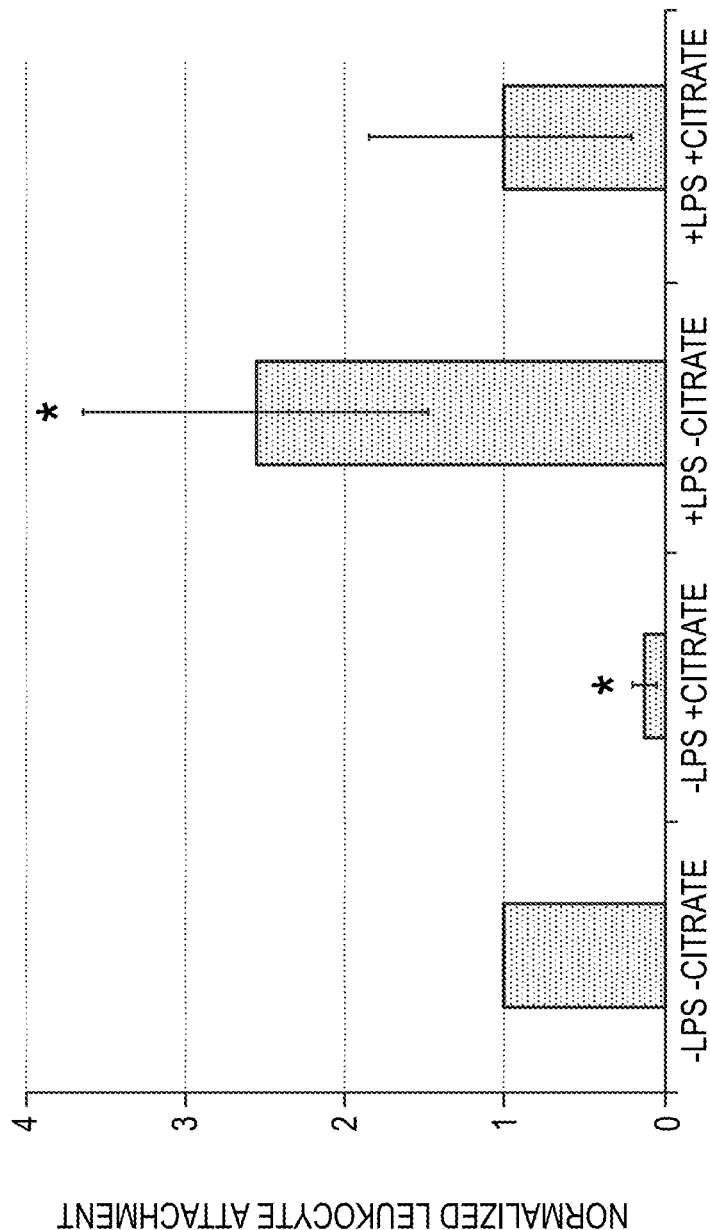
FIG. 17 is a bar graph depicting the relative numbers of leukocytes attaching to polysulfone in the presence of shear flow and in the presence or absence of lipopolysaccharides (LPS) and/or citrate.

To assess the interactions of leukocytes and the SCD polysulfone membranes, a customized flow chamber with video microscopy was set up. The addition of citrate lowered blood iCa level from 1.32±0.05 mmol/L to 0.32±0.05 mmol/L. Analysis of leukocyte attachment events confirmed that LPS activation of the leukocytes in the absence of citrate significantly increased leukocyte attachment to polysulfone membranes during shear flow (p<0.05, FIG. 17). In citrate-treated, low ionized calcium flow chambers, a statistically significant decrease in leukocyte attachment was observed (p<0.05), suggesting that leukocyte adhesion to polysulfone membranes may be ionized calcium dependent. These results were consistent with the ex vivo data in the above-described sepsis porcine model, in which citrate-treated membrane cartridges had fewer adherent leukocytes at the end of the studies. In addition, preliminary analysis of 1 hour sequences demonstrated far fewer persistent leukocyte adhesion events for LPS and citrate treated blood compared to blood treated with LPS only. However, there was an observed increase in rolling events for the LPS and citrate treated blood. This suggested a catch and release phenomena when leukocytes interact with the polysulfone membrane in the presence of citrate.

Experiments were carried out to assess the effects of citrate-promoted reductions in blood iCa on leukocyte activity. Specifically, an in vitro whole blood assay system was utilized (Damsgaard, C. T., (2009) J. IMMUNOL. METHODS, 340(2): 95-101; Wutzler, S., (2009) J. TRAUMA, 66(5): 1273-1280) to assess the effects of lowered blood iCa levels on leukocyte cytokine production (IL-6, IL-8, IL-10) and the release of preformed inflammatory proteins from neutrophil exocytotic vesicles (lactoferrin, elastase). The results are summarized in Table 6.

TABLE 6

Effect of citrate on leukocyte activation parameters

|  | IL-6 (ng/mL) n = 7 | IL-8 (ng/mL) n = 5 | IL-10 (ng/mL) n = 4 | Lactoferrin (mg/mL) n = 4 | Elastase (mg/mL) n = 5 | CD11b (MFI × 10³) n = 3 |
|---|---|---|---|---|---|---|
| Baseline | | | | | | |
| Heparin | 0.18 ± 0.04 | 0.0 ± 0 | 0.11 ± 0.07 | 8.47 ± 1.54 | 2.73 ± 0.29 | 22.55 ± 1.06 |
| Citrate | 0.38 ± 0.15 | 0.59 ± 1.51 | 0.01 ± 0.01 | 1.67 ± 0.29* | 0.94 ± 0.14§ | 7.32 ± 0.47§ |
| Stimulated (LPS, fMLF) | | | | | | |
| Heparin | 65.42 ± 19.77 | 34.18 ± 6.66 | 3.74 ± 0.94 | 12.42 ± 1.08 | 4.52 ± 0.54 | 53.43 ± 3.12 |
| Citrate | 28.99 ± 7.60* | 3.45 ± 2.30† | 2.06 ± 0.84† | 3.43 ± 0.18§ | 0.91 ± 0.28** | 28.72 ± 2.95§ |

*$p < 0.05$;
†$p < 0.02$;
**$p < 0.005$;
§$p < 0.002$, as determined with paired t-test between heparin and citrate groups.

As shown in Table 4, lowering iCa with citrate inhibited the release of cytokines (IL-6, IL-8, IL-10) and neutrophil exocytotic proteins, suggesting that a low iCa environment promoted the deactivation of leukocytes.

Example 3. Use of SCD Device During Cardiopulmonary Bypass Surgery

Systemic Inflammatory Response Syndrome (SIRS) can occur in association with cardiopulmonary bypass (CPB) surgery, resulting in multiple organ dysfunction (MOD). Activated neutrophils have been implicated as major inciting factors in this process. This example describes in vitro and in vivo experiments that evaluate the effect of SCD cartridges for use during CPB surgery. The results demonstrate that the usage of SCD cartridges may disrupt the systemic leukocyte response during CPB surgery, leading to improved outcomes for CPB-mediated MOD.

(I) Background

Leukocytes, especially neutrophils, are major contributors to the pathogenesis and progression of many clinical inflammatory disorders, including systemic inflammatory response syndrome (SIRS), sepsis, ischemia/reperfusion injury, acute respiratory distress syndrome (ARDS) and acute kidney injury (AKI). Cardiac surgical advances have been dependent upon the techniques for cardiopulmonary bypass (CPB). It has been recognized that a systemic inflammatory response occurs in association with CPB, resulting in multiple organ dysfunctions (MOD) following surgery. Multiple insults during CPB have been shown to initiate and extend this inflammatory response, including artificial membrane activation of blood components (membrane oxygenator), surgical trauma, ischemia-reperfusion injury to organs, changes in body temperature, blood activation with cardiotomy suction, and release of endotoxin. These insults promote a complex inflammatory response, which includes leukocyte activation, release of cytokines, complement activation, and free-radical generation. This complex inflammatory process often contributes to the development of acute lung injury, acute kidney injury, bleeding disorders, altered liver function, neurologic dysfunction, and ultimately MOD.

The mechanisms responsible for MOD following CPB are numerous, interrelated and complex, but growing evidence suggests a critical role in the activation of circulating blood leukocytes, especially neutrophils in the development of ARDS in CPB-induced post-pump syndrome. Sequestered and activated neutrophils migrate into lung tissue, resulting in tissue injury and organ dysfunction. The importance of activated leukocytes and microvascular dysfunction has also been demonstrated to be important in acute kidney injury.

In this regard, the use of leukocyte depleting filters within an extracorporeal blood circuit during CPB has been developed and evaluated in preclinical animal models and clinical studies. While filters remove leukocytes in vitro, they do not appear to consistently deplete leukocyte concentrations in vivo. The majority of papers reported no significant reduction in circulating leukocytes, a conclusion similarly drawn by meta-analysis. Acknowledgement of "filter exhaustion," a progressive decrease in leukocyte reduction efficiency during CPB has been repeatedly observed during experimental evaluation.

The instant invention utilizes a biomimetic membrane called the selective cytopheretic device (SCD) and regional citrate anticoagulation to promote a decrease in activated leukocytes in animals and patients suffering from acute inflammation. Early pre-clinical and clinical results, suggest that the device ameliorates the MOD effects of SIRS and impacts the mortality rate of multiorgan failure in intensive care unit (ICU) patients. Results described herein demonstrate that the SCD reduces the circulating level of neutrophils and reduces markers of neutrophil activation, both in vitro and in vivo.

(II) Methods and Materials

A—Selective Cytopheretic Device (SCD)

The SCD tested was a polycarbonate housing containing porous polysulfone hollow fibers with an inner diameter of 200 μm, a wall thickness of 40 μm, and a molecular weight cutoff of 40 to 50 kDa. Blood flow was directed to the extracapillary space (ECS). The SCDs used had outer membrane surface area (SA) of 2.2 m² and 2.6 m², and surface area/inner volume (SA/IV) ratios of 486 cm⁻¹ and 508 cm⁻¹, respectively. The SCDs were supplied by CytoPherx, Inc. (Ann Arbor, Mich.).

B—In Vitro Blood Circuit Studies

In vitro blood circuit studies were initiated to compare two leukocyte reducing membrane systems, the Pall Leukogard LGB (Ann Arbor, Mich.) and the SCD device in a series of 10 paired studies. Fresh, heparinized bovine blood (5-6 L) was collected in a 7 L silicone drain bag (B Braun Medical Inc. Bethlehem, Pa.) with 90,000 IU sodium heparin (Clipper Distributing LLC, Saint Joseph, Mo.) and divided evenly into two identical drain bags, which served as reservoirs for two separate blood circuits, each to test the respective device. The in vitro blood circuits utilized FDA approved Tygon lines (Cole-Parmer, Vernon Hills, Ill.). The circuits were set up to monitor temperature with type T thermocouples, and pressure measurements with a 4 channel 90XL (Mesa Labs, Lakewood, Colo.), pre- and post-device during perfusion. Both blood reservoirs were warmed in the same water bath (34.5° C.) to insure identical heating behavior, and a handheld IR-pyrometer was employed to measure internal temperatures (approximately 31° C.) within each device tested. Peristaltic blood pumps (Fresenius 2008H, Walnut Creek, Calif.) maintained a constant flow rate of 300 mL/min in both circuits.

Blood samples were obtained every 15 minutes to measure total white cell, neutrophil, and platelets as previously described, as well as for other assays. For plasma myeloperoxidase (MPO) and free hemoglobin (Hgb) analysis, blood samples were immediately cooled and centrifuged free of cells. Plasma hemoglobin concentration was chemically determined using a colorimetric assay with 3,3', 5,5', tetramethylbenzidine (TMB), and MPO was measured by ELISA. At the end of the experiment, the circuit was disconnected and normal saline flushed continuously through the extracapillary space (ECS) of the SCD until fluid was free of visible blood, and then the SCD was eluted to quantify adherent cells as previously described. A similar process was also conducted to elute LGB filters.

C—In Vivo Cardiopulmonary Bypass Model

Wisconsin calves (100-110 kg) were premedicated with atropine (0.04 mg/kg), and ketamine (25 mg/kg) administered by intramuscular (IM) injection, and then anesthetized with 5 µg/kg of thiopental. After intubation with an endotracheal tube (Mallinckrodt Company, Mexico City, Mexico), ventilation was established with a volume cycle ventilator. Anesthesia was maintained by continuous infusion of 5 mg/kg/h of thiopental and 20 µg/kg/h of fentanyl. Muscle relaxation was induced with 0.2 mg/kg of pancuronium followed by intermittent reinjections at 0.1 mg/kg. Polyethylene monitoring lines were placed in the external jugular vein and the femoral artery and vein. Median sternotomy was performed. A 16 to 20 mm Transonic perivascular flow probe was placed on the main pulmonary artery, and Millar microtip pressure transducers were placed in the pulmonary artery and left atrium. Prior to initiating cardiopulmonary bypass, baseline pulmonary artery pressure and flow rate and left atrial pressure readings were taken for determination of cardiac output. After systemic heparinization (300 U/kg), an 18 F Medtronic DLP arterial cannula was placed in the left carotid artery and a 24 F Medtronic DLP single-stage venous cannula was placed in the right atrium.

The CPB circuit was primed with 1,000 mL of lactated Ringer's solution and 25 mEq of $NaHCO_3$. The circuit consisted of a Sams roller blood pump, a Medtronic Affinity hollow fiber oxygenator with integral heat exchanger, and a cardiotomy reservoir. A Medtronic Affinity 38-µm filter was placed in the arterial limb to capture particulate debris. The left ventricle was vented using a 12-Ga Medtronic standard aortic root cannula with vent line connected to a Sarns roller pump and the cardiotomy reservoir. Cardiopulmonary bypass was initiated, ventilation was discontinued, and systemic perfusion maintained at 2.4 L/min/m² body surface area. Moderate perfusion hypothermia (32° C. rectal temperature) was used, and mean aortic pressure kept at 60-80 mmHg by modification of flow and intravenous phenylephrine infusion (0-2 µg/kg/min). The ascending aorta was cross clamped. CPB was maintained for 255 minutes.

Three groups of animals were evaluated: CPB circuit without SCD, CPB circuit with SCD, and CPB circuit with SCD with citrate/calcium regional perfusion to provide a low ionized calcium (iCa) blood environment only along the SCD circuit. The SCD circuit blood flow was controlled at 200 m/min with an AK12 blood pump system (Gambro). Citrate/calcium infusion was based upon well developed clinical protocols for citrate regional anticoagulation, as previously described.

Similar to the in vitro blood circuit studies, for all sample times systemic blood was used to assess CBCs. The SCD or LGB was routinely removed at T=225 minutes, with a final blood sample taken 15 minutes after removal to evaluate post therapy dynamics. Total manual white cell counts were determined using the Unopette system (BD Biosciences) and manual differentials were determined from blood smears after ethanol fixation and Wright stain (Richard-Allen Scientific). After each study, if a SCD or LGB was used, adherent cells were eluted and quantified as previously described.

D—Statistical Analysis

Analysis of variance (ANOVA) was conducted for all studies with statistical significance of $p<0.05$.

(III) Results and Discussion

A—In Vitro Blood Circuit Studies

The temperature of the blood was similar between the SCD and LGB circuits throughout the study, averaging 31.1±0.4° C. and 31.1±0.3° C., respectively. The pressure profile across the devices were 92.0±49.1 and 29.2±16.2 mmHg for pre- and post-SCD with a pressure drop of 62.9±39.8, and 98.8±71.5 and 40.1±17.1 pre- and post-LGB, with a pressure drop of 31.3±3.9 mmHg. The variability in pressures was related to differences in the hematocrit of blood in the circuit, which averaged 31.1±3.9%.

The total white cell counts for the LGB circuits dropped by greater than 50% within the first 15 minutes and remained steady to the end of the experiment. This decline is largely the result of a more than an 80% drop in circulating neutrophils. The SCD circuits showed a substantial, but smaller drop in total white cells and neutrophils during the experiment, with the neutrophil counts declining between 40% and 60%. Differential white blood cell counts from each device were evaluated. Monocyte and eosinophil concentrations also declined, but due to their low percentages in circulating blood, accurate quantification was challenging. A substantial decline in the number of platelets was observed, with the SCD and LGB in particular, displaying a relative platelet reduction of greater than 80% at 15 minutes. However, in both cases the platelet count rebounds to a level equivalent to approximately 50% of the platelet counts enumerated prior to beginning the experiment.

B—In Vitro Blood Circuit Device Elution

The total number of cells eluted from LGB and SCD were counted. Twice as many cells were recovered from LGB than the SCD. The percentage of neutrophils, monocytes, and eosinophils in the closed circulation loop that were recovered from each device were calculated. The total number of each leukocyte population recovered from each device was divided by the total number of each leukocyte population present in blood prior to the initiation of each experiment. The Mean±SEM for neutrophils, monocytes, and eosinophils are shown for 10 SCD and 10 LGB. Neutrophils outnumbered monocytes roughly 2 to 1, while eosinophils were present at a variable and much smaller number and percentage from both leukocyte filters. More neutrophils and monocytes were eliminated from LGB versus SCD.

Total cell numbers remaining in the blood at the termination of each experiment were added to the cell numbers eluted from the device and compared with the number of cells present in the blood sample at the beginning of the experiment. The difference in these numbers is reported as the "change of total cell number" and is most likely to indicate the number of cells destroyed during the four hour circulation experiment. Significantly more cells were unaccounted for in the circuits employing the LGB than in the case of the SCD (P<0.05). The data are presented as the mean±SEM of 10 paired experiments.

C—In Vitro Blood Circuit Blood Biocompatibility

Neutrophil released myeloperoxidase (MPO) activity was assayed as the mean±SEM for SCD (N=8), and for LGB (N=10) in μg/ml. Plasma MPO activity was significantly higher for the LGB relative to the SCD, with a peak at the first sampling time after circuit initiation (7.45±3.02 μg/mL) and continued to be elevated for the remainder of the experiment (p<0.05). SCD circuit MPO values remained below 0.4 μg/mL at all times. Free hemoglobin (Hgb) in plasma, a measure of hemolysis is also assessed, as the mean±SEM for LGB (N=10) and SCD (N=10) in mg/mL, with a peak at the first sampling time after circuit initiation (0.06±0.04 mg/mL) and elevated levels throughout. SCD circuit free hemoglobin values remained below 0.005 mg/mL at all times.

D—In Vivo Bovine Calf Model of CPB

Systemic white blood cell (WBC) counts are assessed for the CPB in vivo bovine studies. In the CPB No SCD control group, WBC increased above the baseline level counts after 90 minutes and peaked with nearly double the baseline WBC. For device treated groups, WBC counts decreased in the first hour of CPB. In the SCD heparin treatment group, following this initial reduction, the WBC gradually increased after 60 minutes, and throughout CPB, with a sharp raise after removing SCD (routinely at t=225 min) for the final measurement 15 minutes thereafter. Similar results were observed when LGB was placed in the circuit rather than the conventional arterial line filter (data not shown). In SCD citrate group, WBCs were low throughout CPB, and even after the SCD was removed.

Quantification of the neutrophil population during cardiopulmonary bypass (CPB) surgery without a SCD showed an approximate 5-fold rise in the systemic levels. SCD treatment with only systemic heparin coagulation during CPB dramatically reduced the systemic neutrophil concentration during the first 120 min, but was followed by a steady rise until SCD removal (routinely at t=225 min), with a larger increase 15 minutes after SCD removal. SCD with regional citrate during CPB resulted in a systemic neutrophil concentration approximately 75% lower than the pre-SCD level, which persisted throughout CPB, and remained low 15 minutes after SCD removal.

At the conclusion of SCD therapy, SCD were thoroughly washed and bound leukocytes were eluted and enumerated. On average $8 \times 10^7$ and $1.63 \times 10^9$ leukocytes were eluted from the SCD employing regional citrate or systemic heparin, respectively. Eluted cells were of the granulocytic lineage independent of the use of regional citrate, on average consisting of approximately 80% neutrophils, 20% monocytes, and variable amounts of eosinophils, typically <2%, similar to distributions reported in in vitro blood circuit studies. Preliminary results from the quantification of immature neutrophils by manual counts demonstrate a trend of low counts for the SCD-Citrate group at the end of 240 minutes of CPB (230, 0 per μL, n=2) wheras SCD-Heparin (1630, 6300, 1390 per μL, n=3), No SCD (160, 2660 per μL, n=2) and LGB (1760, 3880 per μL, n=2) groups all have cases of increased amounts of immature neutrophils.

E—Discussion

CPB promotes SIRS often resulting in MOD. This inflammatory disorder arises from multifactorial processes, but circulating leukocyte activation is postulated to play a central role. Therapeutic interventions directed toward leukocyte depletion during CPB have been evaluated both in pre-clinical and clinical studies. The results have been inconsistent with regards to reducing circulating leukocyte counts and alleviating progression to MOD.

An in vitro test circuit was developed to assess leukocyte depletion in a circulating heparinized blood circuit between 31° C. and 34.5° C. and comparable blood flow rates of 300 ml/min. When integrated into the blood circuit, both the LGB and SCD prompted a significant reduction in circulating white blood cell and neutrophil counts with the LGB group having a greater effect to lower WBC counts compared to the SCD. This reduction in leukocyte counts in the LGB group compared to the SCD group was due to both a higher degree of sequestration in the device (eluted cells), and a higher degree of destruction of leukocytes (by mass balance). Destruction of cellular elements within the blood was reflected in the higher free hemoglobin and MPO levels in the LGB versus SCD. Platelet dynamics with over an 80% reduction within the first 15 minutes followed by a recovery to 50% of the pre-study platelet concentration, are suggestive of rapid initial phase of platelet binding to circuit components, followed by subsequent release.

To further assess the influence of the SCD to lower circulating leukocyte counts, a bovine model utilizing CPB was examined. CPB performed without SCD demonstrated a small, but not statistically significant reduction of WBC counts in the first 60 minutes of CPB perfusion most likely due to non-specific attachment along the artificial membranes and blood tubing of the perfusion circuit. After 60 minutes, the WBC counts increased two-fold, and neutrophils increased up to five-fold relative to starting values. When the SCD was placed in the circuit utilizing systemic heparinization, leukocyte reduction was achieved for 2 hours, but led to a large increase in neutrophils at later time points and following SCD removal. When the SCD perfusion circuit was regionally perfused with citrate to lower ionized calcium to 0.25 to 0.40 mM, leukocyte and neutrophil counts remained low throughout CPB, even after removal of the SCD (routinely at t=225 min) for the final measurement 15 minutes after SCD removal.

The WBC and neutrophil kinetics in these bovine studies also provide insight into the manner in which SCD treatment may influence the leukocyte response to CPB. The number of neutrophils sequestered in the SCD was approximately $10^8$ cells, a small percentage of the circulating and marginated pool. However, the magnitude of neutrophil release from bone marrow and marginated stores in response to the systemic insult of CPB was blunted with SCD, especially with regional citrate infusion, suggesting that SCD-C treatment may alter the kinetics of neutrophil apoptosis and/or signals required for recruitment of neutrophils from marginated or bone marrow pools.

Further, the finding that the number of leukocytes eluted from the SCD during citrate infusion was 10-fold less than in the heparin condition, while maintaining lower leukocyte concentration in blood suggests that the low-iCa environment may promote the adhesion of activated leukocytes, followed by release after a time period of sequestration and deactivation. The kinetics of this "catch and release" phenomenon is supported with published and ongoing studies utilizing in vitro shear chambers. These in vitro and ex vivo studies suggest that the SCD devices of the invention may ameliorate the natural progression of SIRS by blunting the systemic leukocyte response leading to improved cardiovascular stability, respiratory performance and renal function. This study demonstrates a preventative therapeutic approach to ameliorate CPB promoted leukocyte response and lessen progression to MOD. The in vitro and ex vivo data provided herein demonstrates the safety and efficacy of the SCD for CPB applications.

Example 4. Exemplary SCD Cartridge for Use in Treating an Inflammatory Condition in a Subject To demonstrate the efficacy of the SCD cartridges of the invention, subjects (for example, porcine animal model or a human subject) with various inflammatory conditions may be treated with a SCD device listed below in Table 7 using the protocols described above to improve cardiovascular and/or renal parameters.

TABLE 7

Exemplary SCD Cartridges

| Device | ECS SA ($m^2$) | ECS SA ($cm^2$) | ECS Fill ($cm^3$) | SA/V ($cm^{-1}$) |
|---|---|---|---|---|
| 1 | 0.98 | 9800 | 130 | 75 |
| 2 | 2.5 | 25000 | 250 | 100 |
| 3 | 1.25 | 12500 | 125 | 100 |
| 4 | 2.5 | 25000 | 125 | 200 |
| 5 | 2.5 | 25000 | 109 | 230 |
| 6 | 2.5 | 25000 | 94 | 267 |
| 7 | 5 | 50000 | 93 | 536 |
| 8 | 5 | 50000 | 125 | 400 |
| 9 | 6.7 | 67000 | 125 | 537 |
| 10 | 10 | 100000 | 125 | 800 |

The SCD cartridges of the invention may also be adapted for treating small subjects (for example, pediatric patients) with inflammatory conditions. Table 8 depicts various SCD cartridges that may be useful in such applications.

TABLE 8

Exemplary SCD Cartridges

| Device | ECS SA ($m^2$) | ECS SA ($cm^2$) | ECS Fill ($cm^3$) | SA/V ($cm^{-1}$) |
|---|---|---|---|---|
| 1 - 1.5 cm case; 200 μm fibers | 0.17 | 1700 | 9 | 185 |
| 2 - 1.5 cm case; 100 μm fibers | 0.35 | 3500 | 9 | 392 |
| 3 - 1.5 cm case; 75 μm fibers | 0.47 | 4700 | 9 | 530 |
| 4 - 1.5 cm case; 50 μm fibers | 0.70 | 7000 | 9 | 784 |
| 5 - 2.5 cm case; 200 μm fibers | 0.49 | 4900 | 25 | 199 |
| 6 - 2.5 cm case; 100 μm fibers | 0.98 | 9800 | 25 | 399 |
| 7 - 2.5 cm case; 75 μm fibers | 1.30 | 13000 | 25 | 526 |
| 8 - 2.5 cm case; 50 μm fibers | 1.96 | 19600 | 25 | 797 |

Example 5. Treatment of Chronic Inflammation Associated with Chronic Heart Failure in an Animal Model Chronic heart failure (CHF) is recognized as associated with chronic systemic inflammation, especially monocyte/macrophage activation (Conraads et al. (2005) J. HEART LUNG TRANSPLANT. 24(7): 854-59). This example describes in vivo experiments that evaluate the effect of SCD cartridges on the chronic inflammatory state associated with CHF. This example further describes experiments that assess the acute and chronic effects of SCD cartridges on the cardiovascular and renal functions in an animal model of CHF. The results demonstrate that the SCD improved cardiovascular parameters and altered the pro-inflammatory phenotype of monocytes.

(I) Methods and Materials
A—Animal Model
The efficacy of the SCD cartridge in treating chronic inflammation and in improving cardiorenal functions was evaluated in a canine model of CHF.

CHF in this model is induced by multiple sequential intracoronary embolizations with polystyrene Latex microspheres (approximately 90 μm in diameter) that lead to loss of viable myocardium. The model manifests many of the sequelae of CHF in humans including profound systolic and increased systemic vascular resistance (SVR) and decreased cardiac output (CO) (Sabbah et al. (1991) AM. J. PHYSIOL. 260: H1379-84). The model also possesses the nearly entire spectrum of cellular, biochemical and molecular abnormalities that have been shown to occur during the development of CHF (See e.g., Kono et al. (1992) CIRCULATION 86(4): 1317-22; Imai et al. (2007) J. AM. COLL. CARDIOL. 49(21): 2120-28; Morita et al. (2006) AM. J. PHYSIOL. HEART CIRC. PHYSIOL. 290(6): H2522-7). Further, long-term therapy with ACE inhibition, beta-adrenergic blockade, aldosterone blockade and angiotensin-1 receptor blockade in this model elicits benefits that are identical to those reported in human patients with CHF (Morita et al. (2002) CARDIOVASC. DRUGS THER. 16(5): 443-9; Sabbah et al. (1994) Circulation 89(6): 2852-9; Suzuki et al. (2003) BR. J. PHARMACOL. 138(2): 301-9; Suzuki et al. (2002) Circulation 106(23): 2967-72). Accordingly, this model provides the ability to predict efficacy of new therapies for treatment of CHF.

Three groups of animals with advanced CHF were utilized for this study: one group was treated with the SCD cartridge and systemic heparin anticoagulation to maintain patency of the extracorporeal circuit (SCD-H; n=2); a second group was treated with the SCD cartridge and regional citrate anticoagulation (SCD-C; n=3), which provided patency and the additional therapeutic benefit associated with low iCa environment within the extracorporeal circuit; and a third group was treated with a cartridge without any hollow fibers (sham control, n=3).

Figure 18:
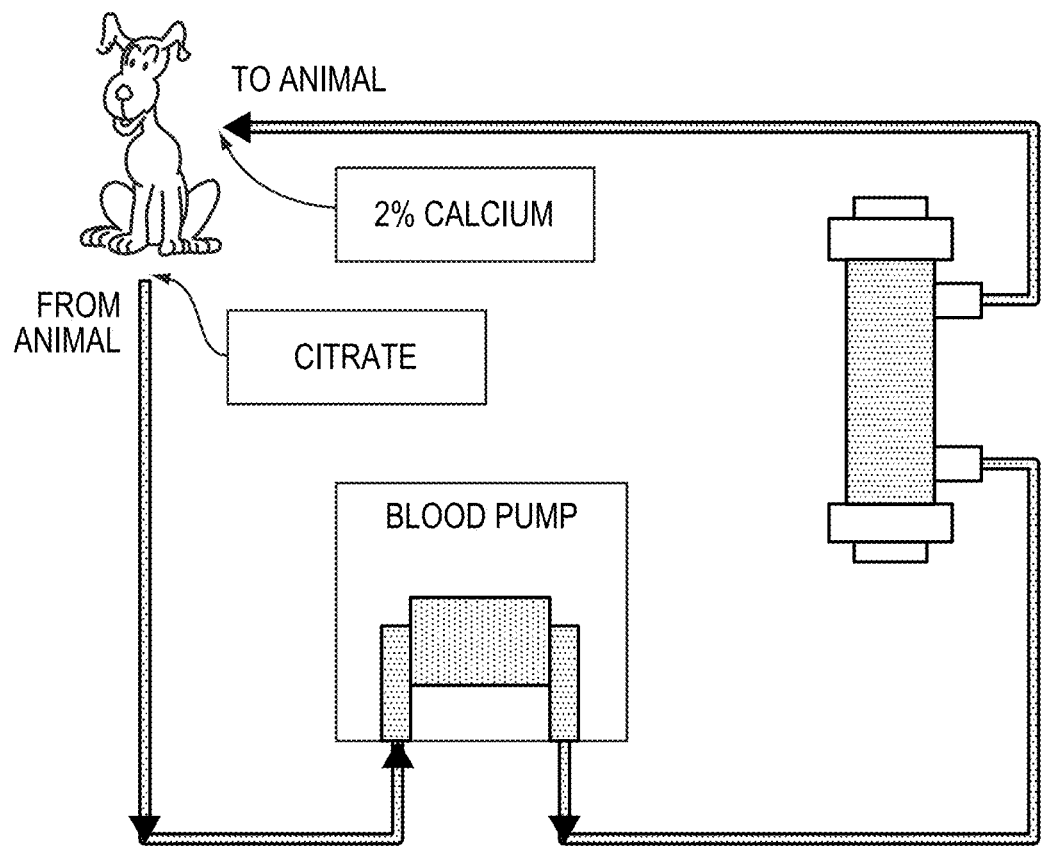
FIG. 18 is a schematic representation of an embodiment of a system configuration for use in treating a subject with chronic heart failure.

In all studies, extracorporeal circuits (see FIG. 18) were maintained for 4 hours, and then discontinued with the removal of the circuit and its blood volume for 2 hours. Hemodynamic and ventricular function parameters were measured at baseline and at 2, 4, and 6 hours after initiation of SCD (heparin or citrate) therapy or with sham control. Blood samples were obtained at baseline and at 2, 4 and 6 hours for the assessment of various biologic parameters.

(II) Results and Discussion
A—Observations of Cardiovascular Parameters
The canine model of chronic heart failure was utilized to evaluate the effectiveness of SCD cartridges having with either systemic heparin or regional citrate anticoagulation. Specifically, one group of animals (SCD-H) was treated with systemic heparin anticoagulation, and a second group of animals (SCD-C) was treated with regional citrate anticoagulation.

Figure 19A:
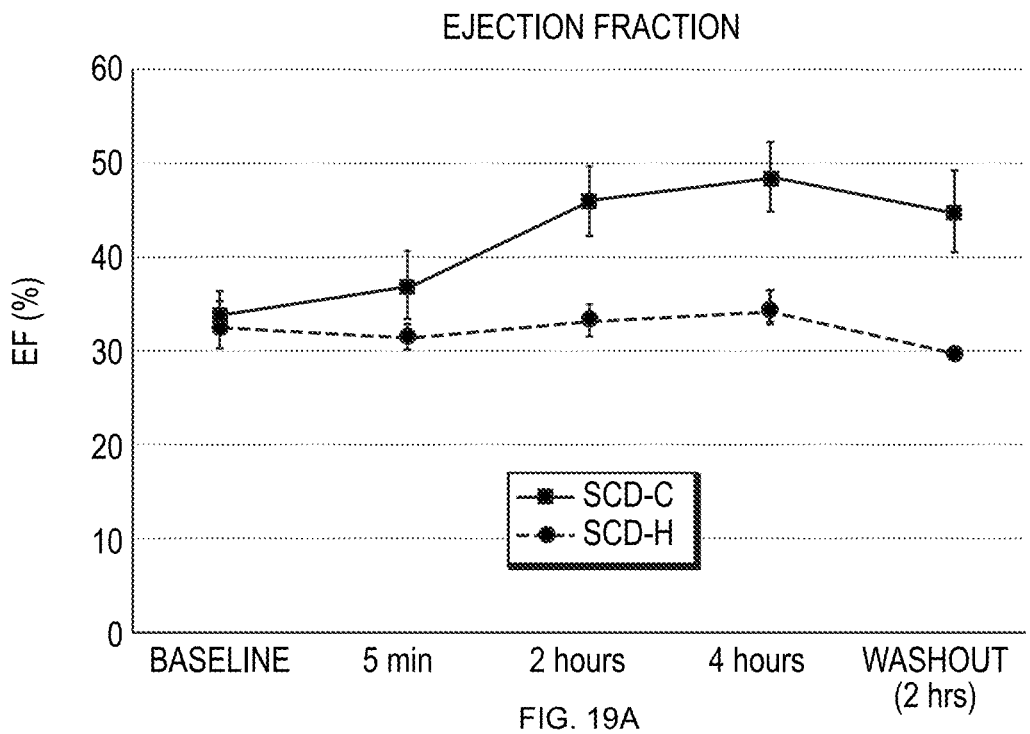
FIGS. 19A-C are graphical depictions of changes in cardiovascular parameters of subjects with chronic heart failure when treated with a SCD device in the presence of heparin (SCD-H) or a SCD device in the presence of citrate (SCD-C). Results are shown for ejection fraction (FIG. 19A); cardiac output (FIG. 19B); and systemic vascular resistance (FIG. 19C).

As depicted in FIG. 19A, Left ventricular (LV) ejection fraction (EF) increased in the SCD-C group within 5 minutes of starting treatment. Further, LV EF of increased substantially in the SCD-C group from 34%±2.3% to near normal values of 48%±3.7% while the SCD-H and sham control did not change. In particular, the SCD-C group increased to near normal EF values at 2 and 4 hours of treatment and was sustained during the 2 hour post therapy. This effect was not due to a decline in systemic vascular resistance which was similar in all groups. Stroke volume (SV) also increased within 5 minutes of starting treatment and increased from 26.7±4.9 to 35.3±7.3 mL in the SCD-C group (data not shown). The SCD-H group showed a decline in SV of from 26±1.4 to 25±2.1 mL after 4 hours of treatment to 20 mL following 2 hours post treatment.

Figure 19B:
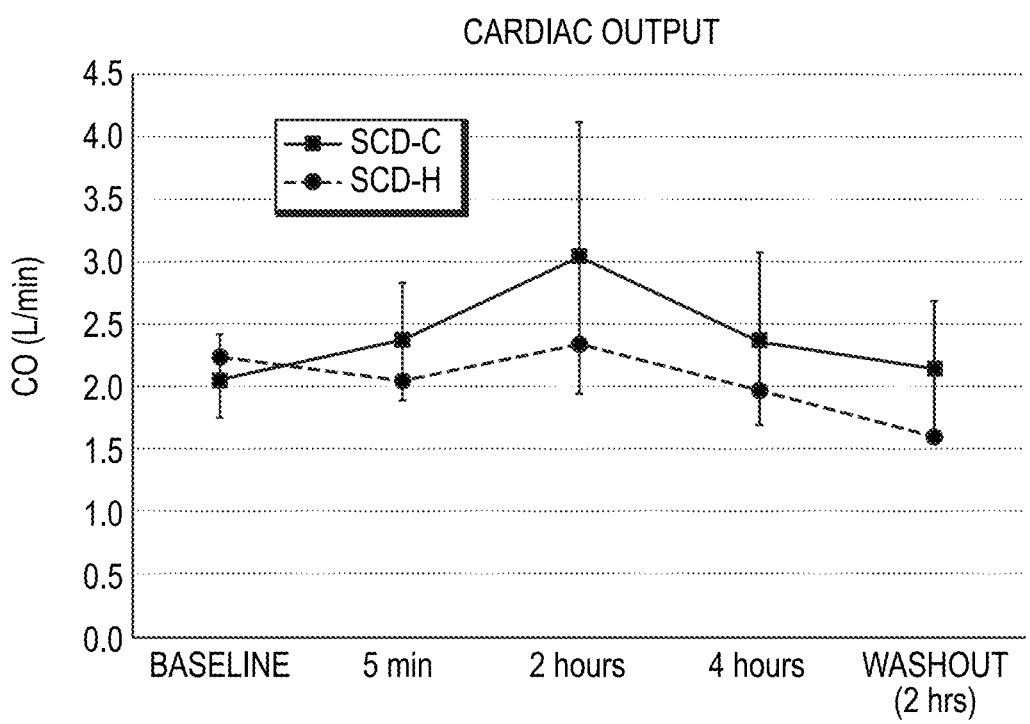

Cardiac output (CO) was also assessed (FIG. 19B). CO increased within 4 hours of SCD-C treatment from 2.40±0.15 to 2.77±0.95 L/min, and this elevation was maintained for 2 hours post-treatment. In comparison, SCD-H treatment resulted in a decline in CO from 2.22±0.5 to 1.97±0.03 L/min within four hours of treatment, and further reduced to 1.56 L/min during the 2 hour post-treatment period.

Figure 19C:
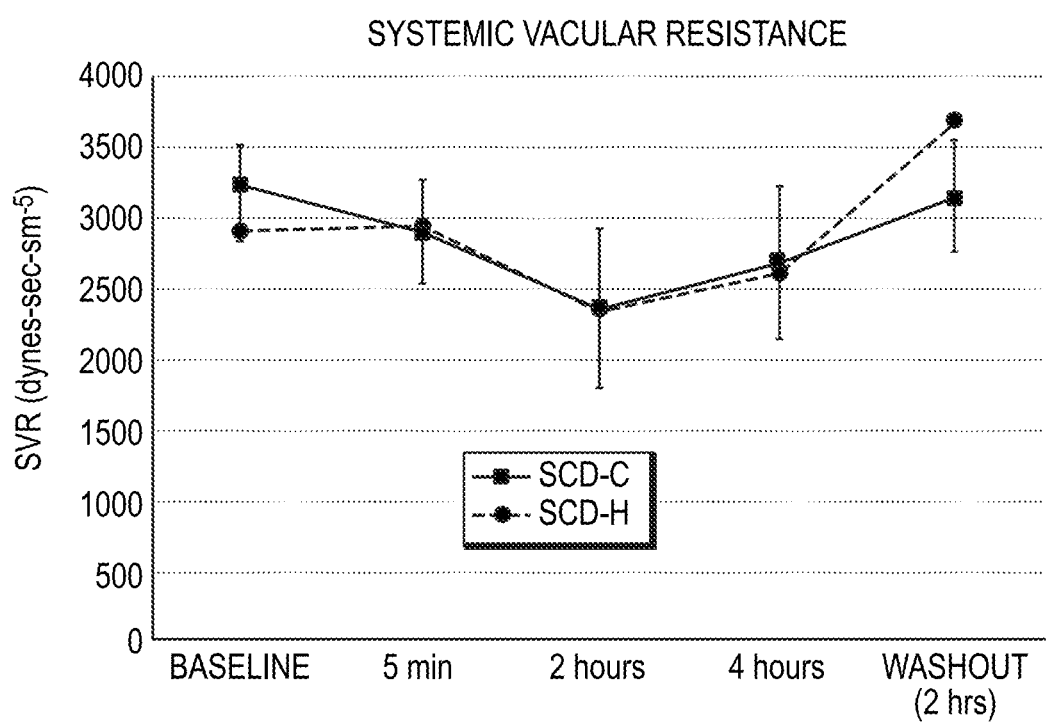

Systemic vascular resistance (SVR) showed a modest decline in both the SCD-C and SCD-H groups with baseline values at 2985±215 and 2898±62 to 2415±847 and 2599±76 dynes/sec/cm$^{-5}$ at 4 hours of therapy, respectively (FIG. 19C). At 2 hours post-treatment, SVR in the SCD-C group returned to baseline levels, while the SVR in the SCD-H group was slightly elevated compared to baseline. No episodes of arrhythmias or hypotension were observed during the treatment period.

Figure 21A:
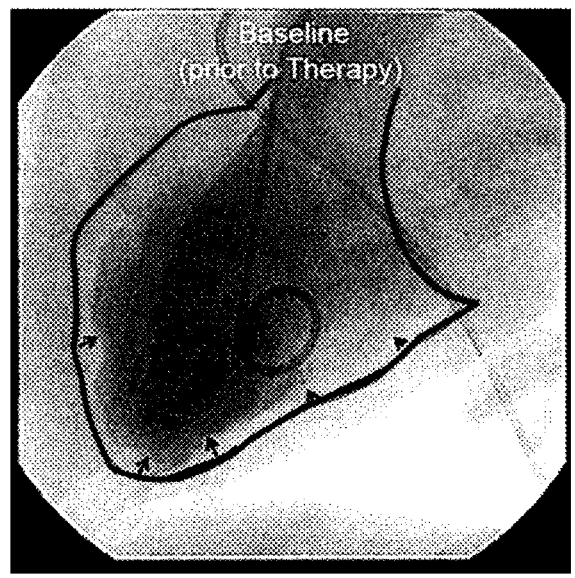
FIGS. 21A-B show ventriculograms of a heart of a dog with CHF shown at baseline (before therapy) (FIG. 21A) and at the end of four hours of SCD therapy (FIG. 21B). The solid black line (bordered by arrows) depicts the border of the left ventricular diastolic silhouettes (most relaxed state during filling) overlayed on the left ventricular systolic image (most contracted state) demonstrating improved contractility of the left ventricle (black arrows), especially at the apex of the left ventricle, after therapy (see FIG. 21B versus FIG. 21A).
Figure 21B:
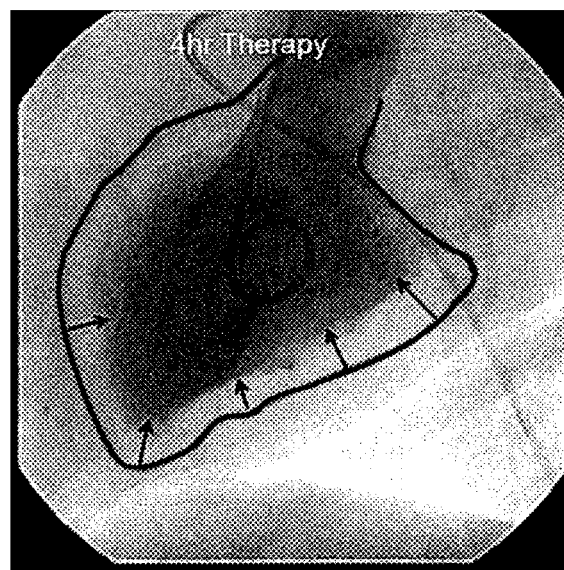

Ventriculograms demonstrated the SCD-C to convert viable but non-contracting myocardium into contracting myocardium. Exemplary ventriculograms are shown in FIG. 21 in a dog model before (FIG. 21A) and after (FIG. 21B) treatment. The red line depicts the border of the left ventricular diastolic silhouettes (most relaxed state during filling) overlayed on the left ventricular systolic image (most contracted state) demonstrating significantly improved contractility of the left ventricle (black arrows), especially at the apex of the left ventricle, after therapy (FIG. 21B versus FIG. 21A). The results are consistent with the results of increased cardiac output following SCD-citrate therapy.

Figure 20A:
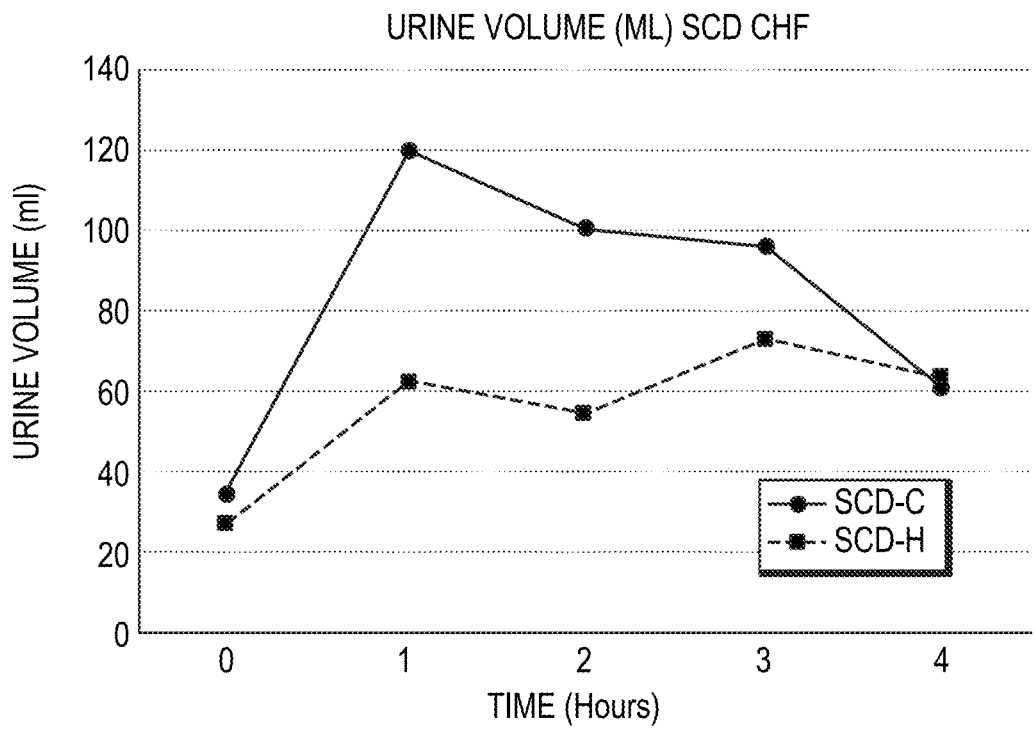
FIGS. 20A-D are graphical depictions of changes to certain renal functions upon treatment, including, the urine volume of subjects with chronic heart failure treated with a SCD device in the presence of heparin (SCD-H) or a SCD device in the presence of citrate (SCD-C) (FIG. 20A); percent fractional excretion (FE) of sodium (Na) in subjects with chronic heart failure treated with a SCD device in the presence of heparin (SCD-H), or a SCD device in the presence of citrate (SCD-C), or a CHF sham control (FIG. 20B), percent fractional excretion of urea in subjects with chronic heart failure treated with a SCD device in the presence of heparin (SCD-H), or a SCD device in the presence of citrate (SCD-C), or a CHF sham control (FIG. 20C), and mean renal sodium excretion (mmol/hour) of subjects with chronic heart failure treated with a SCD device in the presence of heparin (Hep) or a SCD device in the presence of citrate (Cit) (FIG. 20D).
Figure 20B:
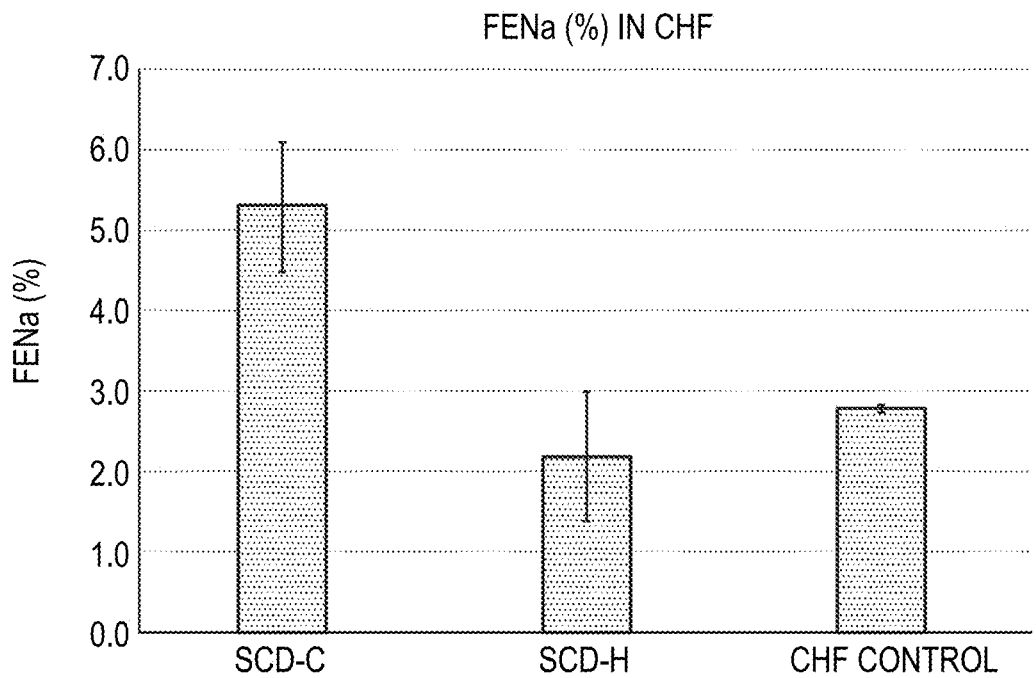
Figure 20C:
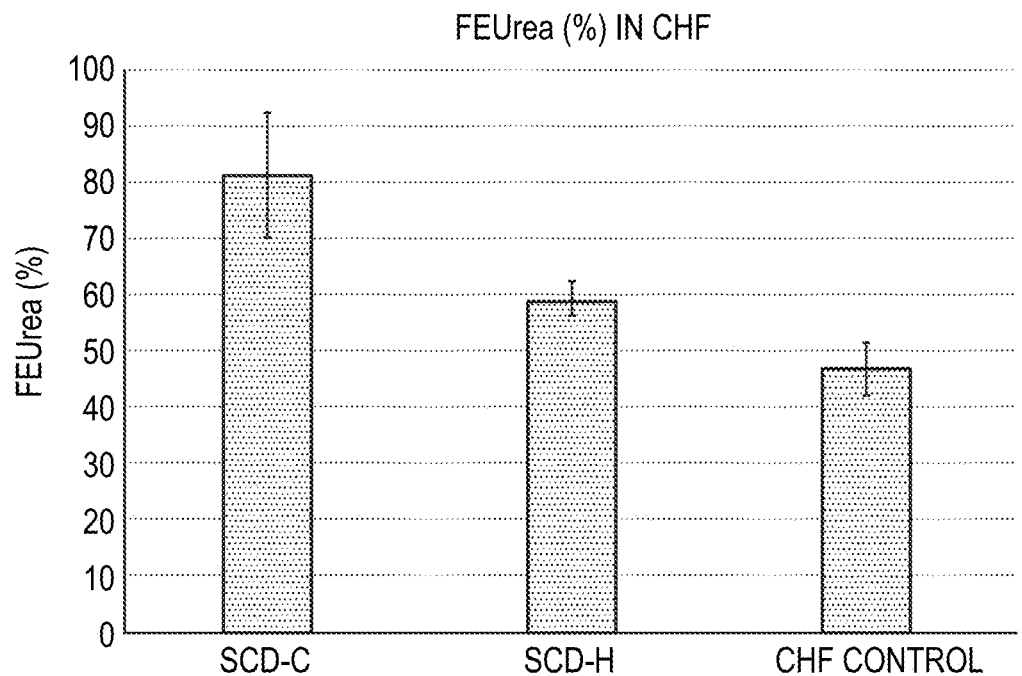
Figure 20D:
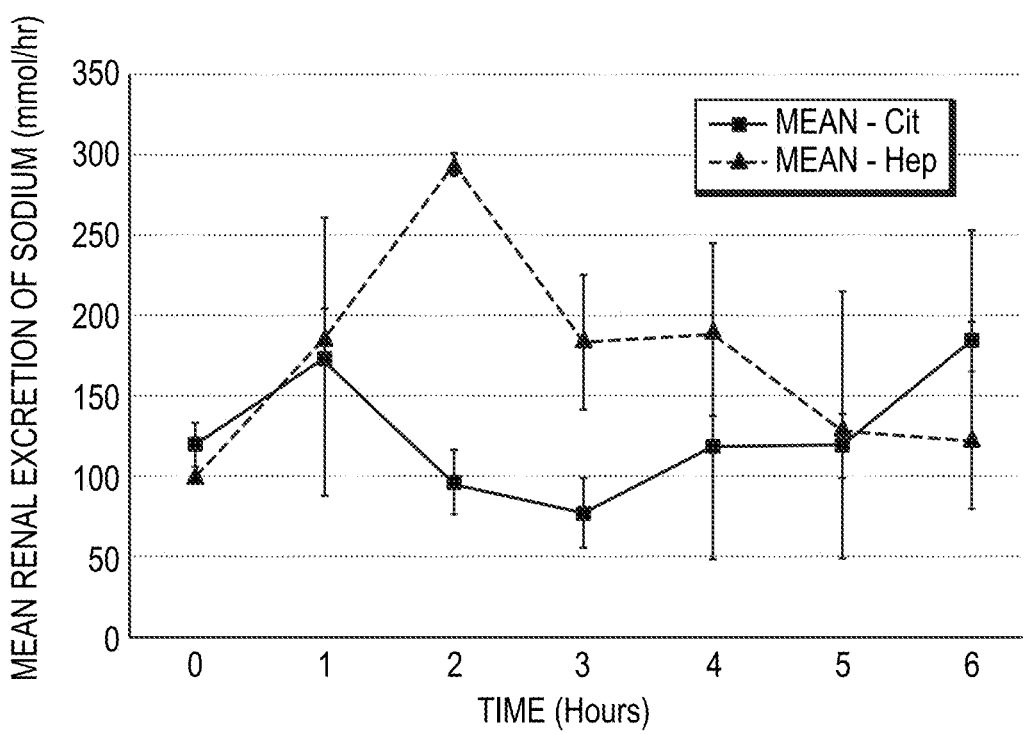

The renal effects were also substantive. Urine volume increased immediately within the first hour of SCD-C treatment and continued to be higher than SCD-H treatment for the entire 4 hours of treatment (see, FIG. 20A). The fractional excretion (FE) of sodium nearly doubled in the SCD-C compared to SCD-H increasing from 2.2%±0.8% to 5.3%±0.8% (see, FIG. 20B) and FE of urea went from 59%±3.1% to 81%±11.3% (see, FIG. 20C). No adverse events of arrhythmia or hypotension were observed during treatment. Total urine sodium excretion (see, FIG. 20D) was also increased during the 4 hours of SCD-C treatment compared to SCD-H.

Collectively, these data indicate that SCD-C treatment significantly improved cardiac contractility and function.

B—Observations of Leukocyte Sequestration and Activation

To evaluate the effect of SCD influence on the activation process of circulating monocytes, a variety of biomarkers were measured in isolated peripheral blood monocytes after LPS stimulation at various times during the treatment periods with established methods (Simms et al. (1999) AM. J. PHYSIOL. 277: H253-60). As indicated in Table 9, SCD-C treatment resulted in a decline in LPS stimulated monocyte release of IL-6 and TNF-α, demonstrating an immunomodulatory effect of SCD-C treatment on the systemic pool of circulating monocytes.

TABLE 9

LPS stimulated Cytokine Release by Isolated Monocytes (MNC)

| Timeline | Baseline | 2 hour | 4 hour | Washout (2 hour) |
|---|---|---|---|---|
| IL6 (ng/10$^6$ MNC/24 hr) | 4.56 ± 0.91 | 3.37 ± 1.31 | 2.10 ± 0.30 | 1.92 ± 0.67 |
| TNFa (ng/10$^6$ MNC/24 hr) | 6.53 ± 0.53 | 2.88 ± 0.27 | 4.08 ± 1.82 | 1.61 ± 0.17 |

To assess the sequestration of activated leukocytes along the SCD membranes, the SCD cartridges were processed at the end of the treatment period and the types of adherent leukocytes were determined using established methods (Ding et al. (2011) PLoS ONE 6(4): e18584). The number of eluted cells in the SCD-C and SCD-H groups were 1.06×10$^9$ and 7.2×10$^9$ leukocytes, respectively. The types of leukocytes were 68% and 80% neutrophils, 28% and 16% monocytes, and 4% and 4% eosinophils in the SCD-C and SCD-H groups, respectively. Of note, the ratio of eluted monocytes to neutrophils was four times greater than the baseline ratio of circulating monocytes to neutrophils. Specifically, the number of monocytes eluted from the SCD membrane after 4 hours of SCD-C therapy was 90% of the baseline absolute number of circulating monocytes. These results indicate that replacement of the circulating systemic monocytes may have occurred from the mobilization of a non-circulating monocyte pool, most likely the spleen (Swirski et al. (2009) SCIENCE 325(5940): 612-6). The results also suggest that SCD-C treatment affects the circulating pool of leukocytes and alters the pro-inflammatory phenotype of monocytes.

The change in inflammatory parameters was associated with dramatic increases in EF and CO in SCD-C treated CHF animals compared to SCD-H controls. Collectively these data suggest that SCD-C treatment reduces the cardiodepressant state of chronic inflammation associated with CHF.

Example 6. Case Study of Subject with Acute Decompensated Heart Failure after Undergoing SCD-Citrate Therapy A 45 year old male patient presented with acute decompensated heart failure. In particular, the patient presented with longstanding systolic heart failure (ejection fraction of about 20%) after gaining 18 pounds of weight in two weeks. The patient had a history of diabetes, sleep apnea, chronic kidney disease, atrial fibrillation and implantable cardiac defibrillator (ICD) placement. The subject has increasing shortness of breath being unable to walk 10 yards and increasing lower extremity edema.

The patient was treated with intravenous dobutamine infusion and a Lasix (furosemide, a high potency diuretic) drip with persistent oliguria. The patient's blood urea nitrogen (BUN) value and serum creatine (Scr) value were 64 and 3.38 (baseline Scr 1.5), respectively. A transoesophogeal echocardiogram (TEE) was performed, which showed that the subject had a pulmonary capillary wedge pressure (PCWP) of 30 (normally less than about 15), a cardiac index (CI, a measure of cardiac output per weight of an individual) of 1.4 (normally in the range of 2.5-3.0), a cardiac output (C.O.) of 3 L/minute on Milrinone (normally greater than 5 L/minute), and an ejection fraction (EF) of 10%. The patient was started on therapy with continuous venovenous hemofiltration (CVVH) with SCD-citrate for about 5 days with the SCD cartridge being changed once every 24 hours. The fluid output was measured on each of the five days of SCD therapy and then for three follow-up days post SCD therapy, and the results are summarized in Table 10.

TABLE 10

|  | SCD Treatment Day | | | | | | Follow Up Day | | |
| --- | --- | --- | --- | --- | --- | --- | --- | --- | --- |
|  | 0 | 1 | 2 | 3 | 4 | 5 | 1 | 2 | 3 |
| Urine Output (mL) | 575 | 1,000 | 925 | 1,020 | 1,230 | 540 | 135 | 390 | 500 |
| Net Fluid Balance (mL) | Not available | −3,071 | +269 | −5,837 | −4,449 | −1,466 | 1,994 | 1,809 | |

Net fluid balance represents the sum of urine volume and the volume of ultrafiltrate removed by the CVVH minus the fluid (e.g., saline) added back to the patient. The results show that on day 1 of the treatment the net fluid balance was −3,071 mL, which peaked at about −5,837 mL on day 3. On day 2, the subject was partially rehydrated before removing additional fluid. During the five days of therapy on the SCD with regional citrate, the net fluid balance decreased by 14.5 L. During the follow-up days the patient was rehydrated. These findings demonstrate that the SCD device with regional citrate was able to remove fluid from the subject that was not possible without the SCD cartridge. The SCD therapy improved the cardiovascular performance of the patient resulting in fluid removal not readily attained with current therapy.

INCORPORATION BY REFERENCE

The entire disclosure of each of the publications and patent documents referred to herein is incorporated by reference in its entirety for all purposes to the same extent as if each individual publication or patent document were so individually denoted.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of increasing myocardial function in a subject with chronic heart failure, the method comprising:
   (a) extracorporeally sequestering activated leukocytes and/or activated platelets present in blood from the subject in a cartridge, the cartridge comprising:
      (i) a rigid housing defining an inner volume (IV), a fluid inlet port and a fluid outlet port, wherein the inner volume is in fluid flow communication with the fluid inlet port and the fluid outlet port, and
      (ii) a solid support disposed within the housing and defining a fluid contacting surface with a surface area (SA) capable of sequestering activated leukocytes and/or activated platelets, if present in blood entering the housing via the fluid inlet port, and the blood is introduced into the housing via the fluid inlet port under conditions that permit sequestration of the activated leukocytes and/or activated platelets on the fluid contacting surface of the solid support; and
   (b) treating the leukocytes and/or platelets sequestered in step (a) to inhibit release of a pro-inflammatory substance or to deactivate the leukocytes and/or platelets thereby to increase myocardial function of the subject when compared to the myocardial function of the subject prior to treatment, wherein the myocardial function is selected from the group consisting of left ventricular ejection fraction, cardiac output, systemic vascular resistance, left ventricular stroke volume, aortic pressure, left ventricular pressure, peak rate of change of left ventricular pressure during isovolumic contraction and relaxation, left ventricular end-diastolic pressure, myocardial oxygen consumption, and coronary flow reserve.

2. The method of claim 1, wherein the cartridge provided in step (a) has an SA/IV ratio greater than 25 cm'.

3. The method of claim 1, wherein the cartridge provided in step (a) has an SA/IV ratio ranging from 25 cm$^{-1}$ to 2,000 cm$^{-1}$.

4. The method of claim 1, wherein the cartridge provided in step (a) has an SA/IV ratio no greater than 80 cm$^{-1}$.

5. The method of claim 1, wherein the solid support is disposed within the housing at a packing density ranging from 20% to 65%.

6. The method of claim 1, wherein the solid support comprises a fiber.

7. The method of claim 1, wherein the SA of the cartridge provided in step (a) ranges from 0.1 m$^2$ to 5.0 m$^2$.

8. The method of claim 1, wherein the inner volume ranges from 15 cm$^3$ to 120 cm$^3$.

9. The method of claim 1, further comprising permitting the blood to exit the cartridge via the fluid outlet port at a flow rate ranging from 10 cm$^3$/minute to 8,000 cm$^3$/minute.

10. The method of claim 1, wherein fluid flow within the cartridge is in a direction substantially parallel to the solid support.

11. The method of claim 1, wherein, in step (b), the leukocytes and/or platelets are treated with a calcium chelating agent.

12. The method of claim 11, wherein the calcium chelating agent is citrate.

13. The method of claim 11, wherein the calcium chelating agent is introduced into the blood from the subject prior to step (a).

14. The method of claim 11, wherein the leukocytes and/or platelets from the subject are treated over a period of at least 2 hours, at least 4 hours, at least 6 hours, at least 8 hours, or at least 12 hours.

15. The method of claim 11, wherein the leukocytes and/or platelets from the subject are treated over a period of 2 to 48 hours, 2 to 24 hours, 2 to 12 hours, 4 to 48 hours, 4 to 24 hours, or 4 to 12 hours.

16. The method of claim 1, wherein the subject has myocardial dysfunction secondary to inflammatory cell penetration of heart tissue.

17. The method of claim 1, wherein the subject has received a heart transplant.

18. The method of claim 1, wherein the increased myocardial function is maintained for at least 6 hours after termination of the treating in step (b).

19. The method of claim 18, wherein the increased myocardial function is maintained for at least 24 hours after termination of the treating in step (b).

20. The method of claim 1, wherein the solid support comprises a membrane.

21. A method of increasing myocardial function in a subject with chronic heart failure, the method comprising:
   (a) extracorporeally sequestering activated leukocytes and/or activated platelets present in blood from the subject; and
   (b) treating the leukocytes and/or platelets sequestered in step (a) to inhibit release of a pro-inflammatory substance or to deactivate the leukocytes and/or platelets thereby to increase myocardial function of the subject when compared to the myocardial function of the subject prior to treatment, wherein the myocardial function is selected from the group consisting of left ventricular ejection fraction, cardiac output, systemic vascular resistance, left ventricular stroke volume, aortic pressure, left ventricular pressure, peak rate of change of left ventricular pressure during isovolumic contraction and relaxation, left ventricular end-diastolic pressure, myocardial oxygen consumption, and coronary flow reserve.

22. The method of claim 21, wherein, in step (b), the leukocytes and/or platelets are treated with a calcium chelating agent.

23. The method of claim 22, wherein the calcium chelating agent is citrate.

24. The method of claim 22, wherein the calcium chelating agent is introduced into the blood from the subject prior to step (a).

25. The method of claim 22, wherein leukocytes and/or platelets from the subject are treated over a period of at least 2 hours, at least 4 hours, at least 6 hours, at least 8 hours, or at least 12 hours.

26. The method of claim 22, wherein leukocytes and/or platelets from the subject are treated over a period of 2 to 48 hours, 2 to 24 hours, 2 to 12 hours, 4 to 48 hours, 4 to 24 hours, or 4 to 12 hours.

27. The method of claim 22, wherein the increased myocardial function is maintained for at least 6 hours after termination of the treatment in step (b).

28. The method of claim 22, wherein the increased myocardial function is maintained for at least 24 hours after termination of the treatment in step (b).

29. The method of claim 22, wherein, in step (a), the activated leukocytes and/or activated platelets are sequestered by introducing the blood into a cartridge comprising
   (i) a rigid housing defining an inner volume (IV), a fluid inlet port and a fluid outlet port, wherein the inner volume is in fluid flow communication with the fluid inlet port and the fluid outlet port, and
   (ii) a solid support disposed within the housing and defining a fluid contacting surface with a surface area (SA) capable of sequestering activated leukocytes and/or platelets, if present in the blood entering the housing via the fluid inlet port, wherein the blood is introduced into the housing via the fluid inlet port under conditions that permit sequestration of the activated leukocytes and/or platelets on the fluid contacting surface of the solid support.

30. The method of claim 29, wherein the cartridge provided in step (a) has an SA/IV ratio in a range of from 25 $cm^{-1}$ to 1,500 $cm^{-1}$.

31. The method of claim 30, wherein the SA/IV ratio is in a range of from 80 $cm^{-1}$ to 1,500 $cm^{-1}$.

32. The method of claim 29, wherein the cartridge provided in step (a) has an SA/IV ratio is no greater than 80 $cm^{-1}$.

33. The method of claim 29, wherein the solid support is disposed within the housing at a packing density in a range from 20% to 65%.

34. The method of claim 29, wherein the solid support comprises a membrane.

35. The method of claim 29, wherein the solid support comprises a fiber.

36. The method of claim 29, wherein the SA of the cartridge provided in step (a) is in a range of from 0.1 $m^2$ to 5.0 $m^2$.

37. The method of claim 29, further comprising permitting the blood to exit the cartridge via the fluid outlet port at a flow rate in a range of 10 $cm^3$/minute to 8,000 $cm^3$/minute.

38. The method of claim 29, wherein fluid flow within the cartridge is in a direction substantially parallel to the solid support.

39. A method of treating a subject having or at risk of developing an inflammatory condition, wherein the inflammatory condition is chronic heart failure (CHF), the method comprising:
   (a) providing a cartridge comprising
      (i) a rigid housing defining an inner volume (IV), a fluid inlet port and a fluid outlet port, wherein the inner volume is in fluid flow communication with the fluid inlet port and the fluid outlet port; and
      (ii) a fluid permeable solid support disposed within the housing and defining a fluid contacting surface with a surface area (SA) capable of sequestering an activated leukocyte, if present in blood entering the housing via the fluid inlet port, wherein the cartridge has an SA/IV ratio of no greater than 80 $cm^{-1}$; and
   (b) introducing blood from the subject into the housing via the fluid inlet port under conditions that permit sequestration of the activated leukocyte on the fluid contacting surface of the solid support.

40. The method of claim 39, further comprising
   (c) treating the leukocyte sequestered in step (b) to reduce in the subject the risk of developing inflammation associated with the inflammatory condition or to alleviate inflammation associated with the inflammatory condition.

41. The method of claim 40, further comprising the step of returning the leukocyte and/or the platelet produced in step (c) back to the subject.

42. The method of claim 40, wherein, in step (c), the leukocyte and/or the platelet is treated with a calcium chelating agent.

43. The method of claim 42, wherein the calcium chelating agent is citrate.

44. The method of claim 42, wherein the solid support comprises a membrane.

45. The method of claim 42, wherein the solid support comprises a fiber.

46. The method of claim 42, wherein the SA of the cartridge provided in step (a) is in a range of from 0.1 $m^2$ to 10.0 $m^2$.

47. The method of claim 42, wherein the SA of the cartridge provided in step (a) is in a range of from 0.1 $m^2$ to 5.0 $m^2$.

48. The method of claim 42, wherein the inner volume is in a range of from 10 cm³ to 150 cm³.

49. The method of claim 42, wherein the inner volume is in a range of from 20 cm⁻¹ to 80 cm³.

50. The method of claim 49, further comprising permitting the blood to exit the cartridge via the fluid outlet port at a flow rate in a range of 10 cm³/minute to 8,000 cm⁻¹/minute.

* * * * *

UNITED STATES PATENT AND TRADEMARK OFFICE
CERTIFICATE OF CORRECTION

| | |
|---|---|
| PATENT NO. | : 11,439,739 B2 |
| APPLICATION NO. | : 16/935992 |
| DATED | : September 13, 2022 |
| INVENTOR(S) | : Humes et al. |

It is certified that error appears in the above-identified patent and that said Letters Patent is hereby corrected as shown below:

In the Claims

In Claim 2, at Column 60, Line 26, replace "25 cm'" with -- 25 $cm^{-1}$ --.

In Claim 49, at Column 63, Line 4, replace "20 $cm^{-1}$" with -- 20 $cm^3$ --.

In Claim 50, at Column 63, Line 7, replace "8,000 $cm^{-1}$/minute" with -- 8,000 $cm^3$/minute --.

Signed and Sealed this
Thirtieth Day of May, 2023

Katherine Kelly Vidal
*Director of the United States Patent and Trademark Office*